United States Patent
Collingwood et al.

(10) Patent No.: US 8,168,654 B2
(45) Date of Patent: May 1, 2012

(54) QUINUCLIDINE DERIVATIVES BINDING TO MUCARINIC M3 RECEPTORS

(75) Inventors: Stephen P Collingwood, Horsham (GB); Brian Cox, Horsham (GB); Urs Baettig, Horsham (GB); Gurdip Bhalay, Horsham (GB); Nicholas J Devereux, Horsham (GB)

(73) Assignee: Novartis AG, Basel (CH)

( * ) Notice: Subject to any disclaimer, the term of this patent is extended or adjusted under 35 U.S.C. 154(b) by 205 days.

(21) Appl. No.: 12/582,291

(22) Filed: Oct. 20, 2009

(65) Prior Publication Data

US 2010/0041887 A1    Feb. 18, 2010

Related U.S. Application Data

(63) Continuation of application No. 10/554,558, filed as application No. PCT/EP2004/004605 on Apr. 30, 2004, now abandoned.

(30) Foreign Application Priority Data

May 2, 2003  (GB) .................................. 0310232.4
Oct. 24, 2003  (GB) .................................. 0324887.9

(51) Int. Cl.
*A01N 43/90*   (2006.01)
*A61K 31/44*   (2006.01)
*C07D 453/02*  (2006.01)
*C07D 241/02*  (2006.01)

(52) U.S. Cl. .................... 514/305; 546/137; 544/406

(58) Field of Classification Search .............. 546/137; 544/406; 514/305
See application file for complete search history.

(56) References Cited

U.S. PATENT DOCUMENTS

| | | | |
|---|---|---|---|
| 3,714,357 A | 1/1973 | Gueremy et al. | |
| 7,723,356 B2 | 5/2010 | Press et al. | |
| 2009/0264461 A1* | 10/2009 | Monnier et al. | 514/305 |
| 2010/0168132 A1* | 7/2010 | Press et al. | 514/255.05 |

FOREIGN PATENT DOCUMENTS

| | | |
|---|---|---|
| CA | 2583237 | 10/2005 |
| DE | 28 54 308 | 6/1979 |
| EP | 1 302 458 | 4/2003 |
| WO | 01/04118 | 1/2001 |
| WO | 02/053564 | 7/2002 |
| WO | 03/053966 | 7/2003 |

OTHER PUBLICATIONS

Gosens et al., respiratory research, 2006, vol. 7(73), pp. 1-15.*
Evangelista et al., General Pharmacology, vol. 30, No. 4, pp. 513-519, (1998).
Dolle et al., Journal of Labelled Compounds & Radiopharmaceuticals, vol. 44, No. 5, pp. 337-345, (2001).
Godovikov et al., Khimiko-Farmatsevticheskii Zhurnal, vol. 19, No. 9, pp. 1060-1061, (1985).

* cited by examiner

*Primary Examiner* — Janet Andres
*Assistant Examiner* — Niloofar Rahmani
(74) *Attorney, Agent, or Firm* — Cozette M McAvoy

(57) ABSTRACT

Compounds of formula I

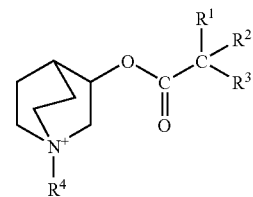

in salt or zwitterionic form wherein, wherein $R^1$, $R^2$, $R^3$, and $R^4$ have the meanings as indicated in the specification, are useful for treating conditions that are mediated by the muscarinic M3 receptor. Pharmaceutical compositions that contain the compounds and a process for preparing the compounds are also described.

16 Claims, No Drawings

QUINUCLIDINE DERIVATIVES BINDING TO MUCARINIC M3 RECEPTORS

This is a continuation of Application No. 10/554,558 filed on Oct. 3, 2006, which is a National Stage of International Application No. PCT/EP2004/004605 filed on Apr. 30, 2004, which claims benefit of Great Britain Appiication No. 0310232.4 filed on May 2, 2003 and Great Britain Application No. 0324887.9 filed on Oct. 24, 2003, the entre disclosures of which are hereby incorporated by reference.

This invention relates to organic compounds, their preparation and use as pharmaceuticals.

In one aspect the invention provides compounds of formula I

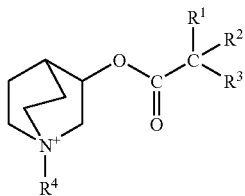

in salt or zwitterionic form wherein
$R^1$ and $R^3$ are each independently a $C_3$-$C_{15}$-carbocyclic group or a 4- to 12-membered heterocyclic group having at least one ring heteroatom selected from nitrogen, oxygen and sulphur,
or —$CR^1R^2R^3$ together form a group of formula

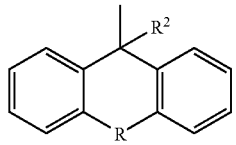

where R is a bond, —O—, —S—, —$CH_2$—, —CH═CH—, —$CH_2$—$CH_2$-, amino or —N($CH_3$)—;
$R^2$ is hydrogen, halo, hydroxy, $C_1$-$C_8$-alkoxy or $C_1$-$C_8$-alkyl optionally substituted by hydroxy;
$R^4$ is $C_1$-$C_8$-alkyl substituted by —$NHR^5$, —$NR^5$—CO—$R^6$, —$NR^5$—CO—NH—$R^7$, —$NR^5SO_2$—$R^8$, —CO—$NR^9R^{10}$, —$OR^{11}$, —O—CO—$NHR^{12}$, —O—CO—$R^{13}$ or —CO—O—$R^{14}$,
or $R^4$ is $C_3$-$C_{10}$-alkynyl optionally substituted by a $C_3$-$C_{15}$-carbocyclic group or a 4- to 12-membered heterocyclic group having at least one ring heteroatom selected from nitrogen, oxygen and sulphur;
$R^5$ is hydrogen or $C_1$-$C_8$-alkyl;
$R^6$ is $C_1$-$C_8$-alkyl, $C_2$-$C_8$-alkenyl, $C_2$-$C_{10}$-alkynyl or $C_1$-$C_8$-alkoxy in each case optionally substituted by a $C_3$-$C_{15}$-carbocyclic group or a 4- to 12-membered heterocyclic group having at least one ring heteroatom selected from nitrogen, oxygen and sulphur,
or $R^6$ is a $C_3$-$C_{15}$-carbocyclic group or a 4- to 12-membered heterocyclic group having at least one ring heteroatom selected from nitrogen, oxygen and sulphur;
$R^7$ is a $C_3$-$C_{15}$-is-carbocyclic group;
$R^8$ is a $C_3$-$C_{15}$-carbocyclic group;
$R^9$ is hydrogen or $C_1$-$C_8$-alkyl;
$R^{10}$ is hydrogen, $C_1$-$C_8$-alkyl optionally substituted by cyano, amino, nitro, carboxy, $C_1$-$C_8$-alkoxy, a $C_3$-$C_{15}$-carbocyclic group, or by a 4- to 12-membered heterocyclic group having at least one ring heteroatom selected from nitrogen, oxygen and sulphur,
or $R^{10}$ is a $C_3$-$C_{15}$-carbocyclic group or a 4- to 12-membered heterocyclic group having at least one ring heteroatom selected from nitrogen, oxygen and sulphur;
$R^{11}$ is hydrogen, $C_1$-$C_8$-alkyl, $C_1$-$C_8$-alkyl-$C_1$-$C_8$-alkoxy or $C_1$-$C_8$-alkyl-O—$R^{15}$;
$R^{12}$ is a $C_3$-$C_{15}$-carbocyclic group;
$R^{13}$ is $C_1$-$C_8$-alkyl or a $C_3$-$C_{15}$-carbocyclic group;
$R^{14}$ is hydrogen, a $C_3$-$C_{15}$-carbocyclic group, $C_1$-$C_8$-alkenyl, or $C_1$-$C_8$-alkyl optionally substituted by a $C_3$-$C_{15}$-carbocyclic group; and
$R^{15}$ is a $C_3$-$C_{15}$-carbocylic group.

Terms used in the specification have the following meanings:

"Optionally substituted" means the group referred to can be substituted at one or more positions, e.g. 1, 2 or 3 positions, by any one or any combination of the radicals described.

"$C_1$-$C_8$-alkyl" as used herein denotes straight chain or branched alkyl having 1 to 8 carbon atoms. Preferably, $C_1$-$C_8$-alkyl is $C_1$-$C_4$-alkyl.

"$C_1$-$C_8$-alkylene" as used herein denotes straight chain or branched alkylene that contains 1 to 8 carbon atoms. Preferably, $C_1$-$C_8$-alkylene is $C_1$-$C_4$-alkylene.

"$C_2$-$C_8$-alkenyl" as used herein denotes straight chain or branched hydrocarbon chains that contain two to eight carbon atoms and one or more carbon-carbon double bonds. Preferably "$C_2$-$C_8$-alkenyl" is "$C_2$-$C_4$-alkenyl".

"$C_2$-$C_{10}$-alkynyl" as used herein denotes straight chain or branched hydrocarbon chains that contain two to ten carbon acorns and one or more carbon-carbon triple bonds. Preferably "$C_2$-$C_{10}$-alkynyl" is "$C_3$-$C_8$-alkynyl".

"$C_3$-$C_{15}$-carbocyclic group" as used herein denotes a carbocyclic group having 3 to 15 ring carbon atoms, for example a monocyclic group, either cycloaliphatic, such as a $C_3$-$C_8$-cycloalkyl, or aromatic such as phenyl, which can be substituted by one or more, usually one or two, $C_1$-$C_4$-alkyl groups, or a bicyclic group such as bicyclooctyl, bicyclononyl including indanyl and indenyl, and bicyclodecyl including naphthyl, again any of which can be substituted by one or more, usually one or two, $C_1$-$C_4$-alkyl groups. Preferably the $C_3$-$C_{15}$-carbocyclic group is a $C_3$-$C_{10}$-carbocyclic group, for example cyclopropyl, cyclopentyl, cyclohexyl, cycloheptyl, phenyl, indanyl or naphthyl. The $C_3$-$C_{15}$-carbocyclic group can be substituted or unsubstituted. Preferred substituents include halo (e.g. fluoro, chloro or bromo), cyano, hydroxy, amino, nitro, carboxy, $C_1$-$C_8$-alkyl (e.g. methyl or ethyl), halo-$C_1$-$C_8$-alkyl, $C_1$-$C_8$-alkoxy, $C_1$-$C_8$-alkylcarbonyl, $C_1$-$C_8$-alkylsulfonyl, —$SO_2NH_2$, a $C_3$-$C_{15}$-carbocyclic group and a 5- to 12-membered heterocyclic group having at least one ring heteroatom selected from nitrogen, oxygen and sulphur.

"$C_3$-$C_8$-cycloalkyl" as used herein denotes cycloalkyl having 3 to 8 carbon atoms. Preferably "$C_3$-$C_8$-cycloalkyl" is "$C_3$-$C_8$-cycloalkyl".

"$C_1$-$C_8$-haloalkyl" as used herein denotes $C_1$-$C_8$-alkyl as hereinbefore defined substituted by one or more halogen atoms, preferably one, two or three halogen atoms. Preferably "$C_1$-$C_8$-haloalkyl" is "$C_1$-$C_4$-haloalkyl".

"$C_1$-$C_8$-alkylcarbonyl" as used herein denotes $C_1$-$C_8$-alkyl as hereinbefore defined linked to a carbonyl group. Preferably "$C_1$-$C_8$-alkylcarbonyl" is "$C_1$-$C_4$-alkylcarbonyl".

"$C_1$-$C_8$-alkylthio" as used herein denotes $C_1$-$C_8$-alkyl as hereinbefore defined linked to —S—. Preferably "$C_1$-$C_8$-alkylthio" is "$C_1$-$C_4$-alkylthio".

"$C_1$-$C_8$-alkylsulfonyl" as used herein denotes $C_1$-$C_8$-alkyl as hereinbefore defined linked to —$SO_2$—. Preferably "$C_1$-$C_8$-alkylsulfonyl" is "$C_1$-$C_4$-alkylsulfonyl".

"$C_1$-$C_8$-alkoxy" as used herein denotes straight chain or branched alkoxy having 1 to 8 carbon atoms. Preferably, $C_1$-$C_8$-alkoxy is $C_1$-$C_4$-alkoxy.

"$C_1$-$C_8$-haloalkoxy" as used herein denotes $C_1$-$C_4$-alkoxy as hereinbefore defined substituted by one or more halogen atoms, preferably one, two or three halogen atoms. Preferably "$C_1$-$C_8$-haloalkoxy" is "$C_1$-$C_4$-haloalkoxy".

"di($C_1$-$C_8$-alkyl)sulfamoyl" as used herein denotes —$SO_2$—$NH_2$ where the nitrogen atom is substituted at two positions by $C_1$-$C_8$-alkyl as hereinbefore defined, which may be the same or different. Preferably di($C_1$-$C_8$-alkyl)sulfamoyl is —$SO_2$—$N(CH_3)_2$.

"Halo" or "halogen" as used herein denotes a element belonging to group 17 (formerly group VII) of the Periodic Table of Elements, which may be, for example, fluorine, chlorine, bromine or iodine. Preferably halo or halogen is fluorine, chlorine or bromine.

"Aminocarbonyl" as used herein denotes amino attached through the nitrogen atom to a carbonyl group.

"4- to 12-membered heterocyclic group containing at least one ring heteroatom selected from nitrogen, oxygen and sulphur" as used herein denotes a monoheterocyclic, biheterocyclic or triheterocyclic group, which may be saturated or unsaturated, that has 4 to 12 ring atoms. Monoheterocyclic groups include azetidinyl, tetrahydrofuranyl, furyl, pyrrolyl, pyrrolidinyl, pyrazolyl, imidazolyl, triazolyl, tetrazolyl, thienyl, thiazolyl, thiadiazolyl, isothiazolyl, oxadiazolyl, pyridinyl, oxazolyl, isoxazolyl, piperidinyl, pyridinyl, pyrazinyl, pyridazinyl, pyrimidinyl, piperazinyl, morpholinyl, triazinyl, oxazinyl, thiazolyl or tetrahydropyranyl. Biheterocyclic groups include thienothienyl, benzazolyl, benzothienyl, benzimidazolyl, benzodioxinyl, indazolyl, benzothiazolyl, imidazopyridinyl and naphthyridinyl. Preferred 4- to 12-membered heterocyclic groups include azetidinyl, tetrahydrofuranyl, furyl, pyrrolyl, pyrazolyl, triazolyl, thienyl, thiazolyl, thiadiazolyl, oxazolyl, isoxazolyl, tetrahydropyranyl, piperidinyl, pyridinyl, pyrazinyl, pyrimidinyl, thienothienyl, benzazolyl, benzothienyl, benzimidazolyl, benzodioxinyl, indazolyl and benzothiazolyl, imidazopyridinyl, naphthyridinyl. The 4- to 12-membered heterocyclic group can be unsubstituted or substituted at one or more positions, e.g. 1, 2 or 3 positions, by any one or any combination of substituents. Preferred substituents include halo (e.g. fluoro, chloro or bromo), cyano, oxo, hydroxy, carboxy, nitro, $C_1$-$C_8$-alkyl (e.g. methyl or ethyl), halo-$C_1$-$C_8$-alkyl (e.g. trifluoromethyl), $C_1$-$C_8$-alkylcarbonyl, di($C_1$-$C_8$-alkyl)sulfamoyl and $C_1$-$C_8$-alkoxy optionally substituted by aminocarbonyl. Especially preferred substituents include halo, oxo, $C_1$-$C_4$-alkyl and $C_1$-$C_4$-alkylcarbonyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

In a second aspect the invention provides compounds of formula I

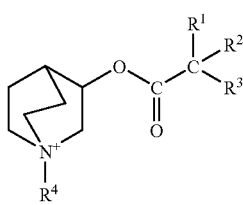

in salt or zwitterionic form wherein
$R^1$ and $R^3$ are each independently a $C_3$-$C_{15}$-carbocyclic group or a 4- to 12-membered heterocyclic group having at least one ring heteroatom selected from nitrogen, oxygen and sulphur,
or —$CR^1R^2R^3$ together form a group of formula

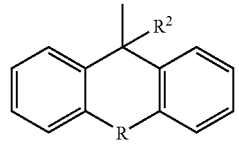

where R is a bond, —O—, —S—, —$CH_2$—, —CH=CH—, —$CH_1$—$CH_2$—, amino or —$N(CH_3)$—;
$R^2$ is hydrogen, halo, hydroxy, $C_1$-$C_8$-alkoxy or $C_1$-$C_8$-alkyl optionally substituted by hydroxy;
$R^4$ is $C_1$-$C_8$-alkyl substituted by —$NHR^5$, —$NR^5$—CO—$R^6$, —$NR^5$—CO—NH—$R^7$, —$NR^5$—$SO_2$—$R^8$, —CO—$NR^9R^{10}$, —$OR^{11}$, —O—CO—$NHR^{12}$, —O—CO—$R^{13}$ or —CO—O—$R^{14}$,
or $R^4$ is $C_3$-$C_{10}$-alkynyl optionally substituted by a $C_3$-$C_{15}$-carbocyclic group or a 4- to 12-membered heterocyclic group having at least one ring heteroatom selected from nitrogen, oxygen and sulphur;
$R^5$ is hydrogen or $C_1$-$C_8$-alkyl;
$R^6$ is $C_1$-$C_8$-alkyl, $C_2$-$C_8$-alkenyl, $C_2$-$C_{10}$-alkynyl or $C_1$-$C_8$-alkoxy in each case optionally substituted by a $C_3$-$C_{15}$-carbocyclic group or a 4- to 12-membered heterocyclic group having at least one ring heteroatom selected from nitrogen, oxygen and sulphur,
or $R^6$ is a $C_3$-$C_{15}$-carbocyclic group or a 4- to 12-membered heterocyclic group having at least one ring heteroatom selected from nitrogen, oxygen and sulphur;
$R^7$ is a $C_3$-$C_{15}$-carbocyclic group;
$R^8$ is a $C_3$-$C_{15}$-carbocyclic group;
$R^9$ is hydrogen or $C_1$-$C_8$-alkyl;
$R^{10}$ is hydrogen, $C_1$-$C_8$-alkyl optionally substituted by cyano, amino, nitro, carboxy, $C_1$-$C_8$-alkoxy, a $C_3$-$C_{15}$-carbocyclic group, or by a 4- to 12-membered heterocyclic group having at least one ring heteroatom selected from nitrogen, oxygen and sulphur,
or $R^{10}$ is a $C_3$-$C_{15}$-carbocyclic group or a 4- to 12-membered heterocyclic group having at least one ring heteroatom selected from nitrogen, oxygen and sulphur;
$R^{11}$ is hydrogen, $C_1$-$C_8$-alkyl, $C_1$-$C_8$-alkyl-$C_1$-$C_8$-alkoxy or $C_1$-$C_8$-alkyl-O—$R^{15}$;
$R^{12}$ is a $C_3$-$C_{15}$-carbocyclic group;
$R^{13}$ is $C_1$-$C_8$-alkyl or a $C_3$-$C_{15}$-carbocyclic group;
$R^{14}$ is hydrogen, a $C_3$-$C_{15}$-carbocyclic group, or $C_1$-$C_8$-alkyl optionally substituted by a $C_3$-$C_{15}$-carbocyclic group; and
$R^{15}$ is a $C_3$-$C_{15}$-carbocyclic group.

In a third aspect the invention provides compounds of formula I

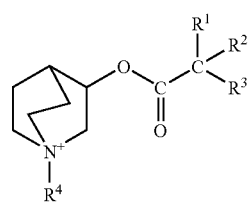

in salt or zwitterionic form wherein $R^1$ and $R^3$ are each independently a $C_3$-$C_{15}$-carbocyclic group or a 5- to 12-membered heterocyclic group having at least one ring heteroatom selected from nitrogen, oxygen and sulphur, or —$CR^1R^2R^3$ together form a group of formula

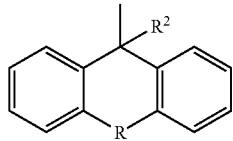

where R is a bond, —O—, —S—, —$CH_2$—, —CH=CH—, —$CH_2$—$CH_2$—, amino or —N($CH_3$)—;

$R^2$ is hydrogen, halo, hydroxy, $C_1$-$C_8$-alkoxy or $C_1$-$C_8$-alkyl optionally substituted by hydroxy;

$R^4$ is $C_1$-$C_8$-alkyl substituted by —$NHR^5$, —$NR^5$—CO—$R^6$, —$NR^5$—CO—NH—$R^7$, —$NR^5$—$SO_2$—$R^8$, —CO—$NR^9R^{10}$, —$OR^{11}$, —O—CO—$NHR^{12}$, —O—CO—$R^{13}$ or —CO—O—$R^{14}$, or $R^4$ is $C_3$-$C_{10}$-alkynyl optionally substituted by a $C_3$-$C_{15}$-carbocyclic group or a 5- to 12-membered heterocyclic group having at least one ring heteroatom selected from nitrogen, oxygen and sulphur;

$R^5$ is hydrogen or $C_1$-$C_8$-alkyl;

$R^6$ is $C_1$-$C_8$-alkyl or $C_1$-$C_8$-alkoxy in either case optionally substituted by a $C_3$-$C_{15}$-carbocyclic group or a 5- to 12-membered heterocyclic group having at least one ring heteroatom selected from nitrogen, oxygen and sulphur, or $R^6$ is a $C_3$-$C_{15}$-carbocyclic group or a 5- to 12-membered heterocyclic group having at least one ring heteroatom selected from nitrogen, oxygen and sulphur;

$R^7$ is a $C_3$-$C_{15}$-carbocyclic group;

$R^8$ is a $C_3$-$C_{15}$-carbocyclic group;

$R^9$ is hydrogen or $C_1$-$C_8$-alkyl;

$R^{10}$ is hydrogen, $C_1$-$C_8$-alkyl optionally substituted by cyano, amino, nitro, carboxy, $C_1$-$C_8$-alkoxy, a $C_3$-$C_{15}$-carbocyclic group, or by a 5- to 12-membered heterocyclic group having at least one ring heteroatom selected from nitrogen, oxygen and sulphur, or $R^{10}$ is a $C_3$-$C_{15}$-carbocyclic group or a 5- to 12-membered heterocyclic group having at least one ring heteroatom selected from nitrogen, oxygen and sulphur;

$R^{11}$ is hydrogen, $C_1$-$C_8$-alkyl, $C_1$-$C_8$-alkyl-$C_1$-$C_8$-alkoxy or $C_1$-$C_8$-alkyl-O—$R^{15}$;

$R^{12}$ is a $C_3$-$C_{15}$-carbocyclic group;

$R^{13}$ is $C_1$-$C_8$-alkyl or a $C_3$-$C_{15}$-carbocyclic group;

$R^{14}$ is hydrogen, $C_1$-$C_8$-alkyl or a $C_3$-$C_{15}$-carbocyclic group; and $R^{15}$ is a $C_3$-$C_{15}$-carbocyclic group.

Preferred compounds include those of formula I in salt or zwitterionic form, where $R^1$ and $R^3$ are each independently a $C_3$-$C_{15}$-carbocyclic group or a 4- to 12-membered heterocyclic group having at least one ring heteroatom selected from nitrogen, oxygen and sulphur;

$R^2$ is halo or hydroxy;

$R^4$ is $C_1$-$C_8$-alkyl substituted by —$NHR^5$, —$NR^5$—CO—$R^6$, —$NR^5$—CO—NH—$R^7$, —$NR^5$—$SO_2$—$R^8$, —CO—$NR^9R^{10}$, —O—CO—NH—$R^{12}$, —O—CO—$R^{13}$ or —CO—O—$R^{14}$, or $R^4$ is $C_3$-$C_{10}$-alkynyl optionally substituted by a $C_3$-$C_{15}$-carbocyclic group or a 4- to 12-membered heterocyclic group having at least one ring heteroatom selected from nitrogen, oxygen and sulphur;

$R^5$ is hydrogen or $C_1$-$C_8$-alkyl;

$R^6$ is $C_1$-$C_8$-alkyl, $C_2$-$C_{10}$-alkynyl or $C_1$-$C_8$-alkoxy in each case optionally substituted by a $C_3$-$C_{15}$-carbocyclic group or a 4- to 12-membered heterocyclic group having at least one ring heteroatom selected from nitrogen, oxygen and sulphur, or $R^6$ is a $C_3$-$C_{15}$-carbocyclic group or a 4- to 12-membered heterocyclic group having at least one ring heteroatom selected from nitrogen, oxygen and sulphur;

$R^7$ is a $C_3$-$C_{15}$-carbocyclic group;

$R^8$ is a $C_3$-$C_{15}$-carbocyclic group;

$R^9$ is hydrogen or $C_1$-$C_8$-alkyl;

$R^{10}$ is $C_1$-$C_8$-alkyl optionally substituted by cyano, $C_1$-$C_8$-alkoxy, a $C_3$-$C_{15}$-carbocyclic group or by a 4- to 12-membered heterocyclic group having at least one ring heteroatom selected from nitrogen, oxygen and sulphur, or $R^{10}$ is a $C_3$-$C_{15}$-carbocyclic group or a 4- to 12-membered heterocyclic group having at least one ring heteroatom selected from nitrogen, oxygen and sulphur;

$R^{12}$ is a $C_3$-$C_{15}$-carbocyclic group;

$R^{13}$ is $C_1$-$C_8$-alkyl; and $R^{14}$ is hydrogen, a $C_3$-$C_{15}$-carbocyclic group, $C_1$-$C_8$-alkenyl, or $C_1$-$C_8$-alkyl optionally substituted by a $C_3$-$C_{15}$-carbocyclic group.

Preferred compounds include those of formula I in salt or zwitterionic form, where $R^1$ and $R^3$ are each independently a $C_3$-$C_{15}$-carbocyclic group or a 4- to 12-membered heterocyclic group having at least one ring heteroatom selected from nitrogen, oxygen and sulphur;

$R^2$ is halo or hydroxy;

$R^4$ is $C_1$-$C_8$-alkyl substituted by —$NHR^5$, —$NR^5$—CO—$R^6$, —$NR^5$—CO—NH—$R^7$, —$NR^5$—$SO_2$—$R^8$, —CO—$NR^9R^{10}$, —O—CO—NH—$R^{12}$, —O—CO—$R^{13}$ or —CO—O—$R^{14}$, or $R^4$ is $C_3$-$C_{10}$-alkynyl optionally substituted by a $C_3$-$C_{15}$-carbocyclic group or a 4- to 12-membered heterocyclic group having at least one ring heteroatom selected from nitrogen, oxygen and sulphur;

$R^5$ is hydrogen or $C_1$-$C_8$-alkyl;

$R^6$ is $C_1$-$C_8$-alkyl, $C_1$-$C_{10}$-alkynyl or $C_1$-$C_8$-alkoxy in each case optionally substituted by a $C_3$-$C_{15}$-carbocyclic group or a 4- to 12-membered heterocyclic group having at least one ring heteroatom selected from nitrogen, oxygen and sulphur, or $R^6$ is a $C_3$-$C_{15}$-carbocyclic group or a 4- to 12-membered heterocyclic group having at least one ring heteroatom selected from nitrogen, oxygen and sulphur;

$R^7$ is a $C_3$-$C_{15}$-carbocyclic group;

$R^8$ is a $C_3$-$C_{15}$-carbocyclic group;

$R^9$ is hydrogen or $C_1$-$C_8$-alkyl;

$R^{10}$ is $C_1$-$C_8$-alkyl optionally substituted by cyano, $C_1$-$C_8$-alkoxy, a $C_3$-$C_{15}$-carbocyclic group or by a 4- to 12-membered heterocyclic group having at least one ring heteroatom selected from nitrogen, oxygen and sulphur, or $R^{10}$ is a $C_3$-$C_{15}$-carbocyclic group or a 4- to 12-membered heterocyclic group having at least one ring heteroatom selected from nitrogen, oxygen and sulphur;

$R^{12}$ is a $C_3$-$C_{15}$-carbocyclic group;

$R^{13}$ is $C_1$-$C_8$-alkyl; and $R^{14}$ is hydrogen, a $C_1$-$C_8$-carbocyclic group or $C_1$-$C_8$-alkyl optionally substituted by a $C_3$-$C_{15}$-carbocyclic group.

Preferred compounds also include those of formula I in salt or zwitterionic form, where $R^1$ and $R^3$ are each independently a $C_3$-$C_{15}$-carbocyclic group or a 5- to 12-membered heterocyclic group having at least one ring heteroatom selected from nitrogen, oxygen and sulphur;

$R^2$ is halo or hydroxy;

$R^4$ is $C_1$-$C_8$-alkyl substituted by —NHR$^5$, —NR$^5$—CO—R$^6$, —NR$^5$—CO—NH—R$^7$, —NR$^5$—SO$_2$—R$^8$, —CO—NR$^9$R$^{10}$, —O—CO—NH—R$^{12}$, —O—CO—R$^{13}$ or —CO—O—R$^{14}$, or $R^4$ is $C_3$-$C_{10}$-alkynyl optionally substituted by a $C_3$-$C_{15}$-carbocyclic group or a 5- to 12-membered heterocyclic group having at least one ring heteroatom selected from nitrogen, oxygen and sulphur;

$R^5$ is hydrogen;

$R^6$ is $C_1$-$C_8$-alkyl or $C_1$-$C_8$-alkoxy in either case optionally substituted by a $C_3$-$C_{15}$-carbocyclic group or a 5- to 12-membered heterocyclic group having at least one ring heteroatom selected from nitrogen, oxygen and sulphur, or $R^6$ is a $C_3$-$C_{15}$-carbocyclic group or a 5- to 12-membered heterocyclic group having at least one ring heteroatom selected from nitrogen, oxygen and sulphur;

$R^7$ is a $C_3$-$C_{15}$-carbocyclic group;

$R^8$ is a $C_3$-$C_{15}$-carbocyclic group;

$R^9$ is hydrogen or $C_1$-$C_8$-alkyl;

$R^{10}$ is $C_1$-$C_8$-alkyl optionally substituted by cyano, $C_1$-$C_8$-alkoxy, a $C_3$-$C_{15}$-carbocyclic group or by a 5- to 12-membered heterocyclic group having at least one ring heteroatom selected from nitrogen, oxygen and sulphur, or $R^{10}$ is a $C_3$-$C_{15}$-carbocyclic group or a 5- to 12-membered heterocyclic group having at least one ring heteroatom selected from nitrogen, oxygen and sulphur;

$R^{12}$ is a $C_3$-$C_{15}$-carbocyclic group;

$R^{13}$ is $C_1$-$C_8$-alkyl; and $R^{14}$ is hydrogen, $C_1$-$C_8$-alkyl or a $C_3$-$C_{15}$-carbocyclic group.

Especially preferred compounds include chose of formula I in salt or zwitterionic form where $R^1$ and $R^3$ are each independently a $C_6$-$C_{10}$-carbocyclic aromatic group or a 4- to 12-membered heterocyclic group having at least one ring heteroatom selected from nitrogen, oxygen and sulphur;

$R^2$ is halo or hydroxy;

$R^4$ is $C_1$-$C_8$-alkyl substituted by —NHR$^5$, —NR$^5$—CO—R$^6$, —NR$^5$—CO—NH—R$^7$, —NR$^5$—SO$_2$—R$^8$, —CO—NR$^9$R$^{10}$, —O—CO—NH—R$^{12}$, —O—CO—R$^{13}$ or —CO—O—R$^{14}$, or $R^4$ is $C_3$-$C_8$-alkynyl optionally substituted by a $C_1$-$C_{10}$-carbocyclic group or a 4- to 10-membered heterocyclic group having at least one ring heteroatom selected from nitrogen, oxygen and sulphur;

$R^5$ is hydrogen or $C_1$-$C_4$-alkyl;

$R^6$ is $C_1$-$C_4$-alkyl, $C_2$-$C_8$-alkynyl or $C_1$-$C_4$-alkoxy in each case optionally substituted by a $C_3$-$C_{10}$-carbocyclic group or a 4- to 12-membered heterocyclic group having at least one ring heteroatom selected from nitrogen, oxygen and sulphur, or $R^6$ is a $C_3$-$C_{10}$-carbocyclic group or a 4- to 10-membered heterocyclic group having at least one ring heteroatom selected from nitrogen, oxygen and sulphur;

$R^7$ is a $C_1$-$C_{10}$-carbocyclic group;

$R^8$ is a $C_3$-$C_{10}$-carbocyclic group;

$R^9$ is hydrogen or $C_1$-$C_4$-alkyl;

$R^{10}$ is $C_1$-$C_4$-alkyl optionally substituted by cyano, $C_1$-$C_4$-alkoxy, a $C_3$-$C_{10}$-carbocyclic group or by a 4- to 10-membered heterocyclic group having at least one ring heteroatom selected from nitrogen, oxygen and sulphur, or $R^{10}$ is a $C_3$-$C_{10}$-carbocyclic group or a 4- to 10-membered heterocyclic group having at least one ring heteroatom selected from nitrogen, oxygen and sulphur;

$R^{12}$ is a $C_3$-$C_{10}$-carbocyclic group;

$R^{13}$ is $C_1$-$C_4$-alkyl; and $R^{14}$ is hydrogen, a $C_3$-$C_{10}$-carbocyclic group, $C_1$-$C_4$-alkenyl, or $C_1$-$C_4$-alkyl optionally substituted by a $C_3$-$C_{10}$-carbocyclic group.

Especially preferred compounds include those of formula I in salt or zwitterionic form where $R^1$ and $R^3$ are each independently a $C_6$-$C_{10}$-carbocyclic aromatic group or a 4- to 12-membered heterocyclic group having at least one ring heteroatom selected from nitrogen, oxygen and sulphur;

$R^2$ is halo or hydroxy;

$R^4$ is $C_1$-$C_8$-alkyl substituted by —NHR$^5$, —NR$^5$—CO—R$^6$, —NR$^5$—CO—NH—R$^7$, —NR$^5$—SO$_2$—R$^8$, —CO—NR$^9$R$^{10}$, —O—CO—NH—R$^{12}$, —O—CO—R$^{13}$ or —CO—O—R$^{14}$, or $R^4$ is $C_3$-$C_8$-alkynyl optionally substituted by a $C_3$-$C_{10}$-carbocyclic group or a 4- to 10-membered heterocyclic group having at least one ring heteroatom selected from nitrogen, oxygen and sulphur;

$R^5$ is hydrogen or $C_1$-$C_4$-alkyl;

$R^6$ is $C_1$-$C_4$-alkyl, $C_2$-$C_8$-alkynyl or $C_1$-$C_4$-alkoxy in each case optionally substituted by a $C_3$-$C_{10}$-carbocyclic group or a 4- to 12-membered heterocyclic group having at least one ring heteroatom selected from nitrogen, oxygen and sulphur, or $R^6$ is a $C_3$-$C_{10}$-carbocyclic group or a 4- to 10-membered heterocyclic group having at least one ring heteroatom selected from nitrogen, oxygen and sulphur;

$R^7$ is a $C_3$-$C_{10}$-carbocyclic group;

$R^8$ is a $C_3$-$C_{10}$-carbocyclic group;

$R^9$ is hydrogen or $C_1$-$C_4$-alkyl;

$R^{10}$ is $C_1$-$C_4$-alkyl optionally substituted by cyano, $C_1$-$C_4$-alkoxy, a $C_3$-$C_{10}$-carbocyclic group or by a 4- to 10-membered heterocyclic group having at least one ring heteroatom selected from nitrogen, oxygen and sulphur, or $R^{10}$ is a $C_3$-$C_{10}$-carbocyclic group or a 4- to 10-membered heterocyclic group having at least one ring heteroatom selected from nitrogen, oxygen and sulphur;

$R^{12}$ is a $C_1$-$C_4$-carbocyclic group;

$R^{13}$ is $C_1$-$C_4$-alkyl; and $R^{14}$ is hydrogen, a $C_3$-$C_{10}$-carbocyclic group or $C_1$-$C_4$-alkyl optionally substituted by a $C_3$-$C_{10}$-carbocyclic group.

Especially preferred compounds also include those of formula I in salt or zwitterionic form where $R^1$ and $R^3$ are each independently a $C_6$-$C_{10}$-carbocyclic aromatic group or a 5- to 12-membered heterocyclic group having at least one ring heteroatom selected from nitrogen, oxygen and sulphur;

$R^2$ is halo or hydroxy;

$R^4$ is $C_1$-$C_8$-alkyl substituted by —NHR$^5$, —NR$^5$—CO—R$^6$, —NR$^5$—CO—NH—R$^7$, —NR$^5$—SO$_2$—R$^8$, —CO—NR$^9$R$^{10}$, —O—CO—NH—R$^{12}$, —O—CO—R$^{13}$ or —CO—O—R$^{14}$, or $R^4$ is $C_3$-$C_8$-alkynyl optionally substituted by a $C_3$-$C_{10}$-carbocyclic group or a 5- to 10-membered heterocyclic group having at least one ring heteroatom selected from nitrogen, oxygen and sulphur;

$R^5$ is hydrogen;

$R^6$ is $C_1$-$C_4$-alkyl or $C_1$-$C_4$-alkoxy in either case optionally substituted by a $C_3$-$C_{10}$-carbocyclic group or a 5- to 12-membered heterocyclic group having at least one ring heteroatom selected from nitrogen, oxygen and sulphur, or $R^6$ is a $C_3$-$C_{10}$-carbocyclic group or a 5- to 10-membered heterocyclic group having at least one ring heteroatom selected from nitrogen, oxygen and sulphur;

$R^7$ is a $C_3$-$C_{10}$-carbocyclic group;

$R^8$ is a $C_3$-$C_{10}$-carbocyclic group;

$R^9$ is hydrogen or $C_1$-$C_4$-alkyl;

$R^{10}$ is $C_1$-$C_4$-alkyl optionally substituted by cyano, $C_1$-$C_4$-alkoxy, a $C_3$-$C_{10}$-carbocyclic group or by a 5- to 10-membered heterocyclic group having at least one ring heteroatom selected from nitrogen, oxygen and sulphur, or $R^{10}$ is a $C_3$-$C_{10}$-carbocyclic group or a 5- to 10-membered heterocyclic group having at least one ring heteroatom selected from nitrogen, oxygen and sulphur;

$R^{12}$ is a $C_3$-$C_{10}$-carbocyclic group;

$R^{13}$ is $C_1$-$C_4$-alkyl; and $R^{14}$ is hydrogen, $C_1$-$C_4$-alkyl or a $C_3$-$C_{10}$-carbocyclic group.

The compounds of formula I are quaternary ammonium salts. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic adds, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures. Compounds of formula I that contain acidic, e.g. carboxyl, groups may also exist as zwitterions with the quaternary ammonium centre.

The compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

Specific especially preferred compounds of the invention are those described hereinafter in the Examples. These have R stereochemistry at the 3 position of the quinuclidine.

The invention also provides a process for the preparation of compounds of formula I which comprises (i) (A) reacting a compound of compound of formula II

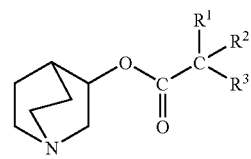

or a protected form thereof where $R^1$, $R^2$ and $R^3$ are as hereinbefore defined, with a compound of formula III

$$R^4-X$$

where $R^4$ is as hereinbefore defined and X is chloro, bromo or iodo;

(B) for the preparation of compounds of formula I where $R^4$ is $C_1$-$C_8$-alkyl substituted by —$NR^5$—CO—$R^6$ where $R^5$ and $R^6$ are as hereinbefore defined, reacting a compound of formula IV

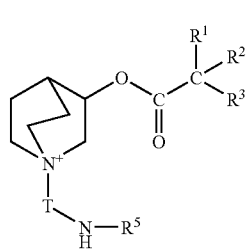

or a protected form thereof where $R^1$, $R^2$, $R^3$ and $R^5$ are as hereinbefore defined, optionally in the presence of a coupling agent, and T denotes $C_1$-$C_8$-alkylene, with a compound of formula V

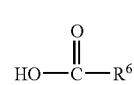

where $R^6$ is as hereinbefore defined or an amide-forming derivative thereof such as an acid halide;

(C) for the preparation of compounds of formula I where $R^4$ is $C_1$-$C_8$-alkyl substituted by —$NR^5$—CO—NH—$R^7$ where $R^5$ and $R^7$ are as hereinbefore defined, reacting a compound of formula IV or a protected form thereof where $R^1$, $R^2$, $R^3$ and $R^5$ are as hereinbefore defined and T denotes $C_1$-$C_8$-alkylene, with a compound of formula VI

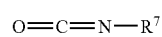

$$O=C=N-R^7$$

where $R^7$ is as hereinbefore defined;

(D) for the preparation of compounds of formula I where $R^4$ is $C_1$-$C_8$-alkyl substituted by —$NR^5$—$SO_2$—

$R^8$ where $R^5$ and $R^8$ are as hereinbefore defined, reacting a compound of formula IV or a protected form thereof where $R^1$, $R^2$, and $R^3$ are as hereinbefore defined and T denotes $C_1$-$C_8$-alkylene, with a compound of formula VII

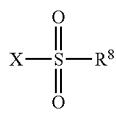
VII where $R^8$ is as hereinbefore defined and X is halo; or (E) for the preparation of compounds of formula I where $R^4$ is $C_1$-$C_8$-alkyl substituted by —CO—NR$^9$R$^{10}$ where $R^9$ and $R^{10}$ are as hereinbefore defined, reacting a compound of formula VIII

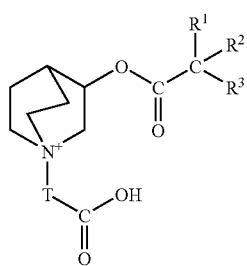
VIII or a protected form thereof where $R^1$, $R^2$, and $R^3$ are as hereinbefore defined and T denotes $C_1$-$C_8$-alkylene, optionally in the presence of a coupling agent, or an amide-forming derivative thereof such as an acid halide, with a compound of formula IX

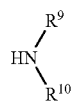
IX where $R^9$ and $R^{10}$ are as hereinbefore defined; and
(ii) recovering the product in salt or zwitterionic form.

Process variant (A) may be effected using known procedures for reacting quinuclidinol esters with halogenides or analogously as hereinafter described in the Examples. The reaction is conveniently carried out in water or an organic solvent, for example acetonitrile, dimethylformamide (DMF), dimethylsulphoxide (DMSO), ethyl acetate or chloroform. The reaction is carried out at a temperature between 20° C. to 120° C., conveniently between room temperature and 80° C.

Process variant (B) may be effected using known procedures for reacting amines with carboxylic acids or amide-forming derivatives thereof such as acid halides to give amides or analogously as hereinafter described in the Examples. The reaction between the carboxylic acid and the amine is conveniently carried out in an organic solvent, for example dimethylformamide (DMF), optionally in the presence of a coupling agent, for example O-(7-azabenzotriazol-1-yl)-N,N,—N',N'-tetramethyl-uronium hexafluorophosphate (HATU), and a base, for example diisopropylethylamine (DIPEA) or triethylamine. Suitable reaction temperatures are from 0° C. to 50° C., conveniently room temperature.

Process variant (C) may be effected using known procedures for reacting amines with isocyanates to give ureas or analogously as hereinafter described in the Examples. The reaction is conveniently carried out in an organic solvent, for example dimethylformamide (DMF), and preferably in the presence of a base, for example DIPEA. Suitable reaction temperatures are from −78° C. to 40° C., conveniently room temperature.

Process variant (D) may be effected using known procedures for reacting amines with sulfonylhalides to give sulfonamides or analogously as hereinafter described in the Examples. The reaction is conveniently carried out in an organic solvent, for example dimethylformamide (DMF), and preferably in the presence of a base, for example DIPEA. Suitable reaction temperatures are from 0° C. to 50° C., conveniently room temperature.

Process variant (E) may be effected using known procedures for reacting carboxylic acids or amide-forming derivatives thereof such as acid halides with amines to give amides or analogously as hereinafter described in the Examples. The reaction between the carboxylic acid and the amine is conveniently carried out in an organic solvent, for example dimethylsulfoxide (DMSO) or dimethylformamide (DMF), optionally in the presence of a coupling agent, for example HATU, and preferably in the presence of a base, for example DIPEA. Suitable reaction temperatures are from 0° C. to 50° C., conveniently room temperature.

Compounds of formula II are known or may be prepared by known procedures such as those disclosed in W. J. Rzeszotarski et al, *J. Med. Chem.* 1988, 31, 1463, international patent publication WO 01/04118 and United States patent specification U.S. Pat. No. 3,833,592.

Compounds of formula III are known or may be prepared by known procedures.

Compounds of formula IV may be prepared by deprotecting a compound of formula X

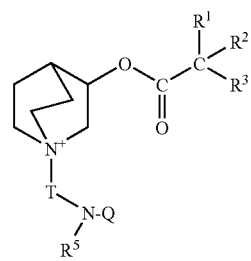
X where $R^1$, $R^2$, $R^3$ and $R^5$ are as hereinbefore defined, Q is an amine protecting group and T denotes $C_1$-$C_8$-alkylene, e.g. when Q is t-butyloxycarbonyl by treatment with a strong acid, e.g. hydrochloric acid or hydrobromic acid, which is conveniently carried out in an organic solvent, for example dioxan (1,4-dioxycyclohexane), and suitable reaction temperatures are from 0° C. to 60° C., conveniently room temperature.

Compounds of formula V, VI and VII are known or may be prepared by known procedures.

Compounds of formula VIII may be prepared by cleavage of a corresponding ester of formula XI

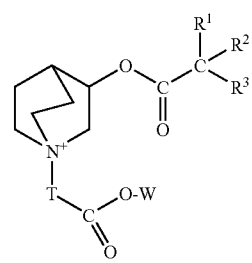
XI where $R^1$, $R^2$, and $R^3$ are as hereinbefore defined, T denotes $C_1$-$C_8$-alkylene and W denotes a group that is readily replaceable by hydrogen. For example when W is t-butyl the compound may be reacted with an anhydrous strong acid, e.g. hydrochloric acid, hydrobromic acid or trifluoroacetic acid, which is conveniently carried out in an organic solvent, for example dioxane, and suitable reaction temperatures are from −20° C. to 40° C., conveniently room temperature.

Compounds of formula IX are known or may be prepared by known procedures.

Compounds of formula X may be prepared by reacting a compound of formula II where $R^1$, $R^2$ and $R^3$ are as hereinbefore defined, with a compound of formula XII

XII where $R^5$ is as hereinbefore defined, Q is an amine protecting group e.g. t-butyloxycarbonyl, $X^1$ is chloro, bromo or iodo and T denotes $C_1$-$C_8$-alkylene. The reaction is conveniently carried out in an organic solvent, for example DMF. Suitable reaction temperatures are from 40° C. to 120° C., conveniently between room temperature and 80° C.

Compounds of formula XI may be prepared by reacting a compound of formula II where $R^1$, $R^2$ and $R^3$ are as hereinbefore defined, with a compound of formula XIII

XIII where T denotes $C_1$-$C_8$-alkylene, $X^2$ is chloro, bromo or iodo and W is a group that is readily replaceable by hydrogen. For example when W is t-butyl the reaction is conveniently carried out in an organic solvent, (or example DMF. Suitable reaction temperatures are from 0° C. to 120° C., conveniently between room temperature and 60° C.

Compounds of formula XII and XIII are known or may be prepared by known procedures.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula I are quaternary ammonium salts and may be converted between different salt forms using ion exchange chromatography. The compounds can be obtained in the form of hydrates or solvates containing a solvent used for crystallization. Compounds of formula I can be recovered from reaction mixtures and purified using known methods. Isomers, such as enantiomers, may be obtained in a conventional manner, e.g. by fractional crystallization, chiral phase chromatography or asymmetric synthesis from correspondingly asymmetrically substituted, e.g. optically active, suiting materials.

Compounds of formula I in pharmaceutically acceptable salt or zwitterionic form, hereinafter referred to alternatively as agents of the invention, are useful as pharmaceuticals. Accordingly the invention also provides a compound of formula I in pharmaceutically acceptable salt or zwitterionic form for use as a pharmaceutical. The agents of the invention act as muscarinic antagonists, particularly muscarinic M3 receptor antagonists, thereby inhibiting acetylcholine-induced contraction of smooth muscle in e.g. respiratory tract, digestive tract and urinary systems.

The affinity (Ki) of agents of the invention at the human muscarinic acetylcholine M3 receptor can be determined in a competitive filtration binding assay with the radio-labelled antagonist [$^3$H] n-methyl scopolamine methyl chloride (NMS): Membranes prepared from CHO cells stably transfected with human M3 receptor at 10 μg protein/well are incubated with serial dilutions of the agents of the invention, [$^3$H]NMS (0.25 nM) and assay buffer (20 mM HEPES, 1 mM $MgCl_2$ at pH 7.4) for 17 hours at room temperature. The assay is carried out in a 250 μL final volume, in the presence of a final dimethyl sulfoxide concentration of 1%. Total binding of [$^3$H]NMS is determined in the absence of the agents of the invention with a corresponding substituted volume of assay buffer. Non-specific binding of [$^3$H] NMS is determined in the presence of 300 nM ipratropium bromide. Following the incubation period, the membranes are harvested onto a Unifilter™ GF/B filter plate containing 0.05% polyethyleneimine, using a Brandel™ filtration harvester 9600. Filter plates are dried for two hours at 35° C. before the addition of Microscint™ 'O' cocktail, and read on a Packard Topcount™ scintillator using a $^3$H-Scintillation protocol. All IC50s are calculated with the aid of XL-Fit graph package and $K_i$ values derived using the Cheng-Prusoff correction (Cheng Y., Prusoff W. H. (1973) Biochem. Pharmacol 22 3099-3109).

The compounds of the Examples herein below generally have Ki values below 1 μM in the above assay. For instance, the compounds of Examples 17, 34, 52, 54, 71, 76, 96, 114, 138, 159, 170, 190, 209, 221, 242 and 244 have M3 $K_i$ values of 0.0144, 0.0023, 0.0019, 0.0001, 0.0005, 0.0011, 0.0046, 0.0002, 0.0022, 0.0007, 0.0007, 0.0007, 0.0010, 0.0013, 0.0003 and 0.0003 μM respectively.

Having regard to their inhibition of acetyl choline binding to M3 muscarinic receptors, agents of the invention are useful in the treatment of conditions mediated by the muscarinic M3 receptor, particularly those associated with increased parasympathetic tone leading to, for example, excessive glandular secretion or smooth muscle contraction. Treatment in accordance with the invention may be symptomatic or prophylactic.

Having regard to their antimuscarinic activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163, Hammelmann et al, *Am. J. Respir. Crit. Care Med.*, 1997, 156, 766 and analogous models. The agents of the invention are therefore useful in the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with $β_2$ agonists such as tachycardia, tremor and restlessness, such agents accordingly being suitable for use in on demand (rescue) treatment as well as prophylactic treatment of obstructive or inflammatory airways diseases.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalcosis, ptilosis, siderosis, silicosis, tabacosis and byssinosis.

Having regard to their antimuscarinic activity, the agents of the invention are also useful in the treatment of a condition requiring relaxation of smooch muscle of the uterus, bladder or vascular system. They are thus useful for the prevention or alleviation of premature labour pains in pregnancy. They are also useful in the treatment of chronic and acute urticaria, psoriasis, allergic conjunctivitis, actinitis, rhinitis including allergic rhinitis, mastocytosis, urinary disorders such as urinary incontinence (particularly that caused by overactive bladder), pollakiuria, neurogenic or unstable bladder, cytospasm and chronic cystitis; gastrointestinal disorders such as irritable bowel syndrome, spastic colitis, diverticulitis and peptic ulceration; and cardiovascular disorders such as vagally induced sinus bradycardia, as well as in ophthalmic interventions.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as chose mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s). Accordingly the invention includes a combination of an agent of the invention as hereinbefore described with an anti-inflammatory, bronchodilatory, antihistamine, decongestant or anti-tussive drug substance, said agent of the invention and said drug substance being in the same or different pharmaceutical composition. Such anti-inflammatory drugs include steroids, for example glucocorticosteroids such as budesonide, beclamethasone, fluticasone, ciclesonide or mometasone, or steroids described in WO 02/88167, WO 02/12266, WO 02/100879 or WO 02/00679, especially those of Examples 3, 11, 14, 17, 19, 26, 34, 37, 39, 51, 60, 67, 72, 73, 90, 99 and 101, and non-steroidal steroid agonists such as those described in WO 00/00531, WO 02/10143, WO 03/082280, WO 03/082787, WO 03/104195, WO 04/005229; LTB4 antagonists such as those described in U.S. Pat. No. 5,451,700; LTD4 antagonists such as montelukast and zafirlukast; PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID™ CC-10004 (Celgene), KW-4490 (Kyowa Hakko Kogyo), WO 03/104204, WO 03/104205, WO 04/000814, WO 04/000839 and WO 04005258 (Merck), as well as those described in WO 98/18796 and WO 03/39544; A2a agonises such as chose described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and A2b antagonists such as those described in WO 02/42298.

The agents of the invention are useful in combination therapy with chemokine receptor antagonists, calcium channel blockers, alpha-adrenoceptor antagonists, dopamine agonists, endothelin antagonists, substance-P antagonists, 5-LO inhibitors, VLA-4 antagonists and theophylline.

The agents of the invention are also particularly useful as co-therapeutic agents for use in combination with beta-2 adrenoceptor agonists or corticosteroids. Suitable beta-2 adrenoceptor agonists include salbutamol, terbutaline, salmeterol and, especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

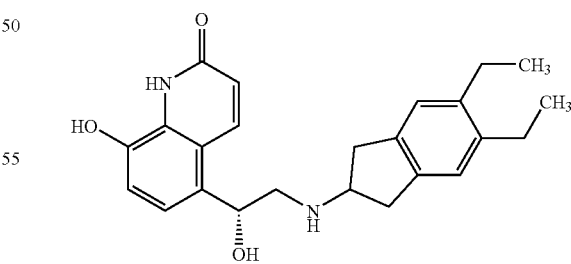

and pharmaceutically acceptable salts thereof, as well as compounds (in free or salt or solvate form) of formula I of WO 04/16601.

Co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and one or more of beta-2 adrenoceptor agonists, steroids, PDE4 inhibitors, A2a agonists, A2b agonists and LTD4 antagonists may be used, for example, in the treatment of asthma but particularly COPD.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising a compound of formula I in free form or in the form of a pharmaceutically acceptable salt or solvate thereof, optionally together with a pharmaceutically acceptable diluent or carrier thereof. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

Especially preferred compounds of formula I include compounds of formula XIV

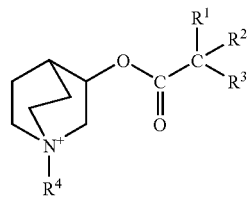

where $R^1$, $R^2$, $R^3$, and $R^4$ are as shown in Table 1 below, the method of preparation being described hereinafter. All compounds are quaternary ammonium salts. The table also shows mass spectrometry data.

TABLE 1

| Ex. | $R^1$ and $R^3$ | $R^4$ | $R^2$ | M/s M+ |
|---|---|---|---|---|
| 1 | phenyl | propyl-NH₂ | OH | 395.4 |
| 2 | phenyl | propyl-NHC(O)phenyl | OH | 499.4 |

TABLE 1-continued

| Ex. | R¹ and R³ | R⁴ | R² | M/s M+ |
|---|---|---|---|---|
| 3 | toluene (methylbenzene) | N-butyl naphthalene-2-carboxamide | OH | 549.5 |
| 4 | toluene | 4-cyano-N-butylbenzamide | OH | 524.5 |
| 5 | toluene | N-butyl-2,6-dimethylbenzamide | OH | 527.5 |
| 6 | toluene | N-butyl-[1,1'-biphenyl]-4-carboxamide | OH | 575.5 |
| 7 | toluene | N-butyl-4-(1H-pyrrol-1-yl)benzamide | OH | 564.5 |
| 8 | toluene | N-butyl-3-(methylsulfonyl)benzamide | OH | 577.5 |
| 9 | toluene | N-butylnicotinamide | OH | 500.4 |
| 10 | toluene | N-butyl-4-chlorobenzamide | OH | 533.4 |

TABLE 1-continued

| Ex. | R¹ and R³ | R⁴ | R² | M/s M+ |
|---|---|---|---|---|
| 11 | phenyl | N-butyl 3,5-dimethoxybenzamide | OH | 559.4 |
| 12 | phenyl | N-butyl 3-chlorobenzamide | OH | 533.4 |
| 13 | phenyl | N-butyl 4-ethylbenzamide | OH | 527.4 |
| 14 | phenyl | N-butyl 3-(trifluoromethyl)benzamide | OH | 567.4 |
| 15 | phenyl | N-butyl 4-(trifluoromethyl)benzamide | OH | 567.4 |
| 16 | phenyl | N-butyl 2-(trifluoromethyl)benzamide | OH | 567.4 |
| 17 | phenyl | N-butyl 3,4-dimethoxybenzamide | OH | 559.5 |
| 18 | phenyl | N-butyl 4-methoxybenzamide | OH | 529.4 |

TABLE 1-continued

| Ex. | R¹ and R³ | R⁴ | R² | M/s M+ |
|---|---|---|---|---|
| 19 | phenyl | N-butyl 2-methoxybenzamide | OH | 529.4 |
| 20 | phenyl | N-butyl 4-isopropoxybenzamide | OH | 557.5 |
| 21 | phenyl | N-butyl 2,4-dimethoxybenzamide | OH | 559.5 |
| 22 | phenyl | N-butyl 2,3-dimethoxybenzamide | OH | 559.5 |
| 23 | phenyl | N-butyl 2-cyanobenzamide | OH | 524.4 |
| 24 | phenyl | N-butyl 3-fluoro-4-methoxybenzamide | OH | 547.4 |
| 25 | phenyl | N-butyl 3-cyanobenzamide | OH | 524.4 |

TABLE 1-continued

| Ex. | R¹ and R³ | R⁴ | R² | M/s M+ |
|---|---|---|---|---|
| 26 | phenyl (CH₃) | N-butyl-3-methoxybenzamide | OH | 529.5 |
| 27 | phenyl (CH₃) | N-butylpyridine-2-carboxamide | OH | 500.4 |
| 28 | phenyl (CH₃) | N-butylpyridine-4-carboxamide | OH | 500.4 |
| 29 | phenyl (CH₃) | N-butyl-5-methylisoxazole-3-carboxamide | OH | 504.4 |
| 30 | phenyl (CH₃) | N-butylcyclohexanecarboxamide | OH | 505.7 |
| 31 | phenyl (CH₃) | N-butylcycloheptanecarboxamide | OH | 519.7 |
| 32 | phenyl (CH₃) | N-butylcyclopentanecarboxamide | OH | 491.7 |
| 33 | phenyl (CH₃) | N-butyl-3,3-dimethylbutanamide | OH | 493.7 |
| 34 | phenyl (CH₃) | N-butyl-2-phenylacetamide | OH | 513.7 |

TABLE 1-continued
| Ex. | R¹ and R³ | R⁴ | R² | M/s M+ |
|---|---|---|---|---|
| 35 | 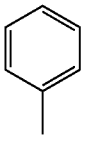 | 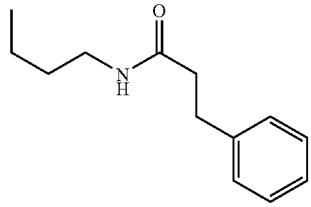 | OH | 527.7 |
| 36 | 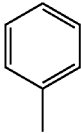 | 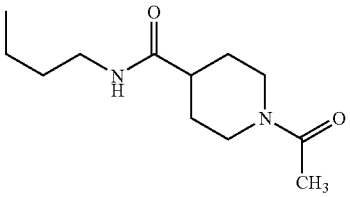 | OH | 548.7 |
| 37 | 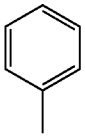 | 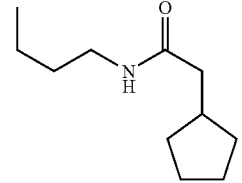 | OH | 505.7 |
| 38 | 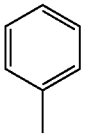 | 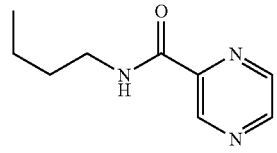 | OH | 501.6 |
| 39 | 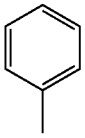 | 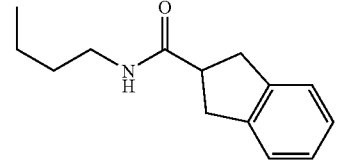 | OH | 539.7 |
| 40 | 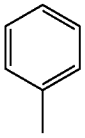 | 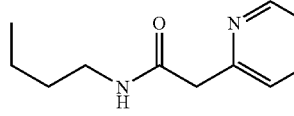 | OH | 514.7 |
| 41 | 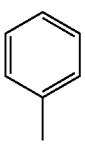 | 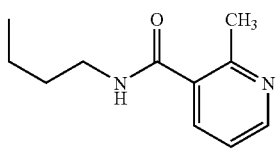 | OH | 514.7 |
| 42 | 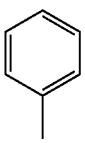 | 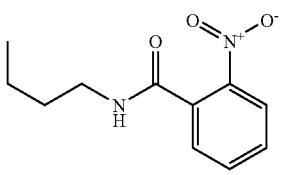 | OH | 544.6 |

TABLE 1-continued

| Ex. | R¹ and R³ | R⁴ | R² | M/s M+ |
|---|---|---|---|---|
| 43 | phenyl | N-butyl-2-chlorobenzamide | OH | 533.2 |
| 44 | phenyl | N-butyl-2-(methylsulfonyl)benzamide | OH | 577.2 |
| 45 | phenyl | N-butyl-3,5-dimethylbenzamide | OH | 527.7 |
| 46 | phenyl | N-butyl-isobutyramide | OH | 465.6 |
| 47 | phenyl | 1-butyl-3-phenylurea | OH | 514.4 |
| 48 | phenyl | 1-butyl-3-(4-butyl-2-methylphenyl)urea | OH | 584.3 |
| 49 | phenyl | N-propyl-4-methylbenzenesulfonamide | OH | 535.4 |
| 50 | phenyl | N-propylbenzamide | OH | 485.4 |
| 51 | phenyl | N-(5-fluorobenzo[d]thiazol-2-yl)propanamide | OH | 546.3 |

TABLE 1-continued
| Ex. | R¹ and R³ | R⁴ | R² | M/s M+ |
|---|---|---|---|---|
| 52 | 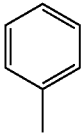 | 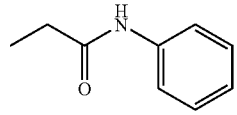 | OH | 471.4 |
| 53 | 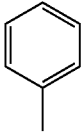 | 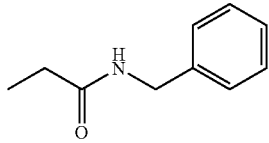 | OH | 485.4 |
| 54 | 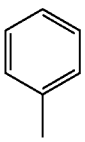 | 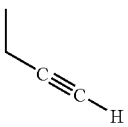 | OH | 376.3 |
| 55 | 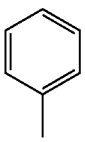 | 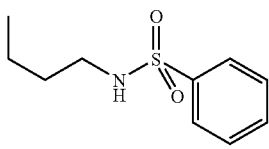 | OH | 535.0 |
| 56 | 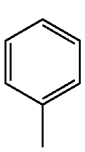 | 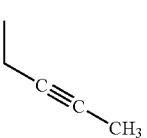 | OH | 390.3 |
| 57 | 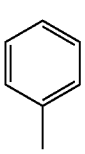 | 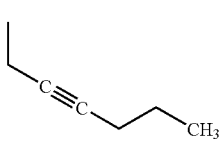 | OH | 418.2 |
| 58 |  | 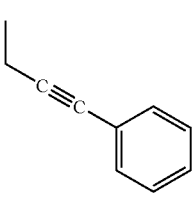 | OH | 452.2 |
| 59 | 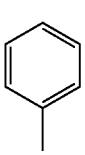 | 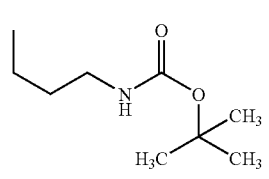 | OH | 495.4 |
| 60 | 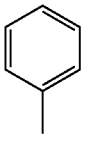 | 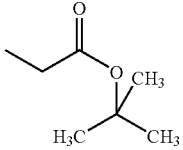 | OH | 452 |

TABLE 1-continued

| Ex. | R¹ and R³ | R⁴ | R² | M/s M+ |
|---|---|---|---|---|
| 61 | phenyl | propyl-NH-C(O)-O-C(CH₃)₃ (tert-butyl carbamate) | OH | 481 |
| 62 | phenyl | propanoic acid (CH₂CH₂COOH) | OH | 396 |
| 63 | phenyl | N-(5,6-diethyl-2,3-dihydro-1H-inden-2-yl)propanamide | OH | 567 |
| 64 | phenyl | hex-5-ynyl (CH₂CH₂CH₂CH₂C≡CH) | OH | 404.2 |
| 65 | phenyl | 2-(pent-2-yn-1-yl)isoindoline-1,3-dione with CH₃ branch | OH | 535.2 |
| 66 | phenyl | propyl N-cyclohexylcarbamate | OH | 507.4 |
| 67 | phenyl | 1-phenyl-3-propylurea | OH | 500.4 |
| 68 | phenyl | 1-cyclohexyl-3-propylurea | OH | 506.5 |
| 69 | phenyl | pent-2-ynyl (CH₂C≡C-CH₂CH₃) | OH | 404.3 |
| 70 | thiophen-2-yl | butyl N-tert-butoxycarbamate | OH | 507.3 |

TABLE 1-continued
| Ex. | R¹ and R³ | R⁴ | R² | M/s M+ |
|---|---|---|---|---|
| 71 | 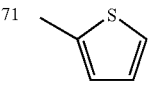 | 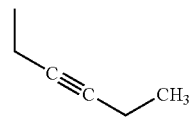 | OH | 416.3 |
| 72 | 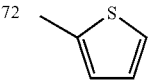 | 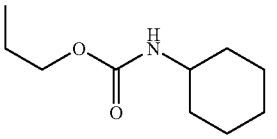 | OH | 519.4 |
| 73 | 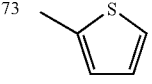 | 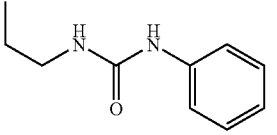 | OH | 512.3 |
| 74 | 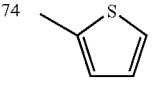 | 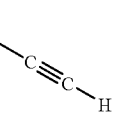 | OH | 388.2 |
| 75 | 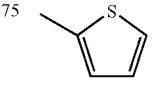 | 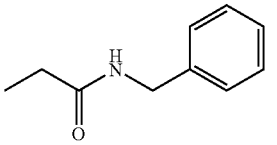 | OH | 497.1 |
| 76 | 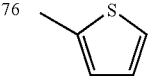 | 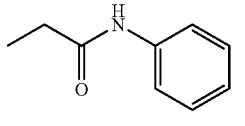 | OH | 483.3 |
| 77 | 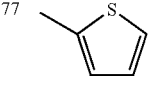 | 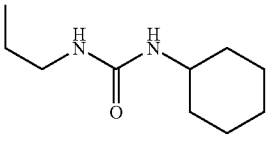 | OH | 518.4 |
| 78 | 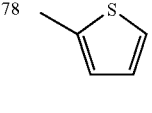 | 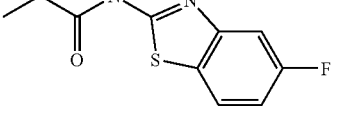 | OH | 558.3 |
| 79 | 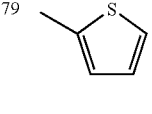 | 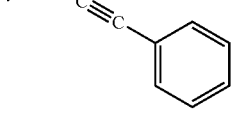 | OH | 464.7 |
| 80 | 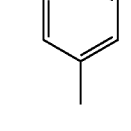 | 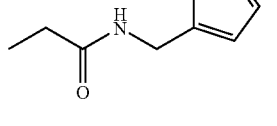 | OH | 475.2 |

TABLE 1-continued

| Ex. | R¹ and R³ | R⁴ | R² | M/s M+ |
|---|---|---|---|---|
| 81 | phenyl | propanamide-N-(4-chlorophenyl) | OH | 505.2 |
| 82 | phenyl | propanamide-N-(3,4-dichlorophenyl) | OH | 539.2 |
| 83 | phenyl | propanamide-N-(4-methoxyphenyl) | OH | 501.3 |
| 84 | phenyl | propanamide-N-(3-chlorophenyl) | OH | 505.2 |
| 85 | phenyl | propanamide-N-(2-chlorophenyl) | OH | 449.3 |
| 86 | phenyl | propanamide-N-(4-nitrophenyl) | OH | 516.3 |
| 87 | phenyl | propanamide-N-(2-methylphenyl) | OH | 485.3 |
| 88 | phenyl | propanamide-N-(4-chlorobenzyl) | OH | 519.2 |
| 89 | phenyl | propanamide-N-(2-phenylethyl) | OH | 499.3 |

TABLE 1-continued

| Ex. | R¹ and R³ | R⁴ | R² | M/s M+ |
|---|---|---|---|---|
| 90 | phenyl | propanoyl-NH-(2,3-dihydro-1H-inden-2-yl) | OH | 511.3 |
| 91 | phenyl | propanoyl-NH-CH₂-(3-chlorophenyl) | OH | 519.2 |
| 92 | phenyl | propanoyl-NH-CH₂-(2-chlorophenyl) | OH | 519.2 |
| 93 | phenyl | propanoyl-NH-CH₂-(naphthalen-1-yl) | OH | 535.3 |
| 94 | phenyl | propanoyl-NH-(CH₂)₃-(2-oxopyrrolidin-1-yl) | OH | 520.3 |
| 95 | phenyl | propanoyl-NH-CH₂-(3,4-dichlorophenyl) | OH | 553.2 |
| 96 | phenyl | propanoyl-NH-CH₂CH₂-(thiophen-2-yl) | OH | 505.3 |
| 97 | phenyl | propanoyl-NH-CH₂-cyclohexyl | OH | 491.3 |
| 98 | phenyl | propanoyl-NH-CH(CH₃)₂ | OH | 437.3 |
| 99 | phenyl | propanoyl-NH-CH₂CH₃ | OH | 423.2 |

TABLE 1-continued

| Ex. | R¹ and R³ | R⁴ | R² | M/s M+ |
|---|---|---|---|---|
| 100 | tolyl | propanamide-N-CH₂-cyclopropyl | OH | 449.2 |
| 101 | tolyl | propanamide-N-propyl | OH | 437.3 |
| 102 | tolyl | propanamide-N-cyclohexyl | OH | 477.3 |
| 103 | tolyl | propanamide-N-CH₂-(2-thienyl) | OH | 491.2 |
| 104 | tolyl | propanamide-N-CH₂CH₂-OCH₃ | OH | 453.3 |
| 105 | tolyl | propanamide-N-CH₂-(4-methylphenyl) | OH | 499.3 |
| 106 | tolyl | propanamide-N-CH₂CH₂-C≡N | OH | 448.3 |
| 107 | tolyl | propanamide-N-CH₂CH₂-(4-sulfamoylphenyl) | OH | 578.3 |
| 108 | tolyl | propanamide-N-CH₂CH₂CH₂-O-CH(CH₃)₂ | OH | 495.3 |

TABLE 1-continued
| Ex. | R¹ and R³ | R⁴ | R² | M/s M+ |
|---|---|---|---|---|
| 109 |  | 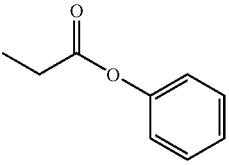 | F | 474.3 |
| 110 | 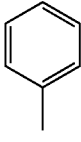 | 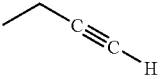 | F | 378.2 |
| 111 | 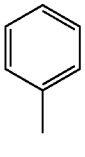 | 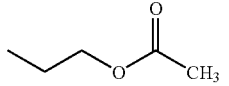 | F | 426.3 |
| 112 | 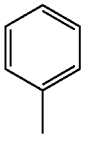 | 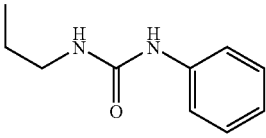 | OH | 500.4 |
| 113 | 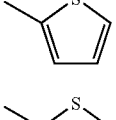 | 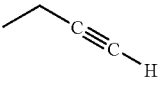 | OH | 402.3 |
| 114 | 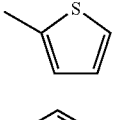 | 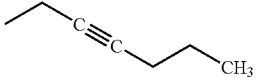 | OH | 430 |
| 115 | 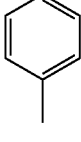 | 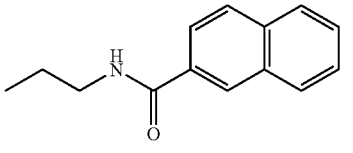 | OH | 535.2 |
| 116 | 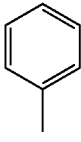 | 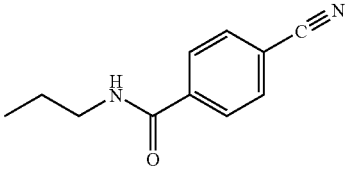 | OH | 510.2 |
| 117 | 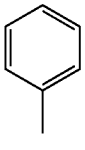 | 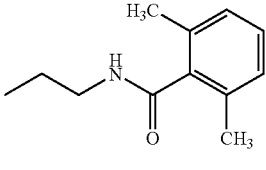 | OH | 513.3 |
| 118 |  | 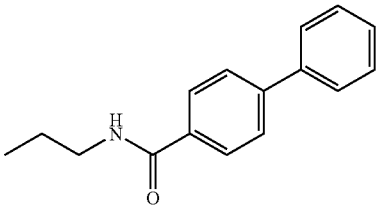 | OH | 561.3 |

TABLE 1-continued
| Ex. | R¹ and R³ | R⁴ | R² | M/s M+ |
|---|---|---|---|---|
| 119 | 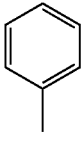 | 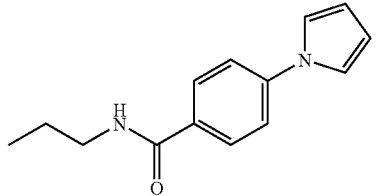 | OH | 550.2 |
| 120 | 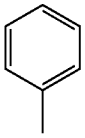 | 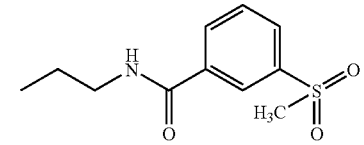 | OH | 563.2 |
| 121 | 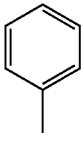 | 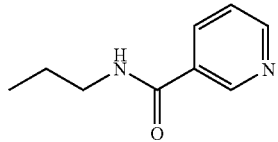 | OH | 486.2 |
| 122 | 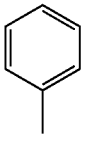 | 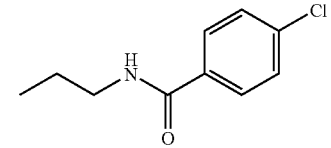 | OH | 519.2 |
| 123 |  | 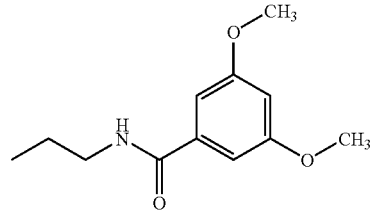 | OH | 545.2 |
| 124 |  | 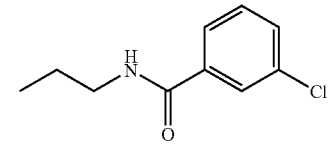 | OH | 519.2 |
| 125 | 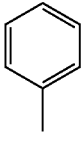 | 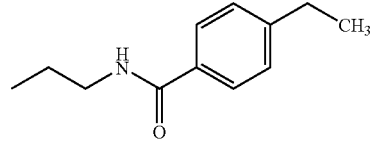 | OH | 513.2 |
| 126 | 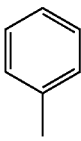 | 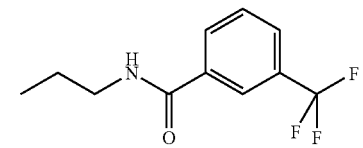 | OH | 553.2 |

TABLE 1-continued
| Ex. | R¹ and R³ | R⁴ | R² | M/s M+ |
|---|---|---|---|---|
| 127 | 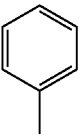 | 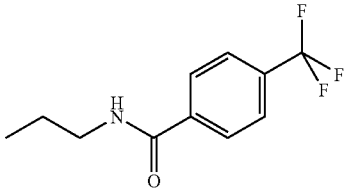 | OH | 553.2 |
| 128 | 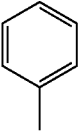 | 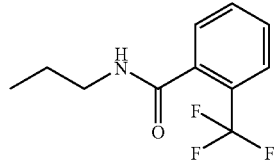 | OH | 553.2 |
| 129 | 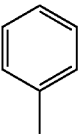 | 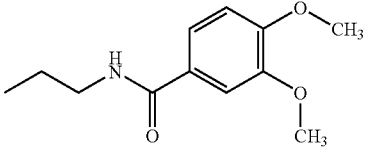 | OH | 545.2 |
| 130 | 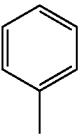 | 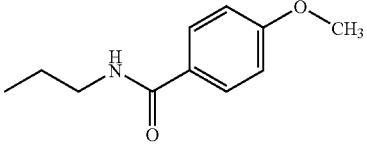 | OH | 515.2 |
| 131 | 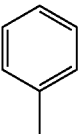 | 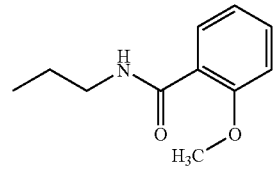 | OH | 515.2 |
| 132 | 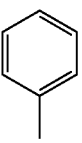 | 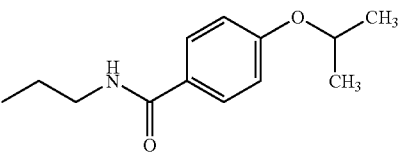 | OH | 543.2 |
| 133 | 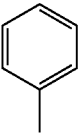 | 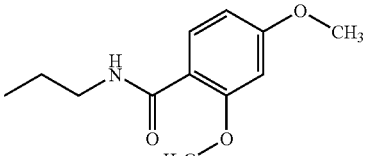 | OH | 545.2 |
| 134 | 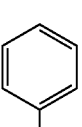 | 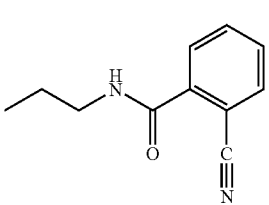 | OH | 511.2 |

TABLE 1-continued
| Ex. | R¹ and R³ | R⁴ | R² | M/s M+ |
|---|---|---|---|---|
| 135 | 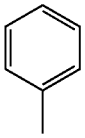 | 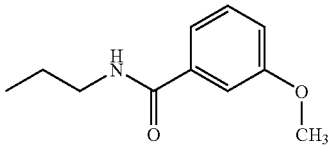 | OH | 515.3 |
| 136 | 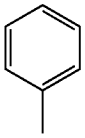 | 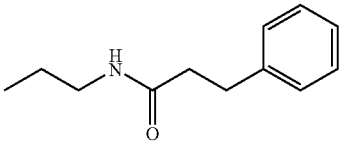 | OH | 513.2 |
| 137 | 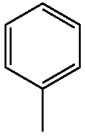 | 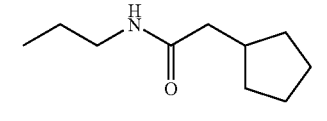 | OH | 491.3 |
| 138 | 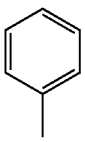 | 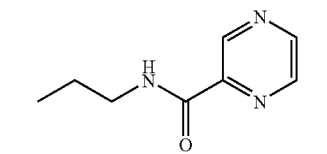 | OH | 487.2 |
| 139 | 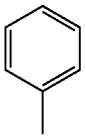 | 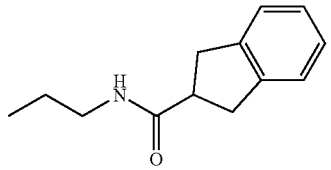 | OH | 525.2 |
| 140 | 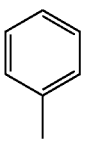 | 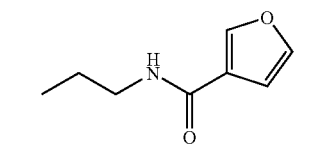 | OH | 475.3 |
| 141 | 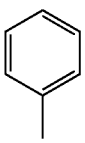 | 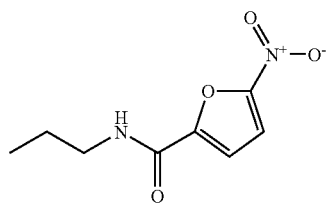 | OH | 520.2 |
| 142 | 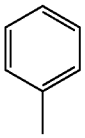 | 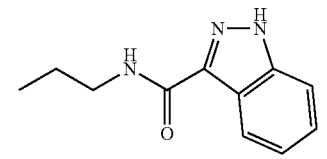 | OH | 525.3 |
| 143 | 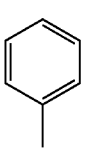 | 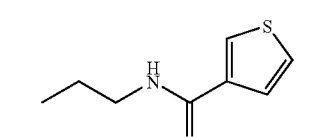 | OH | 491.3 |

TABLE 1-continued

| Ex. | R¹ and R³ | R⁴ | R² | M/s M+ |
|---|---|---|---|---|
| 144 | phenyl | N-propyl amide of 1-methyl-pyrrole-2-carboxamide | OH | 488.3 |
| 145 | phenyl | N-propyl amide of 1,3-dimethyl-pyrazole-5-carboxamide | OH | 503.3 |
| 146 | phenyl | N-propyl amide of 2-phenyl-5-methyl-1,2,3-triazole-4-carboxamide | OH | 566.3 |
| 147 | phenyl | N-propyl amide of 4-methyl-1,2,3-thiadiazole-5-carboxamide | OH | 507.2 |
| 148 | phenyl | N-propyl amide of 5-methyl-isoxazole-3-carboxamide | OH | 490.3 |
| 149 | phenyl | N-propyl amide of 3-methyl-furan-2-carboxamide | OH | 489.3 |
| 150 | phenyl | N-propyl amide of 4-methoxy-thiophene-3-carboxamide | OH | 521.3 |
| 151 | phenyl | N-propyl amide of 3-ethoxy-thiophene-2-carboxamide | OH | 535.3 |

TABLE 1-continued

| Ex. | R¹ and R³ | R⁴ | R² | M/s M+ |
|---|---|---|---|---|
| 152 | phenyl | N-propyl amide linked to 5-acetyl thiophene-2-carboxamide | OH | 533.2 |
| 153 | phenyl | N-propyl amide linked to 3-chloro thiophene-2-carboxamide | OH | 525.2 |
| 154 | phenyl | N-propyl amide linked to 3-bromo thiophene-2-carboxamide | OH | 569.2 |
| 155 | phenyl | N-propyl amide linked to 2,5-dimethyl furan-3-carboxamide | OH | 503.3 |
| 156 | phenyl | N-propyl amide linked to 5-bromo furan-2-carboxamide | OH | 555.2 |
| 157 | phenyl | N-propyl amide linked to 1,5-dimethyl pyrazole-3-carboxamide | OH | 503.3 |
| 158 | phenyl | N-methyl-N-phenyl propanamide | OH | 485.2 |

Preparation of Specific Examples

Abbreviations used are as follows: DAST is diethylamino-sulfur trifluoride, DCE is dichloro-ethane, DCM is dichloromethane, DIPEA is diisopropylethylamine, DME is dimethoxyethane, HATU is O-(7-azabenzotriazol-1-yl)-N,N,—N',N'-tetramethyl-uronium hexafluorophophate, HPLC is High Performance Liquid Chromatography, Isolute CBA is propylcarboxylic acid, NBS is N-bromosuccinimide, PyBOP is benzotriazol-1-yloxytripyrrolidinophosphonium hexafluorophosphate and THF is tetrahydrofuran. BEMP: 2-tert-Butylimino-2-diethylamino-1,3-dimethyl-perhydro-1,3,2-diazaphosphorine, polymer bound.

In cases where purification is performed by C18 reverse phase column chromatography utilising trifluoroacetic acid as a component of the eluent, the composition of the resulting counter ion was not confirmed spectroscopically, and may indeed be a variable mixture of trifluoroacetate and the halide resulting from the quaternarisation reaction. Where HATU is used as a coupling agent the counter ion may also be hexa fluorophosphate.

Example 1

(R)-1-(Amino-propyl)-3-(2-hydroxy-2,2-diphenyl-acetoxy)-1-azonia-bicyclo[2.2.2]octane (i) Bromide:

To a stirred solution of hydroxy-diphenyl-acetic acid (R)-(1-aza-bicyclo[2.2.2]oct-3-yl) ester (5 g, 14.82 mmol) in DMF (40 ml) is added 3-aminopropyl bromide (pre-neutralised from 3-aminopropyl bromide hydrobromide using polymer supported diethyl amine) (.47 g, 29.54 mmol). The reaction mixture is heated to 40° C. overnight and then concentrated in vacuo. The crude residue is diluted with acetonitrile and the resulting precipitate is filtered and redissolved in DMF (20 ml). Merrifield resin is added to this solution followed by potassium carbonate (20 mg, catalytic amount) and the reaction is stirred at 40° C. for 24 hours. The reaction mixture is filtered and acetonitrile is added to the filtrate. The resulting precipitate is filtered and dried in vacuo to yield the titled compound.

(ii) Chloride:
(a) (R)-1-(3-tert-Butoxycarbonylamino-propyl)-3-(2-hydroxy-2,2-diphenyl-acetoxy)-1-azonia-bicyclo[2.2.2]octane bromide:

Hydroxy-diphenyl-acetic acid (R)-(1-aza-bicyclo[2.2.2]oct-3-yl) ester (1 g, 2.97 mmol) and 3-(BOC-amino) propylbromide (1.06 g, 4.73 mmol) are dissolved in DMF (10 ml) and stirred to 60° C. for 4 hours. The solvent is removed in vacuo and purification of the crude residue by chromatography on C18 silica, eluting with water:acetonitrile affords the title compound as a colourless foam.

(b) (R)-1-(3-Amino-propyl)-3-(2-hydroxy-2,2-diphenyl-acetoxy)-1-azonia-bicyclo[2.2.2]octane chloride hydrochloride:

To a stirred solution of (R)-1-(3-tert-Butoxycarbonylamino-propyl)-3-(2-hydroxy-2,2-diphenyl-acetoxy)-1-azonia-bicyclo[2.2.2]octane bromide [Example 1(ii)(a)] (1 g, 2.02 mmol) in dioxane (10 ml) at room temperature is added hydrochloric acid (1.5 ml, 4M aqueous solution). The reaction mixture is stirred for 16 hours and the solvent is removed in vacuo to yield the titled compound as a white solid.

Example 2

(R)-1-(3-Benzoylamino-propyl-3-(2-hydroxy-2,2-diphenyl-acetoxy)-1-azonia-bicyclo[2.2.2]-octane trifluoroacetate To a stirred solution of benzoic acid (0.012 g, 0.1 mmol) and HATU (0.038 g, 0.1 mmol) in DMF (0.5 ml) is added DIPEA (0.05 ml). The reaction mixture is left to stand at room temperature for 15 minutes after which time, a solution comprising (R)-1-(3-amino-propyl)-3-(2-hydroxy-2,2-diphenyl-acetoxy)-1-azonia-bicyclo[2.2.2]octane chloride hydrochloride [Example 1(ii)] (0.047 g, 0.1 mmol) in DMF (0.5 ml) is added. The reaction mixture is stirred at room temperature for 30 minutes and the solvent is removed in vacuo. Purification by mass directed preparative HPLC eluting with acetonitrile:water:trifluoroacetic acid yields the titled compound as a colourless oil.

Examples 3 to 46

These compounds, namely (R)-3-(2-Hydroxy-2,2-diphenyl-acetoxy)-1-(3-[(naphthalene-2-carbonyl)-amino]-propyl)-1-azonia-bicyclo[2.2.2]octane trifluoroacetate, (R)-1-[3-(4-Cyano-benzoylamino)-propyl]-3-(2-hydroxy-2,2-diphenyl-acetoxy)-1-azonia-bicyclo[2.2.2]octane trifluoroacetate, (R)-1-[3-(2,6-Dimethyl-benzoylamino)-propyl]-3-(2-hydroxy-2,2-diphenyl-acetoxy)-1-azonia-bicyclo-[2.2.2]octane trifluoroacetate, (R)-1-(3-[(Biphenyl-4-carbonyl)-amino]-propyl)-3-(2-hydroxy-2,2-diphenyl-acetoxy)-1-azonia-bicyclo[2.2.2]octane trifluoro-acetate, (R)-3-(2-Hydroxy-2,2-diphenyl-acetoxy)-1-[3-(4-pyrrol-1-yl-benzoylamino)-propyl]-1-azonia-bicyclo[2.2.2]octane trifluoroacetate, (R)-3-(2-Hydroxy-2,2-diphenyl-acetoxy)-1-[3-(3-methanesulfonyl-benzoyl-amino)-propyl]-1-azonia-bicyclo[2.2.2]octane trifluoroacetate, (R)-3-(2-Hydroxy-2,2-diphenyl-acetoxy)-1-[3-[(pyridine-3-carbonyl)-amino]-propyl]-1-azonia-bicyclo-[2.2.2]octane trifluoro-acetate, (R)-1-[3-(4-Chloro-benzoylamino)-propyl]-3-(2-hydroxy-2,2-diphenyl-acetoxy)-1-azonia-bicyclo[2.2.2]octane trifluoroacetate, (R)-1-(3-(3,5-Dimethoxy-benzoylamino)-propyl)-3-(2-hydroxy-2,2-diphenyl-acetoxy)-1-azonia-bicyclo-[2.2.2]octane trifluoroacetate, (R)-1-[3-(3-Chloro-benzoylamino)-propyl]-3-(2-hydroxy-2,2-diphenyl-acetoxy)-1-azonia-bicyclo[2.2.2]-octane trifluoroacetate, (R)-1-[3-(4-Ethyl-benzoyl-amino)-propyl]-3-(2-hydroxy-2,2-diphenyl-acetoxy)-1-azonia-bicyclo[2.2.2]octane trifluoro-acetate, (R)-3-(2-Hydroxy-2,2-diphenyl-acetoxy)-1-[3-(3-trifluoromethyl-benzoylamino)-propyl]-1-azonia-bicyclo[2.2.2]octane trifluoroacetate, (R)-3-(2-Hydroxy-2,2-diphenyl-acetoxy)-1-[3-(4-trifluoromethyl-benzoyl-amino)-propyl]-1-azonia-bicyclo[2.2.2]octane trifluoroacetate, (R)-3-(2-Hydroxy-2,2-diphenyl-acetoxy)-1-[3-(2-trifluoromethyl-benzoyl-amino)-propyl]-1-azonia-bicyclo[2.2.2]octane trifluoroacetate, (R)-1-[3-(3,4-Dimethoxy-benzoylamino)-propyl]-3-(2-hydroxy-2-diphenyl-acetoxy)-1-azonia-bicyclo[2.2.2]octane trifluoroacetate, (R)-3-(2-Hydroxy-2,2-diphenyl-acetoxy)-1-[3-(4-methoxy-benzoylamino)-propyl]-1-azonia-bicyclo-[2.2.2]octane-trifluoro-acetate, (R)-3-(2-Hydroxy-2,2-diphenyl-acetoxy)-1-[3-(2-methoxy-benzoylamino)-propyl]-1-azonia-bicyclo[2.2.2]octane trifluoro-acetate, (R)-3-(2-Hydroxy-2,2-diphenyl-acetoxy)-1-[3-(4-isopropoxy-benzoylamino)-propyl]-1-azonia-bicyclo[2.2.2]octane trifluoroacetate, (R)-1-[3-(2,4-Dimethoxy-benzoylamino)-propyl]-3-(2-hydroxy-2,2-diphenyl-acetoxy)-1-azonia-bicyclo-[2.2.2]octane trifluoroacetate, (R)-1-[3-(2,3-Dimethoxy-benzoyl-amino)-propyl]-3-(2-hydroxy-2,2-diphenyl-acetoxy)-1-azonia-bicyclo-[2.2.2]octane trifluoro-acetate, (R)-1-[3-(2-Cyano-benzoylamino)-propyl]-3-(2-hydroxy-2,2-diphenyl-acetoxy)-1-azonia-bicyclo[2.2.2]octane trifluoroacetate, (R)-1-[3-(3-Fluoro-4-methoxy-benzoylamino)-propyl]-3-(2-hydroxy-2,2-diphenyl-acetoxy)-1-azonia-bicyclo[2.2.2]-octane trifluoroacetate, (R)-1-[3-(3-Cyano-benzoyl-amino)-propyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[3-(3-methoxy-benzoylamino)-propyl]-1-azonia-bicyclo[2.2.2]octane trifluoroacetate, (R)-3-(2-Hydroxy-2,2-diphenyl-acetoxy)-1-[3-[(pyridine-2-carbonyl)-amino]-propyl]-1-azonia-bicyclo[2.2.2]octane trifluoroacetate, (R)-3-(2-Hydroxy-2,2-diphenyl-acetoxy)-1-(3-[(pyridine-4-carbonyl)-amino]-propyl)-1-azonia-bicyclo-[2.2.2]octane trifluoroacetate, (R)-3-(2-Hydroxy-2,2-diphenyl-acetoxy)-1-(3-[(5-methyl-isoxazole-3-carbonyl)-amino]-propyl)-1-azonia-bicyclo[2.2.2]octane trifluoroacetate, (R)-1-[3-(Cyclohexanecarbonyl-amino)-propyl]-3-(2-hydroxy-2,2-diphenyl-acetoxy)-1-azonia-bicyclo-[2.2.2]octane trifluoroacetate, (R)-1-[3-(Cycloheptanecarbonyl-amino)-propyl]-3-(2-hydroxy-2,2-diphenyl-acetoxy)-1-azonia-bicyclo-[2.2.2]octane trifluoroacetate, (R)-1-[3-(Cyclopentane-carbonyl-amino)-propyl]-3-(2-hydroxy-2,2-diphenyl-acetoxy)-1-azonia-bicyclo[2.2.2]octane trifluoroacetate, (R)-1-[3-(3,3-Dimethyl-butyrylamino)-propyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-(3-phenylacetylamino-propyl)-1-azonia-bicyclo[2.2.2]octane trifluoroacetate, (R)-3-(2-Hydroxy-2,2-diphenyl-acetoxy)-1-[3-(3-phenyl-propionylamino)-propyl]-1-azonia-bicyclo-[2.2.2]octane trifluoroacetate, (R)-1-[3-[(1-Acetyl-piperidine-4-carbonyl)-amino]-propyl]-3-

(2-hydroxy-2,2-diphenyl-acetoxy)-1-azonia-bicyclo[2.2.2]octane trifluoroacetate, (R)-1-[3-(2-Cyclopentyl-acetylamino)-propyl]-3-(2-hydroxy-2,2-diphenyl-acetoxy)-1-azonia-bicyclo[2.2.2]-octane trifluoroacetate, (R)-3-(2-Hydroxy-2,2-diphenyl-acetoxy)-1-[3-[(pyrazine-2-carbonyl)-amino]-propyl]-1-azonia-bicyclo-(2.2.2)octane trifluoroacetate, (R)-3-(2-Hydroxy-2,2-diphenyl-acetoxy)-1-(3-[(indane-2-carbonyl)-amino]-propyl)-1-azonia-bicyclo[2.2.2]octane trifluoroacetate, (R)-3-(2-Hydroxy-2,2-diphenyl-acetoxy)-1-[3-(2-pyridin-2-yl-acetylamino)-propyl]-1-azonia-bicyclo[2.2.2]octane trifluoroacetate, (R)-3-(2-Hydroxy-2,2-diphenyl-acetoxy)-1-[3-[(2-methyl-pyridine-3-carbonyl)-amino]-propyl]-1-azonia-bicyclo[2.2.2]octane trifluoroacetate, (R)-3-(2-Hydroxy-2,2-diphenyl-acetoxy)-1-[3-(2-nitro-benzoylamino)-propyl]-1-azonia-bicyclo[2.2.2]octane trifluoroacetate, (R)-1-[3-(2-Chloro-benzoylamino)-propyl]-3-(2-hydroxy-2,2-diphenyl-acetoxy)-1-azonia-bicyclo[2.2.2]octane trifluoroacetate, (R)-3-(2-Hydroxy-2-diphenyl-acetoxy)-1-[3-(2-methanesulfonyl-benzoylamino)-propyl]-1-azonia-bicyclo[2.2.2]-octane trifluoroacetate, (R)-1-[3-(3,5-Dimethyl-benzoylamino)-propyl]-3-(2-hydroxy-2,2-diphenyl-acetoxy)-1-azonia-bicyclo-[2.2.2]octane trifluoroacetate and (R)-3-(2-Hydroxy-2,2-diphenyl-acetoxy)-1-(3-isobutyryl-amino-propyl)-1-azonia-bicyclo[2.2.2]octane trifluoroacetate respectively, are all prepared by the procedure of Example 2 from (R)-1-(3-Amino-propyl)-3-(2-hydroxy-2,2-diphenyl-acetoxy)-1-azonia-bicyclo[2.2.2]octane chloride [Example 1(ii)] and the appropriate acid.

Example 47

(R)-3-(2-Hydroxy-2,2-diphenyl-acetoxy)-1-[3-(3-phenyl-ureido)-propyl]-1-azonia-bicyclo-[2.2.2]octane trifluoroacetate To a solution comprising (R)-1-(3-amino-propyl)-3-(2-hydroxy-2,2-diphenyl-acetoxy)-1-azonia-bicyclo[2.2.2]octane chloride [Example 1(ii)] (0.023 g, 0.05 mmol) and DIPEA (0.025 ml) in DMF (0.25 ml) is added phenyl isocyanate (0.006 ml). The reaction mixture is left to stand at room temperature overnight. Purification using mass directed preparative HPLC eluting with acetonitrile:water:trifluoroacetic acid affords the titled compound.

Example 48

(R)-1-{3-[3-(4-Butyl-2-methyl-phenyl)-ureido]-propyl}-3-(2-hydroxy-2,2-diphenyl-acetoxy)-1-azonia-bicyclo[2.2.2]octane trifluoroacetate This compound is made via an analogous procedure to (R)-3-(2-Hydroxy-2,2-diphenyl-acetoxy)-1-[3-(3-phenyl-ureido)-propyl]-1-azonia-bicyclo[2.2.2]octane trifluoroacetate (Example 47) by replacing phenyl isocyanate with 4-butyl-1-isocyanato-2-methyl-benzene.

Example 49

(R)-3-(2-Hydroxy-2,2-diphenyl-acetoxy)-1-[2-(toluene-4-sulfonylamino)-ethyl]-1-azonia-bicyclo[2.2.2]octane trifluoroacetate (i) (R)-1-(2-tert-Butoxycarbonylamino-ethyl)-3-(2-hydroxy-2-diphenyl-acetoxy)-1-azonia-bicyclo[2.2.2]octane bromide:

To a stirred suspension of hydroxy-diphenyl-acetic acid (R)-(1-aza-bicyclo[2.2.2]oct-3-yl) ester (2.5 g, 7.42 mmol) in DMF (50 ml) under an atmosphere of argon is added (2-Bromo-ethyl)-carbamic acid tert-butyl ester (2.5 g, 11.16 mmol). The reaction mixture is heated to 60° C. overnight and then the solvent is removed in vacuo to yield a brown oil which is used crude in the next step.

(ii) (R)-1-(2-Amino-ethyl)-3-(2-hydroxy-2,2-diphenyl-acetoxy)-1-azonia-bicyclo[2.2.2]octane bromide hydrobromide:

To a stirred suspension of (R)-1-(2-tert-butoxycarbonylamino-ethyl)-3-(2-hydroxy-2,2-diphenyl-acetoxy)-1-azonia-bicyclo[2.2.2]octane bromide (0.5 g, 1.04 mmol) in dioxane (25 ml) is added hydrogen bromide solution in dioxane (1 ml, prepared by bubbling HBr gas through dry, cooled dioxane). The reaction mixture is stirred at room temperature overnight. The solvent is removed in vacuo and purification of the crude residue by chromatography on C18 silica, eluting with water:acetonitrile affords the title compound as a brown solid.

(iii) (R)-3-(2-Hydroxy-2,2-diphenyl-acetoxy)-1-[2-(toluene-4-sulfonylamino)-ethyl]-1-azonia-bicyclo[2.2.2]octane trifluoroacetate:

A solution comprising (R)-1-(2-amino-ethyl)-3-(2-hydroxy-2,2-diphenyl-acetoxy)-1-azonia-bicyclo[2.2.2]octane bromide hydrobromide [Example 50(ii)] (0.032 g, 0.059 mmol) p-toluenesulfonyl chloride (0.011 g, 0.059 mmol) and DIPEA (0.041 ml, 0.236 mmol) in DMF (0.5 ml) is allowed to stir at room temperature for 66 hours. Purification using mass directed preparative HPLC eluting with acetonitrile:water:trifluoroacetic acid affords the titled compound.

Example 50

(R)-1-(2-Benzoylamino-ethyl)-3-(2-hydroxy-2,2-diphenyl-acetoxy)-1-azonia-bicyclo[2.2.2]-octane bromide (i) (R)-1-(2-tert-Butoxycarbonylamino-ethyl)-3-(2-hydroxy-2,2-diphenyl-acetoxy)-1-azonia-bicyclo[2.2.2]octane bromide:

To a stirred suspension of hydroxy-diphenyl-acetic acid (R)-(1-aza-bicyclo[2.2.2]oct-3-yl) ester (2.5 g, 7.42 mmol) in DMF (50 ml) under an atmosphere of argon is added (2-Bromo-ethyl)-carbamic acid tert-butyl ester (2.5 g, 11.16 mmol). The reaction mixture is heated to 60° C. overnight and then the solvent is removed in vacuo to yield a brown oil which is used crude in the next step.

(ii) (R)-1-(2-Amino-ethyl)-3-(2-hydroxy-2,2-diphenyl-acetoxy)-1-azonia-bicyclo[2.2.2]octane bromide hydrobromide:

To a stirred suspension of (R)-1-(2-tert-butoxycarbonylamino-ethyl)-3-(2-hydroxy-2,2-diphenyl-acetoxy)-1-azonia-bicyclo[2.2.2]octane bromide (0.5 g, 1.04 mmol) in dioxane (25 ml) is added hydrogen bromide solution in dioxane (1 ml, prepared by bubbling HBr gas through dry, cooled dioxane). The reaction mixture is stirred at room temperature overnight. The solvent is removed in vacuo and purification of the crude residue by chromatography on C18 silica, eluting with water:acetonitrile affords the title compound as a brown solid.

(iii) (R)-1-(2-Benzoylamino-ethyl)-3-(2-hydroxy-2,2-diphenyl-acetoxy)-1-azonia-bicyclo[2.2.2]-octane bromide:

To a stirred suspension of (R)-1-(2-Amino-ethyl)-3-(2-hydroxy-2,2-diphenyl-acetoxy)-1-azonia-bicyclo[2.2.2]octane bromide hydrobromide [50(H)] (0.28 g, 0.517 mmol) in DCM at 0° C. is added triethylamine (0.216 ml, 1.552 mmol) followed by benzoyl bromide (0.122 ml, 1.03 mmol). The reaction mixture is stirred at 0° C. for 1.5 hours and the solvent was removed in vacuo. Purification of the crude residue by chromatography on C18 silica, eluting with water:acetonitrile affords the title compound.

Example 51

(R)-1-[(5-Fluoro-benzothiazol-2-ylcarbamoyl)-methyl]-3-(2-hydroxy-2,2-diphenyl-acetoxy)-1-azonia-bicyclo[2.2.2]octane trifluoroacetate Hydroxy-diphenyl-acetic acid (R)-(1-aza-bicyclo[2.2.2]oct-3-yl) ester (0.050 g, 0.148 mmol), 2-Bromo-N-(5-fluoro-benzothiazol-2-yl)-acetamide (0.064 g, 0.222 mmol) and potassium carbonate (0.01 g, catalytic quantity) are added to DMSO (0.5 ml) and stirred together at 40° C. overnight. Purification using mass directed preparative HPLC eluting with acetonitrile:water:trifluoroacetic acid affords the titled compound.

Example 52

(R)-3-(2-Hydroxy-2,2-diphenyl-acetoxy)-1-phenyl-carbamoylmethyl-1-azonia-bicyclo[2.2.2]octane (i) Trifluoroacetate:
To a sealed vial containing hydroxy-diphenyl-acetic acid (R)-(1-aza-bicyclo[2.2.2]oct-3-yl) ester (0.020 g, 0.059 mmol in DMSO) is added 2-chloro-N-phenyl-acetamide (0.030 g, 0.177 mmol) in methylene chloride. The reaction mixture is stirred at room temperature overnight and purification using mass directed preparative HPLC eluting with acetonitrile:water: trifluoroacetic acid affords the titled compound.

(ii) Chloride:
Hydroxy-diphenyl-acetic acid (R)-(1-aza-bicyclo[2.2.2]oct-3-yl) ester (0.2 g, 0.593 mmol) and 2-chloro-N-phenyl-acetamide (0.12 g, 0.89 mmol) are added to DMSO (2 ml) and stirred at 40° C. overnight. The solvent in removed in vacuo and purification by chromatography on C18 silica eluting with water:acetonitrile yields the titled compound as a chloride salt.

Example 53

(R)-1-(Benzylcarbamoyl-methyl)-3-(2-hydroxy-2,2-diphenyl-acetoxy)-1-azonia-bicyclo[2.2.2]-octane trifluoroacetate The title compound is made via an analogous procedure to (R)-3-(2-Hydroxy-2,2-diphenyl-acetoxy)-1-phenylcarbamoylmethyl-1-azonia-bicyclo[2.2.2]octane chloride [Example 52 (ii)] by replacing 2-chloro-N-phenyl-acetamide with 3-chloro-N-phenyl-propionamide.

Examples 54 to 58

These compounds, namely (R)-3-(2-Hydroxy-2,2-diphenyl-acetoxy)-1-prop-2-ynyl-1-azonia-bicyclo[2.2.2]octane trifluoroacetate, (R)-1-(3-Benzenesulfonylamino-propyl)-3-(2-hydroxy-2,2-diphenyl-acetoxy)-1-azonia-bicyclo[2.2.2]octane trifluoroacetate, (R)-1-But-2-ynyl-3-(2-hydroxy-2,2-diphenyl-acetoxy)-1-azonia-bicyclo[2.2.2]octane trifluoroacetate, (R)-1-Hex-2-ynyl-3-(2-hydroxy-2,2-diphenyl-acetoxy)-1-azonia-bicyclo[2.2.2]octane trifluoroacetate, and (R)-3-(2-Hydroxy-2,2-diphenyl-acetoxy)-1-(3-phenyl-prop-2-ynyl)-1-azonia-bicyclo[2.2.2]-octane trifluoroacetate are prepared made via an analogous procedure to (R)-3-(2-Hydroxy-2,2-diphenyl-acetoxy)-1-phenylcarbamoylmethyl-1-azonia-bicyclo[2.2.2]octane trifluoroacetate [Example 52 (i)] by replacing 2-chloro-N-phenyl-acetamide with the appropriate alkyl halide.

Example 59

(R)-1-(3-tert-Butoxycarbonylamino-propyl)-3-(2-hydroxy-2,2-diphenyl-acetoxy)-1-azonia-bicyclo[2.2.2]octane bromide Preparation of this compound is described in Example 1(ii)(a).

Example 60

(R)-1-tert-Butoxycarbonylmethyl-3-(2-hydroxy-2,2-diphenyl-acetoxy)-1-azonia-bicyclo[2.2.2]-octane bromide To a solution comprising hydroxy-diphenyl-acetic acid (R)-(1-aza-bicyclo[2.2.2]oct-3-yl) ester (0.2 g, 0.593 mmol) in dry chloroform (5 ml) is added r-butylbromoacetate (0.438 ml, 2.96 mmol). The reaction mixture is left to stand at room temperature overnight. The solvent is removed in vacuo and purification of the crude residue by chromatography on C18 silica, eluting with water:acetonitrile affords the title compound as a white solid.

Example 61

(R)-1-(2-tert-Butoxycarbonylamino-ethyl-3-(2-hydroxy-2,2-diphenyl-acetoxy)-1-azonia-bicyclo[2.2.2]octane bromide The title compound is made via an analogous procedure to (R)-1-tert-butoxycarbonylmethyl-3-(2-hydroxy-2,2-diphenyl-acetoxy)-1-azonia-bicyclo[2.2.2]octane bromide (Example 60) by replacing t-butylbromoacetate with (2-bromo-ethyl)-carbamic acid tert-butyl ester.

Example 62

(R)-1-Carboxymethyl-3-(2-hydroxy-2,2-diphenyl-acetoxy)-1-azonia-bicyclo[2.2.2]-octane trifluoroacetate To a stirred solution of (R)-1-tert-Butoxycarbonylmethyl-3-(2-hydroxy-2,2-diphenyl-acetoxy)-1-azonia-bicyclo[2.2.2]octane bromide (Example 60) (0.14 g, 0.264 mmol) in chloroform (5 ml) is added trifluoroacetic acid (1 ml). The reaction mixture is left to stir at room temperature overnight. The solvent is removed in vacuo and purification of the residue by chromatography on C18 silica, eluting with water:acetonitrile affords the titled compound as a white solid.

Example 63

(R)-1-[(5,6-Diethyl-indan-2-ylcarbamoyl-methyl]-3-(2-hydroxy-2,2-diphenyl-acetoxy)-1-azonia-bicyclo[2.2.2]octane trifluoroacetate To a stirred suspension of (R)-1-carboxymethyl-3-(2-hydroxy-2,2-diphenyl-acetoxy)-1-azonia-bicyclo[2.2.2]octane trifluoroacetate [Ex. 62] (0.052 g, 0.102 mmol) in dry DMF (5 ml) is added DIPEA (0.070 ml, 0.408 mmol), HATU (0.097 g, 0.255 mmol) and 5,6-Diethyl-indan-2-ylamine hydrochloride (0.058 g, 0.255 mmol). The mixture is left to stir at room temperature overnight. The solvent is removed in vacuo and purification by mass directed preparative HPLC eluting with acetonitrile:water:trifluoroacetic acid yields the titled compound.

Alternatively, to a stirred suspension of (R)-1-carboxymethyl-3-(2-hydroxy-2,2-diphenyl-acetoxy)-1-azonia-bicyclo[2.2.2]octane trifluoroacetate [Ex. 62] (0.052 g, 0.102 mmol) in dry DMF (5 ml) is added DIPEA (0.053 ml, 0.306 mmol), HATU (0.058 g, 0.153 mmol) and 5,6-Diethyl-indan-2-ylamine hydrochloride (0.035 g, 0.153 mmol). The mixture is left to stir at room temperature overnight. The solvent is removed in vacuo and purification by mass directed preparative HPLC eluting with acetonitrile:water:trifluoroacetic acid yields the titled compound.

Example 64

(R)-3-(2-Hydroxy-2,2-diphenyl-acetoxy)-1-pent-4-ynyl-1-azonia-bicyclo[2.2.2]octane trifluoroacetate Hydroxy-diphenyl-acetic acid (R)-(1-aza-bicyclo[2.2.2]oct-3-yl) ester (0.02 g, 0.059 mmol), 5-chloro-pent-1-yne (0.0073 g, 0.071 mmol), sodium iodide (0.009 g, catalytic amount) and potassium carbonate (0.009 g, catalytic amount) are added to acetonitrile (0.5 ml) and stirred together at 9 hours. Purification is carried out using mass directed preparative HPLC eluting with acetonitrile:water:trifluoroacetic acid. Further purification is carried out by heating the resulting product in Merrifield resin in acetonitrile at 80° C. for 6 hours. The mixture is allowed to cool to room temperature and then filtered. The filtrate is concentrated in vacuo to yield the titled product as an oil.

Example 65

(R)-1-[3-(1,3-Dioxo-1,3-dihydro-isoindol-2-yl)-prop-2-ynyl]-3-(2-hydroxy-2,2-diphenyl-acetoxy)-1-azonia-bicyclo[2.2.2]octane trifluoroacetate The title compound is made via an analogous procedure to (R)-3-(2-hydroxy-2,2-diphenyl-acetoxy)-1-pent-4-ynyl-1-azonia-bicyclo[2.2.2]octane trifluoroacetate (Example 64) by replacing 5-chloro-pent-1-yne with 2-(3-Chloro-prop-1-ynyl)-isoindole-1,3-dione, acetonitrile with DMSO and not adding potassium carbonate.

Examples 66 to 69

These compounds, namely (R)-1-(2-Cyclohexylcarbamoyloxy-ethyl)-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[2-(3-phenyl-ureido)-ethyl]-1-azonia-bicyclo[2.2.2]octane trifluoroacetate, (R)-1-[2-(3-Cyclohexyl-ureido)-ethyl]-3-(2-hydroxy-2,2-diphenyl-acetoxy)-1-azonia-bicyclo-[2.2.2]octane trifluoroacetate and (R)-3-(2-Hydroxy-2,2-diphenyl-acetoxy)-1-pent-2-ynyl-1-azonia-bicyclo[2.2.2]octane trifluoroacetate, are all prepared made via an analogous procedure to (R)-3-(2-hydroxy-2,2-diphenyl-acetoxy)-1-pent-4-ynyl-1-azonia-bicyclo[2.2.2]-octane trifluoroacetate (Example 64) by replacing acetonitrile with DMSO and 5-chloro-pent-1-yne with the appropriate alkyl halide.

Example 70

(R)-1-(3-tert-Butoxycarbonylamino-propyl)-3-(2-hydroxy-2,2-di-thiophen-2-yl-acetoxy)-1-azonia-bicyclo[2.2.2]octane bromide (i) Hydroxy-di-thiophen-2-yl-acetic acid methyl ester:
Potassium hydroxide (100 ml, 1.25 M solution) is added to 2,2'-thenil (Ubichem) at room temperature and the reaction mixture is heated to reflux for 4 hours and then cooled to room temperature. The solution is acidified to pH2 and extracted with ethyl acetate (3×100 ml). The combined organic portions are washed with water (100 ml), dried over $Na_2SO_4$ and cooled to 0° C. TMS-diazomethane (20 ml of a 2M solution in hexanes) is added dropwise and the mixture is allowed to warm to room temperature. Acetic acid (4 ml) is added and the reaction mixture is left at room temperature overnight. The solvent is removed in vacuo and the crude product is dried and triturated with hexane to yield the titled compound as a brown amorphous solid.

(ii) Hydroxy-di-thiophen-2-yl-acetic acid (R)-(1-aza-bicyclo[2.2.2]oct-3-yl) ester:

To a flask containing sodium metal (0.018 g, 0.786 mmol) under an atmosphere of argon was added a suspension comprising hydroxy-di-thiophen-2-yl-acetic acid methyl ester [Example 70 (i)](0.2 g, 0.786 mmol) and <R)-1-Aza-bicyclo[2.2.2]octan-3-ol (0.149 g, 1.179 mmol) in toluene (3 ml). The reaction mixture was stirred under the inert atmosphere at 85° C. for 4 hours and the solvent was removed in vacuo. The resulting crude residue was dissolved in DCM and washed with saturated sodium bicarbonate solution. The organic portion was dried over $MgSO_4$ and concentrated in vacuo to yield a brown oil. Trituration with acetonitrile affords the titled compound.

(iii) (R)-1-(3-tert-Butoxycarbonylamino-propyl)-3-(2-hydroxy-2,2-di-thiophen-2-yl-acetoxy)-1-azonia-bicyclo[2.2.2]octane bromide:

Hydroxy-di-thiophen-2-yl-acetic acid (R)-(1-aza-bicyclo[2.2.2]oct-3-yl) ester (0.758 g, 2.17 mmol) and 3(BOC-amino) propylbromide (0.775 g, 3.25 mmol) are dissolved in DMF (7 ml) and heated at 60° C. for 2.5 hours. The solvent is removed in vacuo and purification of the crude residue by chromatography on C18 silica, eluting with water:acetonitrile affords the titled compound as an oil.

Examples 71 to 75

These compounds, namely (R)-3-(2-Hydroxy-2,2-di-thiophen-2-yl-acetoxy)-1-pent-2-ynyl-1-azonia-bicyclo[2.2.2]octane trifluoroacetate, (R)-1-(2-Cyclohexylcarbamoyloxy-ethyl)-3-(2-hydroxy-2,2-di-thiophen-2-yl-acetoxy)-1-azonia-bicyclo[2.2.2]octane trifluoroacetate, (R)-3-(2-Hydroxy-2,2-di-thiophen-2-yl-acetoxy)-1-[2-(3-phenyl-ureido)-ethyl]-1-azonia-bicyclo[2.2.2]octane trifluoroacetate, (R)-3-(2-Hydroxy-2,2-di-thiophen-2-yl-acetoxy)-1-prop-2-ynyl-1-azonia-bicyclo[2.2.2]octane trifluoroacetate and (R)-1-(Benzylcarbamoyl-methyl)-3-(2-hydroxy-2,2-di-thiophen-2-yl-acetoxy)-1-azonia-bicyclo[2.2.2]octane trifluoroacetate are all made via an analogous procedure to (R)-3-(2-hydroxy-2,2-diphenyl-acetoxy)-1-pent-4-ynyl-1-azonia-bicyclo[2.2.2]-octane trifluoro-acetate (Example 64) by replacing hydroxy-diphenyl-acetic acid (R)-(1-aza-bicyclo[2.2.2]oct-3-yl) ester with hydroxy-di-thiophen-2-yl-acetic acid (R)-(1-aza-bicyclo-[2.2.2]oct-3-yl) ester (Example 70(ii)), by replacing acetonitrile with DMSO and by replacing 5-chloro-pent-1-yne with the appropriate alkyl halide.

Alternative Preparation of the Compound of Example 71 as a Bromide Salt:

A solution of 1-bromo-2-pentyne (0.51 g, 3.44 mmol) in chloroform (2 ml) is treated with polymer supported TEA resin. After a few minutes this solution is added to a solution of hydroxy-di-thiophen-2-yl-acetic acid (R)-(1-aza-bicyclo-[2.2.2]oct-3-yl) ester (Example 70(ii)) (1.0 g, 2.87 mmol) in chloroform (2 ml). The resulting mixture is heated to 50° C. for 18 h and the mixture allowed to cool to room temperature. A white solid is isolated by filtration, washed with chloroform and dried. Recrystallisation from chloroform-acetonitrile, washing the resultant solid with cold acetonitrile, and drying under vacuum gives (R)-3-(2-Hydroxy-2,2-di-thiophen-2-yl-acetoxy)-1-pent-2-ynyl-1-azonia-bicyclo[2.2.2]octane bromide.

Example 76

(R)-3-(2-Hydroxy-2,2-di-thiophen-2-yl-acetoxy)-1-phenylcarbamoylmethyl-1-azonia-bicyclo[2.2.2]octane trifluoroacetate Hydroxy-di-thiophen-2-yl-acetic acid (R)-(1-aza-bicyclo [2.2.2]oct-3-yl) ester (Example 70(ii)) (0.03 g, 0.0857 mmol), 2-chloro-N-phenyl-acetamide (0.0218 g, 0.129 mmol), sodium iodide (0.0026 g, catalytic amount) and potassium carbonate (0.0026 g, catalytic amount) are added to DMSO (1 ml) and heated to 40° C. overnight. The solvent is then removed in vacuo and purification is carried out using mass directed preparative HPLC eluting with acetonitrile:water:trifluoroacetic acid. Further purification is required and is carried by chromatography on C18 silica, eluting with water:acetonitrile to afford the titled compound.

Examples 77 to 79

These compounds, namely (R)-1-[2-(3-Cyclohexyl-ureido)-ethyl]-3-(2-hydroxy-2,2-di-thiophen-2-yl-acetoxy)-1-azonia-bicyclo[2.2.2]octane trifluoroacetate, (R)-1-[(5-Fluoro-benzothiazol-2-ylcarbamoyl)-methyl]-3-(2-hydroxy-2,2-di-thiophen-2-yl-acetoxy)-1-azonia-bicyclo [2.2.2]octane trifluoroacetate and (R)-3-(2-Hydroxy-2,2-di-thiophen-2-yl-acetoxy)-1-(3-phenyl-prop-2-ynyl)-1-azonia-bicyclo[2.2.2]octane trifluoroacetate are all prepared by an analogous procedure to (R)-3-(2-hydroxy-2,2-di-thiophen-2-yl-acetoxy)-1-phenylcarbamoyl-methyl-1-azonia-bicyclo [2.2.2]octane trifluoroacetate (Example 76) by replacing 2-chloro-N-phenyl-acetamide with the appropriate alkyl halide.

Example 80

(R)-1-{[(Furan-2-ylmethyl)-carbamoyl]-methyl}-3-(2-hydroxy-2,2-diphenyl-acetoxy)-1-azonia: bicyclo [2.2.2]octane Trifluoroacetate To a solution of (R)-1-carboxymethyl-3-(2-hydroxy-2,2-diphenyl-acetoxy)-1-azonia-bicyclo-[2.2.2]octane trifluoroacetate [Example 62] (0.04 g, 0.078 mmol) in DCM (0.5 ml) is added DIPEA (0.056 ml) and C-furan-2-yl-methylamine (0.056 ml, 0.634 mmol) followed by PyBOP (0.055 g, 0.106 mmol) in DMF (1 ml). The reaction mixture is left to stir at room temperature over 48 hours. Initial purification is carried out using Solid Phase Extraction with a pH 8 pre-conditioned column (pH adjusted using Isolute CBA). Further purification is carried out using mass directed preparative HPLC eluting with acetonitrile:water:trifluoroacetic acid to afford the titled compound.

Alternatively, to a solution of (R)-1-carboxymethyl-3-(2-hydroxy-2,2-diphenyl-acetoxy)-1-azonia-bicyclo-[2.2.2]octane trifluoroacetate [Example 62] (0.04 g, 0.078 mmol) in DCM (0.5 ml) is added DIPEA (0.056 ml) and C-furan-2-yl-methylamine (0.021 ml, 0.234 mmol) followed by PyBroP (0.055 g, 0.118 mmol) in DMF (1 ml). The reaction mixture is left to stir at room temperature over 48 hours. Initial purification is carried out using Solid Phase Extraction with a pH 8 pre-conditioned column (pH adjusted using Isolute CBA). Further purification is carried out using mass directed preparative HPLC eluting with acetonitrile:water:trifluoroacetic acid to afford the titled compound.

Examples 81 to 108

These compounds, namely (R)-1-[(4-Chloro-phenylcarbamoyl)-methyl]-3-(2-hydroxy-2,2-diphenyl-acetoxy)-1-azonia-bicyclo[2.2.2]octane trifluoroacetate, (R)-1-[(3,4-Dichloro-phenyl-carbamoyl)-methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[(4-methoxy-phenylcarbamoyl)-methyl]-1-azonia-bicyclo [2.2.2]octane trifluoroacetate, (R)-1-[(3-Chloro-phenylcarbamoyl)-methyl]-3-(2-hydroxy-2,2-diphenyl-acetoxy)-1-azonia-bicyclo[2.2.2]octane trifluoroacetate, (R)-1-[(2-Chloro-phenylcarbamoyl)-methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[(4-nitro-phenylcarbamoyl)-methyl]-1-azonia-bicyclo [2.2.2]octane trifluoroacetate, (R)-3-(2-Hydroxy-2,2-diphenyl-acetoxy)-1-(o-tolylcarbamoyl-methyl)-1-azonia-bicyclo [2.2.2]octane trifluoro-acetate, (R)-1-[(4-Chloro-benzylcarbamoyl)-methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-(phenethylcarbamoyl-methyl)-1-azonia-bicyclo[2.2.2]octane trifluoroacetate, (R)-3-(2-Hydroxy-2,2-diphenyl-acetoxy)-1-(indan-2-ylcarbamoylmethyl)-1-azonia-bicyclo[2.2.2]octane trifluoroacetate, (R)-1-[(3-Chloro-benzylcarbamoyl)-methyl]-3-(2-hydroxy-2,2-diphenyl-acetoxy)-1-azonia-bicyclo [2.2.2]octane trifluoroacetate, (R)-1-[(2-Chloro-benzylcarbamoyl)-methyl]-3-(2-hydroxy-2,2-diphenyl-acetoxy)-1-azonia-bicyclo[2.2.2]octane trifluoroacetate,(R)-3-(2-Hydroxy-2,2-diphenyl-acetoxy)-1-{[(naphthalen-1-ylmethyl)-carbamoyl]-methyl}-1-azonia-bicyclo[2.2.2] octane trifluoroacetate, (R)-3-(2-Hydroxy-2,2-diphenyl-acetoxy)-1-{[3-(2-oxo-pyrrolidin-1-yl)-propylcarbamoyl]-methyl}-1-azonia-bicyclo[2.2.2]octane trifluoroacetate, (R)-1-[(3,4-Dichloro-benzylcarbamoyl)-methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[(2-thiophen-2-yl-ethylcarbamoyl)-methyl]-1-azonia-bicyclo[2.2.2]octane trifluoroacetate, (R)-1-[(Cyclo-hexylmethyl-carbamoyl)-methyl]-3-(2-hydroxy-2,2-diphenyl-acetoxy)-1-azonia-bicyclo[2.2.2]-octane trifluoroacetate, (R)-3-(2-Hydroxy-2,2-diphenyl-acetoxy)-1-(isopropylcarbamoyl-methyl)-1-azonia-bicyclo[2.2.2]octane trifluoroacetate, (R)-1-Ethylcarbamoylmethyl-3-(2-hydroxy-2,2-diphenyl-acetoxy)-1-azonia-bicyclo[2.2.2]octane trifluoroacetate, (R)-1-[(Cyclo-propylmethyl-carbamoyl)-methyl]-3-(2-hydroxy-2,2-diphenyl-acetoxy)-1-azonia-bicyclo[2.2.2]-octane trifluoroacetate, (R)-3-(2-Hydroxy-2,2-diphenyl-acetoxy)-1-propylcarbamoylmethyl-1-azonia-bicyclo[2.2.2]octane trifluoroacetate, (R)-1-Cyclohexylcarbamoylmethyl-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-{[(thiophen-2-ylmethyl)-carbamoyl]-methyl}-1-azonia-bicyclo[2.2.2]octane trifluoroacetate, (R)-3-(2-Hydroxy-2,2-diphenyl-acetoxy)-1-[(2-methoxy-ethylcarbamoyl)-methyl]-1-azonia-bicyclo[2.2.2]octane trifluoroacetate, (R)-3-(2-Hydroxy-2,2-diphenyl-acetoxy)-1-[(4-methyl-benzylcarbamoyl)-methyl]-1-azonia-bicyclo[2.2.2]octane trifluoro-acetate, (R)-1-[(2-Cyano-ethylcarbamoyl)-methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-{[2-

(4-sulfamoyl-phenyl)-ethylcarbamoyl}-methyl]-1-azonia-bicyclo[2.2.2]octane trifluoroacetate and (R)-3-(2-Hydroxy-2,2-diphenyl-acetoxy)-1-[(3-isopropoxy-propylcarbamoyl)-methyl]-1-azonia-bicyclo[2.2.2]octane trifluoroacetate are all prepared by an analogous procedure to (R)-1-{[(furan-2-ylmethyl)-carbamoyl]-methyl}-3-(2-hydroxy-2,2-diphenyl-acetoxy)-1-azonia-bicyclo[2.2.2]-octane trifluoroacetate (Example 80)) by replacing C-furan-2-yl-methylamine with the appropriate amine.

Example 109

(R)-3-(2-Fluoro-2,2-diphenyl-acetoxy)-1-phenoxycarbonylmethyl-1-azonia-bicyclo[2.2.2]-octane bromide (i) Fluoro-diphenyl-acetic acid (R)-(1-aza-bicyclo[2.2.2]oct-3-yl) ester:

To a cooled (0° C.), stirred solution of DAST (0.101 ml, 0.826 mmol) in DCM (0.5 ml) under an atmosphere of argon is added, dropwise over 10 minutes, a suspension of hydroxy-diphenyl-acetic acid (R)-(1-aza-bicyclo[2.2.2]oct-3-yl) ester (0.209 g, 0.62 mmol) in DCM (10 ml). The reaction mixture is stirred at 0° C. for 1 hour after which time water (5 ml) is added dropwise followed by sodium hydrogen carbonate solution (3 ml, 10% w/w $NaHCO_3$) to adjust the pH of the solution to pH8. The reaction mixture is diluted with DCM (10 ml) and the organic portion is separated. The aqueous layer is extracted with DCM (10 ml) and the organic portions are combined, dried over $MgSO_4$ and concentrated in vacuo. Purification of the crude residue is carried by chromatography on silica, eluting with DCM: methanol to yield the titled compound as a brown oil.

(ii) (R)-3-(2-Fluoro-2,2-diphenyl-acetoxy)-1-phenoxycarbonylmethyl-1-azonia-bicyclo[2.2.2]-octane bromide:

To a solution of fluoro-diphenyl-acetic acid (R)-(1-aza-bicyclo[2.2.2]oct-3-yl) ester [Example 109(i)] (0.034 g, 0.1 mmol) in DMSO (0.25 ml) is added bromo-acetic acid phenyl ester (0.071 ml, 0.5 mmol). The reaction mixture is left standing at room temperature overnight. Purification is carried out by chromatography on C18 silica, eluting with water:acetonitrile to yield the titled compound as a colourless oil.

Examples 110 and 111

These compounds, namely (R)-3-(2-Fluoro-2,2-diphenyl-acetoxy)-1-prop-2-ynyl-1-azonia-bicyclo[2.2.2]octane bromide and (R)-1-(2-Acetoxy-ethyl)-3-(2-fluoro-2,2-diphenyl-acetoxy)-1-azonia-bicyclo[2.2.2]octane bromide are prepared by an analogous method to (R)-3-(2-fluoro-2,2-diphenyl-acetoxy)-1-phenoxycarbonylmethyl-1-azonia-bicyclo[2.2.2]octane bromide (Example 109) by replacing bromo-acetic acid phenyl ester with the appropriate alkyl halide.

Example 112

(R)-3-(2-Hydroxy-2,2-diphenyl-acetoxy)-1-[2-(3-phenyl-ureido)-ethyl]-1-azonia-bicyclo[2.2.2]-octane trifluoroacetate This compound is made analogously to (R)-3-(2-hydroxy-2,2-diphenyl-acetoxy)-1-[2-(toluene-4-sulfonylamino)-ethyl]-1-azonia-bicyclo[2.2.2]octane trifluoroacetate (Example 49) by replacing p-toluenesulfonyl chloride with phenyl isocyanate.

Example 113

(R)-1-But-2-ynyl-3-(2-hydroxy-2,2-di-thiophen-2-yl-acetoxy)-1-azonia-bicyclo[2.2.2]octane trifluoroacetate This compound is made analogously to (R)-3-(2-hydroxy-2,2-di-thiophen-2-yl-acetoxy)-1-phenylcarbamoylmethyl-1-azonia-bicyclo[2.2.2]octane trifluoroacetate (Example 76) by replacing 2-chloro-N-phenyl-acetamide with the appropriate alkyl halide.

Example 114

(R)-1-Hex-2-ynyl-3-(2-hydroxy-2,2-di-thiophen-2-yl-acetoxy)-1-azonia-bicyclo[2.2.2]octane trifluoroacetate A stirred solution comprising hydroxy-di-thiophen-2-yl-acetic acid (R)-(1-aza-bicyclo[2.2.2]-oct-3-yl) ester (Example 70(ii)) (0.03 g, 0.086 mmol), 1-bromo-2-hexyne (0.021 g, 0.0129 mmol), potassium carbonate (0.002 g, catalytic amount) in acetonitrile (0.5 ml) is heated to 50° C. overnight. The solvent is removed in vacuo and purification by mass directed preparative HPLC eluting with acetonitrile:water:trifluoroacetic acid yields the tided compound.

Example 115

(R)-3-(2-Hydroxy-2,2-diphenyl-acetoxy)-1-[2-[(naphthalene-2-carbonyl)-amino]-ethyl]-1-azonia-bicyclo[2.2.2]octane trifluoroacetate To a solution of naphthalene-2-carboxylic acid (0.019 g, 0.113 mmol) in DMF (0.28 ml) is added diisopropylethylamine (0.02 ml, 0.113 mmol) in DMF (1 ml) followed by HATU (0.043 g, 0.113 mmol) in DMF (0.28 ml). The reaction mixture is allowed to stand for 20 minutes after which time a solution comprising (R)-1-(2-amino-ethyl)-3-(2-hydroxy-2,2-diphenyl-acetoxy)-1-azonia-bicyclo[2.2.2]octane bromide hydrobromide [Example 49(H)] (0.051 g, 0.113 mmol) and diisopropylethylamine (0.02 ml, 0.113 mmol) in DMF (0.57 ml) is added. The reaction mixture is allowed to stand at room temperature over night. Initial purification is carried out using Solid Phase Extraction with a 1 g Isolute ALB cartridge. Further purification is carried out using mass directed preparative HPLC eluting with acetonitrile:water:trifluoroacetic acid to afford the titled compound.

Examples 116 to 157

These compounds, namely (R)-1-[2-(4-Cyano-benzoylamino)-ethyl]-3-(2-hydroxy-2,2-diphenyl-acetoxy)-1-azonia-bicyclo[2.2.2]octane trifluoroacetate, (R)-1-[2-(2,6-Dimethyl-benzoylamino)-ethyl]-3-(2-hydroxy-2,2-diphenyl-acetoxy)-1-azonia-bicyclo[2.2.2]octane trifluoroacetate, (R)-1-(2-[(Biphenyl-4-carbonyl)-amino]-ethyl)-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[2-(4-pyrrol-1-yl-benzoylamino)-ethyl]-1-azonia-bicyclo[2.2.2]octane trifluoro-acetate, (R)-3-(2-Hydroxy-2,2-diphenyl-acetoxy)-1-[2-(3-methanesulfonyl-benzoylamino)-ethyl]-1-azonia-bicyclo[2.2.2]octane trifluoroacetate, (R)-3-(2-Hydroxy-2,2-diphenyl-acetoxy)-1-1-[2[(pyridine-3-carbonyl)-amino]-ethyl]-1-azonia-bicyclo[2.2.2]octane trifluoroacetate, (R)-1-[2-(4-Chloro-benzoylamino)-ethyl]-3-(2-hydroxy-2,2-diphenyl-acetoxy)-1-azonia-bicyclo-[2.2.2]octane trifluoroacetate, (R)-1-[2-(3,5-Dimethoxy-benzoylamino)-ethyl]-3-(2-hydroxy-2,2-diphenyl-acetoxy)-1-azonia-bicyclo[2.2.2]octane trifluoroacetate, (R)-1-[2-(3-Chloro-benzoylamino)-ethyl]-3-<2-hydroxy-2-diphenyl-acetoxy)-1-azonia-bicyclo[2.2.2]octane trifluoroacetate, (R)-1-[2-(4-Ethyl-benzoylamino)-ethyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[2-(3-trifluoromethyl-benzoylamino)-ethyl]-1-azonia-bicyclo[2.2.2]octane trifluoroacetate, (R)-3-(2-Hydroxy-2,2-diphenyl-acetoxy)-1-[2-(4-trifluoromethyl-benzoylamino)-ethyl]-1-azonia-bicyclo-[2.2.2]octane trifluoroacetate, (R)-3-(2-Hydroxy-2,2-diphenyl-acetoxy)-1-[2-(2-trifluoro-methyl-benzoylamino)-ethyl]-1-azonia-bicyclo[2.2.2]octane trifluoroacetate, (R)-1-[2-(3,4-Dimethoxy-benzoylamino)-ethyl]-3-(2-hydroxy-2-diphenyl-acetoxy)-1-azonia-bicyclo[2.2.2]-octane trifluoroacetate, (R)-3-(2-Hydroxy-2,2-diphenyl-acetoxy)-1-[2-(4-methoxy-benzoyl-amino)-ethyl]-1-azonia-bicyclo[2.2.2]octane trifluoroacetate, (R)-3-(2-Hydroxy-2,2-diphenyl-acetoxy)-1-[2-(2-methoxy-benzoylamino)-ethyl]-1-azonia-bicyclo[2.2.2]octane trifluoroacetate, (R)-3-(2-Hydroxy-2,2-diphenyl-acetoxy)-1-[2-(4-isopropoxy-benzoylamino)-ethyl]-1-azonia-bicyclo[2.2.2]octane trifluoroacetate, (R)-1-[2-(2,4-Dimethoxy-benzoylamino)-ethyl]-3-(2-hydroxy-2,2-diphenyl-acetoxy)-1-azonia-bicyclo[2.2.2]octane trifluoroacetate, (R)-1-[2-(2-Cyano-benzoylamino)-ethyl]-3-(2-hydroxy-2,2-diphenyl-acetoxy)-1-azonia-bicyclo[2.2.2]-octane trifluoroacetate, (R)-3-(2-Hydroxy-2,2-diphenyl-acetoxy)-1-[2-(3-methoxy-benzoyl-amino)-ethyl]-1-azonia-bicyclo[2.2.2]octane trifluoroacetate, (R)-3-(2-Hydroxy-2,2-diphenyl-acetoxy)-1-[2-(3-phenyl-propionylamino)-ethyl]-1-azonia-bicyclo[2.2.2]octane trifluoroacetate, (R)-1-[2-(2-Cyclopentyl-acetylamino)-ethyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-(2-[{pyrazine-2-carbonyl)-amino]-ethyl}-1-azonia-bicyclo[2.2.2]octane trifluoroacetate, (R)-3-(2-Hydroxy-2,2-diphenyl-acetoxy)-1-[2-[(indane-2-carbonyl)-amino]-ethyl]-1-azonia-bicyclo[2.2.2]octane trifluoroacetate, (R)-1-[2-(2-Carbamoyl-benzoylamino)-ethyl]-3-(2-hydroxy-2,2-diphenyl-acetoxy)-1-azonia-bicyclo[2.2.2]octane trifluoroacetate and (R)-3-(2-Hydroxy-2,2-diphenyl-acetoxy)-1-[2-(2-nitro-benzoylamino)-ethyl]-1-azonia-bicyclo[2.2.2]octane trifluoroacetate, (R)-3-(2-Hydroxy-2,2-diphenyl-acetoxy)-1-[2-(2-pyridin-3-yl-acetylamino)-ethyl]-1-azonia-bicyclo[2.2.2]octane trifluoroacetate, (R)-1-[2-[(Furan-3-carbonyl)-amino]-ethyl]-3-(2-hydroxy-2,2-diphenyl-acetoxy)-1-azoniabicyclo[2.2.2]octane trifluoroacetate, (R)-3-(2-Hydroxy-2,2-diphenyl-acetoxy)-1-[2-[(5-nitro-furan-2-carbonyl)-amino]-ethyl]-1-azonia-bicyclo[2.2.2]octane trifluoroacetate, (R)-3-(2-Hydroxy-2,2-diphenyl-acetoxy)-1-[2-[(1H-indazole-3-carbonyl)-amino]-ethyl]-1-azonia-bicyclo[2.2.2]octane trifluoroacetate, (R)-3-(2-Hydroxy-2,2-diphenyl-acetoxy)-1-[2-[(thiophene-3-carbonyl)-amino]-ethyl]-1-azonia-bicyclo[2.2.2]octane trifluoroacetate, (R)-3-(2-Hydroxy-2,2-diphenyl-acetoxy)-1-[2-[(1-methyl-1H-pyrrole-2-carbonyl)-amino]-ethyl]-1-azonia-bicyclo[2.2.2]octane trifluoroacetate, (R)-1-[2-[(2,5-Dimethyl-2H-pyrazole-3-carbonyl)-amino]-ethyl]-3-(2-hydroxy-2,2-diphenyl)-acetoxy)-1-azonia -bicyclo[2.2.2]octane trifluoroacetate, (R)-3-(2-Hydroxy-2,2-diphenyl-acetoxy)-1-[2-[(5-methyl-2-phenyl-2H-[1,2,3]triazole-4-carbonyl)-amino]-ethyl]-1-azonia-bicyclo[2.2.2]octane trifluoroacetate, (R)-3-(2-Hydroxy-2,2-diphenyl-acetoxy)-1-[2-[(4-methyl-[1,2,3]thiadiazole-5-carbonyl)-amino]-ethyl]-1-azonia-bicyclo[2.2.2]octane trifluoroacetate, (R)-3-(2-Hydroxy-2,2-diphenyl-acetoxy)-1-[2-[(S-methyl-isoxazole-3-carbonyl)-amino]-ethyl]-1-azonia-bicyclo [2.2.2]octane trifluoroacetate, (R)-3-(2-Hydroxy-2,2-diphenyl-acetoxy)-1-[2-[(3-methyl-furan-2-carbonyl)-amino]-ethyl]-1-azonia-bicyclo[2.2.2]octane trifluoroacetate, (R)-3-(2-Hydroxy-2,2-diphenyl-acetoxy)-1-[2-[(4-methoxy-thiophene-3-carbonyl)-amino]-ethyl]-1-azonia-bicyclo [2.2.2]octane trifluoroacetate, (R)-1-[2-[(3-Ethoxy-thiophene-2-carbonyl)-amino]-ethyl]-3-<2-hydroxy-2,2-diphenyl-acetoxy)-1-azonia-bicyclo[2.2.2]octane trifluoroacetate, (R)-1-[2-[(5-Acetyl-thiophene-2-carbonyl)-amino]-ethyl]-3-(2-hydroxy-2,2-diphenyl-acetoxy)-1-azonia-bicyclo[2.2.2]octane (R)-1-[2-[(3-Chloro-thiophene-2-carbonyl)-amino]-ethyl]-3-(2-hydroxy-2,2-diphenyl-acetoxy)-1-azonia-bicyclo[2.2.2] octane trifluoroacetate, (R)-1-[2-[(3-Bromo-thiophene-2-carbonyl)-amino]-ethyl]-3-(2-hydroxy-2,2-diphenyl-acetoxy)-1-azonia-bicyclo [2.2.2]octane trifluoroacetate, (R)-1-[2-[(2,5-Dimethyl-furan-3-carbonyl)-amino]-ethyl]-3-(2-hydroxy-2,2-diphenyl-acetoxy)-1-azonia-bicyclo [2.2.2]octane trifluoroacetate, (R)-1-[2-[(5-Bromo-furan-2-carbonyl)-amino]-ethyl]-3-(2-hydroxy-2,2-diphenyl-acetoxy)-1-azonia-bicyclo[2.2.2]octane trifluoroacetate, (R)-1-[2-[(1,5-Dimethyl-1H-pyrazole-3-carbonyl)-amino]-ethyl]-3-(2-hydroxy-2,2-diphenyl-acetoxy)-1-azonia-bicyclo[2.2.2]octane trifluoroacetate are all prepared by an analogous procedure to (R)-3-(2-Hydroxy-2,2-diphenyl-acetoxy)-1-{2-[(naphthalene-2-carbonyl}-amino]-ethyl)-1-azonia-bicyclo[2.2.2]octane trifluoroacetate (Example 115) by replacing naphthalene-2-carboxylic acid with the appropriate acid.

Example 158

(R)-3-(2-Hydroxy-2,2-diphenyl-acetoxy)-1-[(methyl-phenyl-carbamoyl)-methyl]-1-azonia-bicyclo[2.2.2] octane Hydroxy-diphenyl-acetic acid (R)-(1-aza-bicyclo[2.2.2] oct-3-yl) ester (0.03 g, 0.09 mmol) and 2-Chloro-N-methyl-N-phenyl-acetamide (0.025 g, 0.136 mmol), are dissolved in acetonitrile-DMSO (3:2, 5 ml) and stirred together at 18 hours at 50° C. Chloromethyl polystyrene resin (Merrifield resin) is added and the reaction stirred for an additional 4 hours at room temperature. Filtration and purification using mass directed preparative HPLC eluting with acetonitrile:water:trifluoroacetic acid followed by treatment with polymer bound Hünig's base then dissolution in ethyl acetate and washing with water, drying and concentration in vacuo gives the titled product as a solid.

Other especially preferred compounds of formula I include compounds of formula XIV where $R^1$, $R^2$, $R^3$, and $R^4$ are as shown in Table 2 below, the method of preparation being described hereinafter. All compounds are quaternary ammonium salts. The table also shows mass spectrometry data.

TABLE 2

| Ex. | $R^1$ and $R^3$ | $R^4$ | $R^2$ | M/s M+ |
|---|---|---|---|---|
| 159 | thiophen-2-yl | propanoyl-NH-pyrazinyl | OH | 485.1 |

TABLE 2-continued

| Ex. | R¹ and R³ | R⁴ | R² | M/s M+ |
|---|---|---|---|---|
| 160 | phenyl | propanoyl-NH-pyrimidin-4-yl | OH | 473.1 |
| 161 | phenyl | propanoyl-NH-(3-hydroxyphenyl) | OH | 487.2 |
| 162 | phenyl | propanoyl-NH-(4-hydroxyphenyl) | OH | 487.3 |
| 163 | phenyl | pentanoic acid tert-butyl ester | OH | 480.25 |
| 164 | phenyl | sec-butyl carbamic acid tert-butyl ester | OH | 495.3 |
| 165 | phenyl | cyclopropylacetylene-ethyl | OH | 417.2 |
| 166 | thiophen-2-yl | cyclopropylacetylene-ethyl | OH | 428.1 |
| 167 | phenyl | tert-butylacetylene-ethyl | OH | 433.3 |
| 168 | thiophen-2-yl | tert-butylacetylene-ethyl | OH | 452.2 |

TABLE 2-continued

| Ex. | R¹ and R³ | R⁴ | R² | M/s M+ |
|---|---|---|---|---|
| 169 | phenyl | pent-2-ynyl with gem-dimethyl (CH(CH₃)₂) | OH | 419.9 |
| 170 | 2-thienyl | pent-2-ynyl with gem-dimethyl (CH(CH₃)₂) | OH | 431.9 |
| 171 | phenyl | but-2-ynyl (—CH₂CH₂C≡C—CH₃) | OH | 405.2 |
| 172 | phenyl | pentanoic acid (—(CH₂)₄COOH) | OH | 424.2 |
| 173 | phenyl | N-phenyl pentanamide | OH | 499.3 |
| 174 | phenyl | N-methyl-N-phenyl pentanamide | OH | 513.35 |
| 175 | phenyl | N-benzyl pentanamide | OH | 513.3 |
| 176 | phenyl | sec-butylamine (CH(CH₃)CH₂CH₃—NH₂) | OH | 395.3 |
| 177 | phenyl | N-(sec-butyl)benzamide | OH | 499.3 |

TABLE 2-continued

| Ex. | R¹ and R³ | R⁴ | R² | M/s M+ |
|---|---|---|---|---|
| 178 | phenyl | butyl-N(CH₃)-C(O)-O-C(CH₃)₃ | OH | 509.3 |
| 179 | phenyl | propyl-NH-C(O)-(4-hydroxyphenyl) | OH | 501.3 |
| 180 | phenyl | propyl-NH-C(O)-(3-hydroxyphenyl) | OH | 501.3 |
| 181 | phenyl | -CH₂CH₂-C(O)-O-CH₂-phenyl | OH | 486.2 |
| 182 | phenyl | -CH₂CH₂CH₂-NH-CH₃ | OH | 395.2 |
| 183 | phenyl | propyl-N(CH₃)-C(O)-phenyl | OH | 499.3 |
| 184 | phenyl | -CH₂CH₂-C(O)-NH-(2-bromophenyl) | OH | 551.2 |
| 185 | phenyl | -CH₂CH₂-C(O)-NH-(3,4-dimethylisoxazol-5-yl) | OH | 490.3 |
| 186 | phenyl | -CH₂CH₂-C(O)-NH-(3-methyl-1,2,4-thiadiazol-5-yl) | OH | 493.3 |

TABLE 2-continued
| Ex. | R¹ and R³ | R⁴ | R² | M/s M+ |
|---|---|---|---|---|
| 187 | 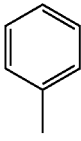 | 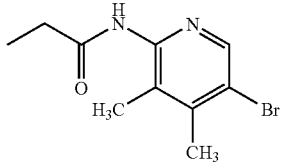 | OH | 580 |
| 188 | 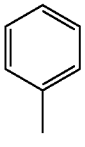 | 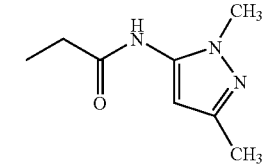 | OH | 489 |
| 189 | 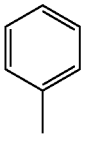 | 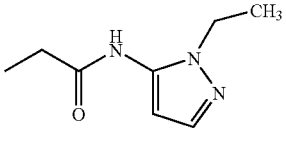 | OH | 489.6 |
| 190 | 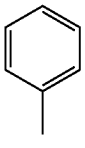 | 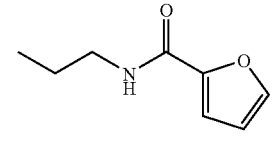 | OH | 475.3 |
| 191 | 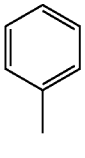 | 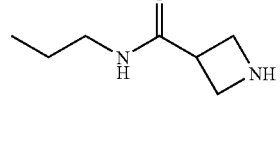 | OH | 464 |
| 192 | 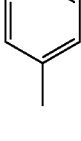 | 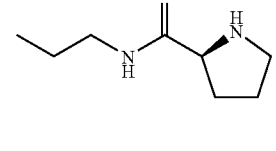 | OH | 478 |
| 193 |  | 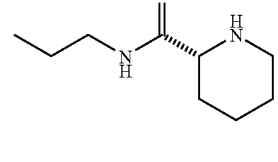 | OH | 492 |
| 194 | 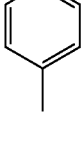 | 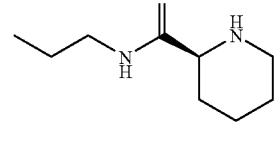 | OH | 492 |
| 195 | 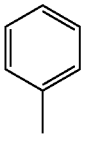 | 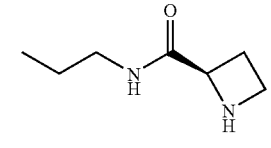 | OH | 464 |

TABLE 2-continued

| Ex. | R¹ and R³ | R⁴ | R² | M/s M+ |
|---|---|---|---|---|
| 196 | phenyl | propanamide-N-(pyridin-2-yl) | OH | 472 |
| 197 | phenyl | propanamide-N-(4-methylpyrimidin-2-yl) | OH | 487 |
| 198 | phenyl | propanamide-N-(6-ethylpyridin-2-yl) | OH | 500.4 |
| 199 | phenyl | propanamide-N-(3-(trifluoromethyl)pyridin-4-yl) | OH | 540.6 |
| 200 | phenyl | propanamide-N-(3-hydroxypyridin-2-yl) | OH | 488 |
| 201 | phenyl | propanamide-N-(pyrimidin-2-yl) | OH | 473 |
| 202 | phenyl | propanamide-N-(4-methyloxazol-2-yl) | OH | 476 |
| 203 | phenyl | propanamide-N-(pyrimidin-4-yl) | OH | 472 |
| 204 | phenyl | propanamide-N-(5-methylthiazol-2-yl) | OH | 492 |

TABLE 2-continued

| Ex. | R¹ and R³ | R⁴ | R² | M/s M+ |
|---|---|---|---|---|
| 205 | phenyl | N-(4-methylthiazol-2-yl)propanamide | OH | 492 |
| 206 | phenyl | N-(pyridin-3-yl)propanamide | OH | 472 |
| 207 | phenyl | N-propylthiophene-2-carboxamide | OH | 491.3 |
| 208 | phenyl | N-propyl-3-methylthiophene-2-carboxamide | OH | — |
| 209 | phenyl | N-propyl-3-chloro-4-methylthiophene-2-carboxamide | OH | 539.2 |
| 210 | phenyl | N-propyl-3-methyl-5-chlorobenzo[b]thiophene-2-carboxamide | OH | 589.2 |
| 211 | phenyl | N-propyl-6-methyl-2-hydroxypyridine-4-carboxamide | OH | 516.3 |
| 212 | phenyl | N-propylthieno[3,2-b]thiophene-2-carboxamide | OH | 547.2 |

TABLE 2-continued

| Ex. | R¹ and R³ | R⁴ | R² | M/s M+ |
|---|---|---|---|---|
| 213 | phenyl | N-propyl amide of 6-fluoro-4H-benzo[1,3]dioxine-8-carboxylic acid | OH | 561.3 |
| 214 | phenyl | N-propyl 5-bromothiophene-2-carboxamide | OH | 571.2 |
| 215 | phenyl | N-propyl 2-propoxybenzamide | OH | 543.3 |
| 216 | phenyl | N-propyl 5-chloro-2-methoxybenzamide | OH | 549.3 |
| 217 | phenyl | N-propyl isonicotinamide | OH | 486.3 |
| 218 | phenyl | N-propyl 2,6-dimethoxybenzamide | OH | 549.3 |
| 219 | phenyl | N-propyl 5-bromonicotinamide | OH | 566.2 |
| 220 | phenyl | N-propyl 3,5-dimethylisoxazole-4-carboxamide | OH | 504.3 |

TABLE 2-continued

| Ex. | R¹ and R³ | R⁴ | R² | M/s M+ |
|---|---|---|---|---|
| 221 | phenyl | propyl-NH-C(=O)-cyclopropyl-OH | OH | 465.3 |
| 222 | phenyl | propyl-NH-C(=O)-(2-trifluoromethyl-1,8-naphthyridin-3-yl) | OH | 605.3 |
| 223 | phenyl | propyl-NH-C(=O)-(6-methylpyridin-3-yl) | OH | — |
| 224 | phenyl | propyl-NH-C(=O)-cyclopropyl | OH | 449.3 |
| 225 | phenyl | propyl-NH-C(=O)-(4-chloro-3-sulfamoylphenyl) | OH | 598.2 |
| 226 | phenyl | propyl-NH-C(=O)-(4,5,6,7-tetrahydrobenzo[c]thiophen-1-yl) | OH | 545.3 |
| 227 | phenyl | propyl-NH-C(=O)-(2,7-dimethylimidazo[1,2-a]pyridin-3-yl) | OH | 553.3 |
| 228 | phenyl | propyl-NH-C(=O)-(3-chloro-4-methylsulfonylthiophen-2-yl) | OH | 603.2 |

TABLE 2-continued
| Ex. | R¹ and R³ | R⁴ | R² | M/s M+ |
|---|---|---|---|---|
| 229 | 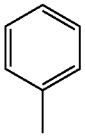 | 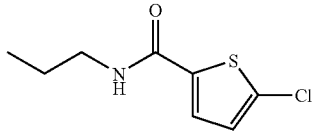 | OH | 525.2 |
| 230 | 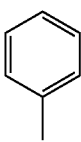 | 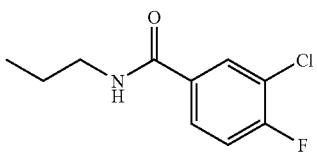 | OH | 537.2 |
| 231 | 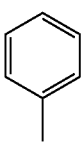 | 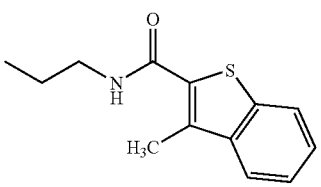 | OH | 555.3 |
| 232 | 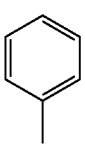 | 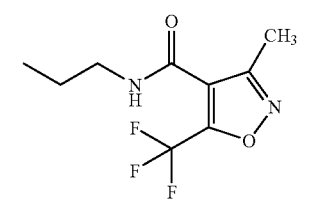 | OH | 558.3 |
| 233 | 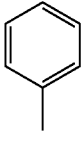 | 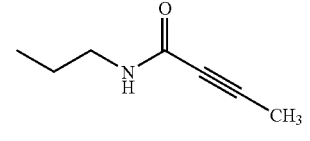 | OH | 447.3 |
| 234 | 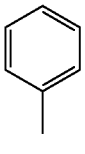 | 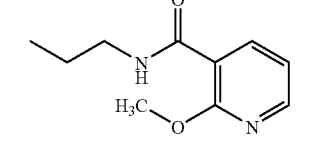 | OH | 516.3 |
| 235 | 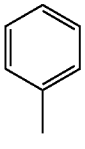 | 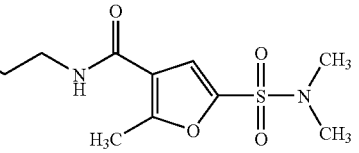 | OH | 596.3 |
| 236 | 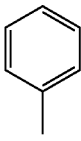 | 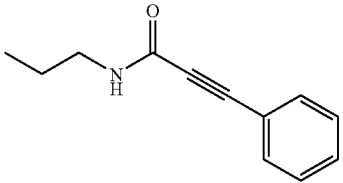 | OH | 509.3 |
| 237 | 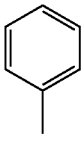 | 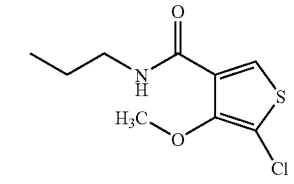 | OH | 555.2 |

TABLE 2-continued

| Ex. | R¹ and R³ | R⁴ | R² | M/s M+ |
|---|---|---|---|---|
| 238 | phenyl | propyl-NH-C(O)-(2-tetrahydrofuryl) | OH | 479.4 |
| 239 | phenyl | propyl-NH-C(O)-(4-tetrahydropyranyl) | OH | 493.35 |
| 240 | phenyl | propyl-NH-C(O)-(3-methoxythiophen-2-yl) | OH | 522 |
| 241 | phenyl | propyl-NH-C(O)-(5-methoxythiophen-2-yl) | OH | 551.2 |
| 242 | phenyl | ethyl-C(O)-NH-(isoxazol-3-yl) | OH | 462.2 |
| 243 | thiophen-2-yl | ethyl-C(O)-NH-(isoxazol-3-yl) | OH | 474.1 |
| 244 | thiophen-2-yl | ethyl-C(O)-NH-(pyrimidin-4-yl) | OH | 485.1 |
| 245 | phenyl | ethyl-C(O)-NH-(pyrazin-2-yl) | OH | 473.2 |

Preparation of Specific Examples

Example 159

A) Bromide salt of (R)-3-(2-Hydroxy-2,2-di-thiophen-2-yl-acetoxy)-1-(pyrazin-2-ylcarbamoyl-methyl)-1-azonia-bicyclo[2.2.2]octane i) 2-Bromo-N-pyrazin-2-yl-acetamide:

To a solution of 2-aminopyrazine (5.0 g, 52.6 mmol) in chloroform (250 ml) under an argon atmosphere is added triethylamine (8.79 ml, 63.1 mmol) and the temperature of the resulting mixture reduced to −40° C. To this solution is added a solution of bromoacetylbromide (4.57 ml, 52.6 mmol) in chloroform dropwise over 20 minutes, and stirring continued at −20° C. to −40° C. for 1 hour. The reaction mixture is then quenched by addition to saturated aqueous sodium bicarbonate solution. The chloroform later is separated and washed sequentially with saturated aqueous sodium bicarbonate solution, 0.5 M citric acid and brine. Concentration followed by purification by flash silica column chromatography (gradient elution:ethyl acetate/hexane 4:6 to 4:1) gives the title compound.

ii) (R)-3-(2-Hydroxy-2,2-di-thiophen-2-yl-acetoxy)-1-(pyrazin-2-ylcarbamoylmethyl)-1-azonia-bicyclo[2.2.2] octane bromide:

A solution of 2-bromo-N-pyrazin-2-yl-acetamide (0.77 g, 3.56 mmol) and hydroxy-di-thiophen-2-yl-acetic acid (R)-(1- aza-bicyclo[2.2.2]oct-3-yl) ester (Example 70(ii)) (1.12 g, 3.23 mmol) in dry chloroform are heated at 50° C. for 2 hours. The mixture is then cooled to room temperature and extracted with water. The aqueous layer is concentrated under reduced pressure then redissolved in a small volume of acetonitrile containing a few drops of water. The mixture is allowed to stand at room temperature for several hours, the resulting solid is filtered and dried then redissolved in a small volume of water containing a few drops of acetonitrile. After several hours a solid is formed which is filtered and dried to give the title compound as a white solid.

B) Chloride salt of (R)3-(2-Hydroxy-2,2-di-thiophen-2-yl-acetoxy)-1-(pyrazin-2-ylcarbamoyl-methyl)-1-azonia-bicyclo[2.2.2]octane Pyrazin-2-yl-amine (400 μl, 0.5 M solution in DMF) and triethylamine (500 μl, 0.5 M solution in DMF) are combined and cooled in an ice bath. Chloroacetyl chloride (500 μl, 0.5 M solution in DMF) is added dropwise and stirred at 0° C. for 1 hour. To the crude 2-Chloro-N-pyrazin-2-yl-acetamide and hydroxy-di-thiophen-2-yl-acetic acid (R)-(1-aza-bicyclo[2.2.2]oct-3-yl) ester (Example 70(H)) (800 μl, 0.25 M solution in DMF) is added triethylamine (30 μl, 1 equivalent) and the mixture stirred at room temperature overnight. PS-Bromoacetamidomethyl-NovaGel 2.3 mmol/g (0.3 g) and triethylamine (30 μl, 1 equivalent) are added to the reaction mixture and shaken at room temperature for 2 hours. The reaction mixture is filtered and PS-bromoacetic acid 1.2 mmol/g (0.2 g) is added to the filtrate and shaken at 30° C. for 1 hour. The reaction mixture is passed through a 1 g Isolute SPE (Al-B) cartridge. The solvent is removed in vacuo and purification of the crude residue by mass directed preparative HPLC eluting with water:acetonitrile:trifluoroacetic acid yield the compound as a yellow oil.

Examples 160 to 171

These compounds, namely (R)-3-(2-Hydroxy-2,2-diphenyl-acetoxy)-1-(pyrimidin-4-yl carbamoylmethyl)-1-azonia-bicyclo[2.2.2]octane bromide, (R)-3-(2-Hydroxy-2,2-diphenyl-acetoxy)-1-[(3-hydroxy-phenylcarbamoyl)-methyl]-1-azonia-bicyclo[2.2.2]octane bromide, (R)-3-(2-Hydroxy-2,2-diphenyl-acetoxy)-1-[(4-hydroxy-phenylcarbamoyl)-methyl]-1-azonia-bicyclo[2.2.2]octane bromide, (R)-1-(3-tert-Butoxycarbonyl-propyl)-3-(2-hydroxy-2,2-diphenyl-acetoxy)-1-azonia-bicyclo[2.2.2]octane bromide, (R)-1-((R/S)-2-tert-Butoxycarbonyl-amino-propyl)-3-(2-hydroxy-2,2-diphenyl-acetoxy)-1-azonia-bicyclo[2.2.2]octane bromide, (R)-1-(3-Cyclopropyl-prop-2-ynyl)-3-(2-hydroxy-2,2-diphenyl-acetoxy)-1-azonia-bicyclo-[2.2.2]octane bromide, (R)-1-(3-Cyclopropyl-prop-2-ynyl)-3-(2-hydroxy-2,2-di-thiophen-2-yl-acetoxy)-1-azonia-bicyclo[2.2.2]octane bromide, (R)-1-(4,4-Dimethyl-pent-2-ynyl)-3-(2-hydroxy-2,2-diphenyl-acetoxy)-1-azonia-bicyclo[2.2.2]octane bromide, (R)-1-(4,4-Dimethyl-pent-2-ynyl)-3-(2-hydroxy-2-di-thiophen-2-yl-acetoxy)-1-azonia-bicyclo[2.2.2]octane bromide, (R)-3-(2-Hydroxy-2,2-diphenyl-acetoxy)-1-(4-methyl-pent-2-ynyl)-1-azonia-bicyclo-[2.2.2]octane bromide, (R)-3-(2-Hydroxy-2,2-di-thiophen-2-yl-acetoxy)-1-(4-methyl-pent-2-ynyl)-1-azonia-bicyclo[2.2.2]octane bromide, and (R)-3-(2-Hydroxy-2,2-diphenyl-acetoxy)-1-pent-3-ynyl-1-azonia-bicyclo[2.2.2]octane bromide, are all prepared analogously to (R)-1-tert-Butoxy-carbonylmethyl-3-(2-hydroxy-2,2-diphenyl-acetoxy)-1-azonia-bicyclo[2.2.2]-octane bromide (Example 60) by replacing t-butylbromoacetate with the appropriate organic halide and heating the mixture at 50° C. for 2 to 21 hours. The compounds are purified either by trituration with organic solvents, C18 chromatography (as for Example 60) or recrystalisation from acetonitrile, water or chloroform. The required halides for quaternarisation are either commercially available or readily synthesised by methods well known in the art.

Example 172

(R)-1-(3-Carboxy-propyl)-3-(2-hydroxy-2,2-diphenyl-acetoxy)-1-azonia bicyclo[2.2.2]octane bromide To a stirred solution of (R)-1-(3-tert-Butoxycarbonyl-propyl)-3-(2-hydroxy-2,2-diphenyl-acetoxy)-1-azonia-bicyclo [2.2.2]octane bromide [Example 163] (0.2 g, 0.41 mmol) in methylene chloride (1.5 ml) under an argon atmosphere at room temperature is added hydrobromic acid (33% in acetic acid, 0.36 ml). After stirring at room temperature for 30 minutes, concentration is followed by dissolution in water/acetonitrile and stirring for a further 30 minutes. Concentration then gives the title product.

Examples 173 to 175

These compounds, namely (R)-3-(2-Hydroxy-2,2-diphenyl-acetoxy)-1-(3-phenylcarbamoyl-propyl)-1-azonia-bicyclo[2.2.2]octane trifluoroacetate, (R)-3-(2-Hydroxy-2,2-diphenyl-acetoxy)-1-[3-(methyl-phenyl-carbamoyl)-propyl]-1-azonia-bicyclo[2.2.2]octane trifluoroacetate and (R)-1-(3-Benzylcarbamoyl-propyl)-3-(2-hydroxy-2,2-diphenyl-acetoxy)-1-azonia bicycle [2.2.2]octane trifluoroacetate are all prepared analogously to (R)-1-[(5,6-diethyl-indan-2-ylcarbamoyl)-methyl]-3-(2-hydroxy-2,2-diphenyl-acetoxy)-1-azonia-bicyclo [2.2.2]octane trifluoroacetate [Example 63] but by replacing (R)-1-carboxymethyl-3-(2-hydroxy-2,2-diphenyl-acetoxy)-1-azonia-bicyclo[2.2.2]octane trifluoroacetate [Example 62] with (R)-1-(3-carboxy-propyl)-3-(2-hydroxy-2,2-diphenyl-acetoxy)-1-azonia bicyclo[2.2.2] octane bromide [Example 172] and by replacing 5,6-Diethyl-indan-2-ylamine hydrochloride with the appropriate amine.

Example 176

(R)-1-(2-Amino-propyl)-3-(2-hydroxy-2,2-diphenyl-acetoxy)-1-azoniabicyclo[2.2.2]octane chloride hydrochloride This compound is prepared analogously to (R)-1-((R/S)-2-Amino-ethyl)-3-(2-hydroxy-2,2-diphenyl-acetoxy)-1-azonia-bicyclo[2.2.2]octane bromide hydrobromide [Example 49ii] but by replacing (R)-1-(2-tert-butoxycarbonylamino-ethyl)-3-(2-hydroxy-2,2-diphenyl-acetoxy)-1-azonia-bicyclo[2.2.2]octane bromide [Example 49i] with (R)-1-((R/S)-2-tert-Butoxycarbonylamino-propyl)-3-(2-hydroxy-2,2-diphenyl-acetoxy)-1-azonia-bicyclo[2.2.2]octane bromide [Example 164] and hydrogen bromide solution in dioxane with hydrogen chloride solution in dioxane. The product is isolated on concentration of the reaction medium, without further purification.

Example 177

(R)-1-((R/S)-2-Benzoylamino-propyl)-3-(2-hydroxy-2,2-diphenyl-acetoxy)-1-azonia-bicyclo[2.2.2]octane trifluoroacetate This compound is prepared analogously to (R)-1-(3-benzoylamino-propyl)-3-(2-hydroxy-2,2-diphenyl-acetoxy)-1- azonia-bicyclo[2.2.2]-octane trifluoroacetate [Example 2] but by replacing (R)-1-(3-amino-propyl)-3-(2-hydroxy-2,2-diphenyl-acetoxy)-1-azonia-bicyclo-[2.2.2]octane chloride hydrochloride [Example 1(ii)] with (R)-1-((R/S)-2-amino-propyl)-3-(2-hydroxy-2,2-diphenyl-acetoxy)-1-azoniabicyclo[2.2.2]octane chloride hydrochloride.

Example 178

(R)-1-[3-(tert-Butoxycarbonyl-methyl-amino)-propyl]-3-(2-hydroxy-2,2-diphenyl-acetoxy)-1-azonia-bicyclo[2.2.2]octane chloride (3-Chloro-propyl)-methyl-carbamic acid tert-butyl ester (2.00 g 9.629 mmol) is solubilised in DMF (20 ml) and polystyrene bound DIPEA added, and after a few minutes removed. This solution is then added to a mixture of hydroxy-diphenyl-acetic acid (R)-(1-aza-bicyclo [2.2.2]oct-3-yl) ester (2.1634 g 6.419 mmol) and 200 mg of $K_2CO_3$, followed by the addition of sodium iodide (10 mg) and heating at 60° C. for 2 days. 2.5 g Merrifield resin and 100 mg $K_2CO_3$ is then added to the mixture and heating resumed at 40° C. for 12 hours. The resin is then removed, and the mixture purified by gradient C18 column chromatography to give the title product.

Example 179

(R)-1-[2-(4-Hydroxy-benzoylamino)-ethyl]-3-(2-hydroxy-2,2-diphenyl-acetoxy)-1-azonia-bicyclo [2.2.2]octane bromide i) (R)-1-[2-(4-Benzyloxy-benzoylamino)-ethyl]-3-(2-hydroxy-2,2-diphenyl-acetoxy)-1-azonia-bicyclo[2.2.2]octane bromide:

To a solution of 4-benzyloxybenzoic acid (0.126 mg, 0.55 mmol) in DMF (3 ml) is added diisopropylethylamine (0.3 ml) followed by HATU (0.155 mg, 0.55 mmol). The reaction mixture is stirred for 30 minutes at room temperature after which time a solution comprising (R)-1-(2-amino-ethyl)-3-(2-hydroxy-2,2-diphenyl-acetoxy)-1-azonia-bicyclo[2.2.2] octane bromide hydrobromide [Example 49(ii)] (0.200 g, 0.37 mmol) and the resulting mixture is stirred at room temperature over night. Purification is carried out using preparative C18 column chromatography eluting with acetonitrile:water to afford the titled compound.

ii) (R)-1-[2-(4-Hydroxy-benzoylamino)-ethyl]-3-(2-hydroxy-2,2-diphenyl-acetoxy)-1-azonia-bicyclo[2.2.2]octane bromide:

To a solution of (R)-1-[2-(4-Benzyloxy-benzoylamino)-ethyl]-3-(2-hydroxy-2,2-diphenyl-acetoxy)-1-azonia-bicyclo[2.2.2]octane bromide (0.075 g, 0.11 mmol) in DMF (1 ml) under an argon atmosphere is added 10% Pd on carbon (40 mg) and the resulting solution hydrogenated for 3 hours. The catalyst is then removed by filtration and concentration in vacuo yields the title compound.

Example 180

(R)-1-[2-(3-Hydroxy-benzoylamino)-ethyl]-3-(2-hydroxy-2,2-diphenyl-acetoxy)-1-azonia-bicyclo [2.2.2]octane chloride i) (R)-1-(2-Amino-ethyl)-3-(2-hydroxy-2,2-diphenyl-acetyl)-1-azonia-bicyclo[2.2.2]octane chloride hydrochloride:

To a solution of (R)-1-(2-tert-butoxycarbonylamino-ethyl)-3-(2-hydroxy-2-diphenyl-acetyl)-1-azonia-bicyclo [2.2.2]octane bromide [Example 49i] (8.292 g, 14.82 mmol) in dioxane (100 ml) at room temperature is added hydrochloric acid (18.5 ml, 4 M in dioxane). The reaction mixture is stirred for 20 hours. The solvent is removed in vacuo and purification of the crude residue by chromatography on C18 silica, eluting with water:acetonitrile affords the titled product as a white solid.

ii) (R)-1-[2-(3-Hydroxy-benzoylamino)-ethyl]-3-(2-hydroxy-2,2-diphenyl-acetoxy)-1-azonia-bicyclo[2.2.2]octane chloride:

This is prepared analogously to (R)-1-[2-(4-Hydroxy-benzoylamino)-ethyl]-3-(2-hydroxy-2,2-diphenyl-acetoxy)-1-azonia-bicyclo[2.2.2]octane bromide [Example 179] but 4-benzyloxy-benzoic acid is replaced by 3-benzyloxybenzoic acid and (R)-1-(2-amino-ethyl)-3-(2-hydroxy-2,2-diphenyl-acetoxy)-1-azonia-bicyclo[2.2.2]octane bromide hydrobromide is substituted by (R)-1-(2-amino-ethyl)-3-(2-hydroxy-2,2-diphenyl-acetoxy)-1-azonia-bicyclo[2.2.2]octane chloride hydrochloride [Example 180 i].

Example 181

(R)-1-Benzyloxycarbonylmethyl-3-(2-hydroxy-2-diphenyl-acetoxy)-1-azonia-bicyclo [2.2.2]octane bromide A suspension of hydroxy-diphenyl-acetic acid (R)-(1-azabicyclo[2.2.2]oct-3-yl) ester (1 g, 2.96 mmol) and bromoacetic acid benzyl ester (0.516 ml, 3.26 mmol) in ethylacetate (20 ml) is heated at 50° C. for 2 hours. The reaction mixture is cooled to room temperature and the precipitate removed by filtration. Recrystallisation from acetonitrile (20 ml) gives the title compound.

Example 182

(R)-3-(2-Hydroxy-2,2-diphenyl-acetoxy)-1-(2-methylamino-ethyl)-1-azonia-bicyclo [2.2.2]octane bromide hydrobromide (2-Bromo-ethyl)-methyl-carbamic acid tert-butyl ester (0.09 g, 0.38 mmol) is added to a solution of hydroxy-diphenyl-acetic acid (R)-(1-aza-bicyclo[2.2.2]oct-3-yl) ester (0.265 g, 0.79 mmol) in DMF (10 ml). The resulting mixture is heated at 60° C. for 5 hours and concentrated. This procedure is repeated twice giving the title compound as a mixture containing unreacted hydroxy-diphenyl-acetic acid (R)-(1-aza-bicyclo[2.2.2]oct-3-yl) ester.

Example 183

(R)-1-[2-(Benzoyl-methyl-amino)-ethyl]-3-(2-hydroxy-2,2-diphenyl-acetoxy)-1-azonia-bicyclo[2.2.2] octane trifluoroacetate The crude product from Example 182 is dissolved in acetonitrile (10 ml) and filtered then cooled over an ice bath, under an argon atmosphere. To this cooled solution is added triethylamine (127 id) followed by benzoyl bromide (64 µl) and the reaction stirred for 1 hour. Purification is carried out using mass directed preparative HPLC eluting with acetonitrile:water:trifluoroacetic acid to afford the titled compound.

Example 184

(R)-1-[(2-Bromo-phenylcarbamoyl)-methyl]-3-(2-hydroxy-2,2-diphenyl-acetoxy)]-1-azonia-bicyclo [2.2.2]octant trifluoroacetate (i) N-(2-Bromo-phenyl)-2-chloro-acetamide:
2-Bromoaniline (371 µl, 467 mmol) and triethylamine (651 µl, 5.84 mmol) are dissolved in DMF (2 ml) and cooled in an ice bath. Chloroacetyl chloride (371 µl, 4.67 mmol) is added dropwise and stirred at 0° C. for 1 hour. The solvent is removed in vacuo and used crude in the next step.

ii) (R)-1-[(2-Bromo-phenylcarbamoyl)-methyl]-3-(2-hydroxy-2,2-diphenyl-acetoxy)]-1-azonia-bicyclo[2.2.2]octane trifluoroacetate:

N-(2-Bromo-phenyl)-2-chloro-acetamide (155 mg, 0.622 mmol) and hydroxyl-diphenyl-acetic acid(R)-(1-aza-bicyclo[2.2.2]oct-3-yl)ester (210 mg, 0.622 mmol) are dissolved in DMF (4 ml). The reaction mixture is stirred at 0° C. for 2 hours. PS-Bromoacetamidomethyl-NovaGel 2.3 mmol/g (0.5 g) is added to the reaction mixture and shaken at room temperature for 4 hours. PS-Triphenylphosphine 3 mmol/g (0.5 g) is added to the reaction mixture and shaken at room temperature overnight. The reaction mixture is then passed through a 1 g Isolute SPE (Al-B) cartridge. The solvent is removed in vacuo and purification of the crude residue by mass directed preparative HPLC eluting with water:acetonitrile:trifluoroacetic acid yields the titled compound.

Example 185 to 189

These compounds, namely (R)-1-[(3,4-Dimethyl-isoxazol-5-ylcarbamoyl)-methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[(3-methyl-[1,2,4]thiadiazol-5-ylcarbamoyl)-methyl]-1-azonia-bicyclo[2.2.2]octane trifluoroacetate, (R)-1-[(5-Bromo-3,4-dimethyl-pyridin-2-yl-carbamoyl)-methyl]-3-(2-hydroxy-2,2-diphenyl-acetoxy)-1-azonia-bicyclo[2.2.2]octane trifluoroacetate, (R)-1-[(2,5-Dimethyl-2H-pyrazol-3-ylcarbamoyl)-methyl]-3-(2-hydroxy-2,2-diphenyl-acetoxy)-1-azonia-bicyclo[2.2.2]octane trifluoroacetate, and (R)-1-[(2-Ethyl-2H-pyrazol-3-ylcarbamoyl)-methyl]-3-(2-hydroxy-2,2-diphenyl-acetoxy)-1-azonia-bicyclo-[2.2.2]octane trifluoroacetate are all prepared analogously to (R)-1-[(2-Bromo-phenyl-carbamoyl)-methyl]-3-(2-hydroxy-2,2-diphenyl-acetoxy)]-1-azonia-bicyclo[2.2.2]octane trifluoroacetate [Example 184] by replacing 2-Bromoaniline with the appropriate amine.

Example 190

(R)-1-(2-[(Furan-2-carbonyl)-amino]ethyl)-3-(2-hydroxy-2,2-diphenyl-acetyl)-1-azonia-bicyclo[2.2.2]octane hexafluorophosphate To a stirred solution of 2-furoic acid (91.5 mg, 8.21 mmol) and HATU (284 mg, 7.52 mmol) in DMF (7.5 ml) is added polymer bound morpholine, 2.5 mmol/g (1.36 g, 34.2 mmol). The reaction mixture is left to stand at room temperature for 15 minutes after which time, a solution comprising of (R)-1-(2-amino-ethyl)-3-(2-hydroxy-2,2-diphenyl-acetyl)-1-azonia-bicyclo[2.2.2]octane chloride hydrochloride [Example 180 i]] (310 mg, 6.84 mmol) in DMF (7.5 ml) is added. The reaction mixture is stirred at room temperature overnight. The reaction mixture is passed through a 2 g Isolute SPE (Al-B) cartridge. The filtrate is concentrated in vacuo and purification of the crude residue by chromatography on C18 silica, eluting with water:acetonitrile affords the title compound as a white solid.

Example 191

(R)-1-[2-[{Azetidine-3-carbonyl)-amino]-ethyl}-3-(2-hydroxy-2,2-diphenyl-acetoxy]-1-azonia-bicyclo[2.2.2]octane trifluoroacetate (i) (R)-1-{2-[1-tert-Butoxycarbonyl-azetidine-3-carbonyl)-amino]ethyl}-3-(2-hydroxy-2,2-diphenyl-acetoxy)-1-azonia-bicyclo[2.2.2]octane hexafluorophosphate:

This compound is prepared analogously to (R)-1-[2-[(Furan-2-carbonyl)-amino]ethyl]-3-(2-hydroxy-2,2-diphenyl-acetyl)-1-azonia-bicyclo[2.2.2]octane hexafluorophosphate [Example 190] by replacing 2-furoic acid with 1-BOC-azetidine-3-carboxylic acid.

(ii) (R)-1-[2-[(Azetidine-3-carbonyl)-amino]-ethyl]-3-(2-hydroxy-2,2-diphenyl-acetoxy)-1-azonia-bicyclo[2.2.2]octane trifluoroacetate:

(R)-1-(2-[(1-tert-butoxycarbonyl-azetidine-3-carbonyl)-amino]ethyl]-3-(2-hydroxy-2,2-diphenyl-acetoxy)1-azonia-bicyclo[2.2.2]octane hexafluorophosphate is dissolved in TFA:DCM (1:1) (2 ml) and stirred at room temperature for 1 hour. TFA:DCM (2 ml) is added to the reaction mixture to complete the reaction. The solvent is removed in vacuo and purification of the crude residue by mass directed preparative HPLC eluting with water:acetonitrile:trifluoroacetic acid yields the titled compound.

Example 192 to 195

These compounds, namely (R)-3-(2-Hydroxy-2,2-diphenyl-acetoxy)-1-(2-[((S)-pyrrolidine-2-carbonyl)-amino]-ethyl-1-azonia-bicyclo[2.2.2]octane trifluoroacetate, (R)-3-(2-Hydroxy-2,2-diphenyl-acetoxy)-1-[2-[((R)-piperidine-2-carbonyl)-amino]-ethyl]-1-azonia-bicyclo[2.2.2]octane trifluoroacetate, (R)-3-(2-Hydroxy-2,2-diphenyl-acetoxy)-1-[2-[((S)-piperidine-2-carbonyl)-amino]-ethyl]-1-azonia-bicyclo[2.2.2] octane trifluoroacetate and (R)-1-[2-[((S)-Azetidine-2-carbonyl)-amino]-ethyl]-3-(2-hydroxy-2,2-diphenyl-acetoxy)-1-azonia-bicyclo[2.2.2]octane trifluoroacetate are prepared analogously to (R)-1-[2-[(Azetidine-3-carbonyl)-amino]-ethyl]-3-(2-hydroxy-2,2-diphenyl-acetoxy)-1-azonia-bicyclo[2.2.2]octane trifluoroacetate [Example 191] by replacing 1-BOC-azetidine-3-carboxylic acid with the corresponding BOC protected amino acid.

Example 196

(R)-3-(2-Hydroxy-2,2-diphenyl-acetoxy)-1-(pyridine-2-ylcarbamoylmethyl)-azonia-bicyclo[2.2.2]octane trifluoroacetate This compound is prepared analogously to (R)-1-[(2-Bromo-phenylcarbamoyl)-methyl]-3-(2-hydroxy-2,2-diphenyl-acetoxy)]-1-azonia-bicyclo[2.2.2]octane trifluoroacetate [Example 184]. However instead of using PS-triphenylphosphine, BEMP 2.3 mmol/g (0.1 g, 1 eqv) is used with the PS-bromoacetamidomethyl-NovaGel 2.3 mmol/g (0.3 g, 1 eqv).

Example 197

(R)-3-(2-Hydroxy-2,2-diphenyl-acetoxy)-1-[4-methyl-pyrimidin-2-ylcarbamoyl)-methyl]-1-azonia-bicyclo[2.2.2]octane chloride This compound is prepared analogously to (R)3-(2-Hydroxy-2,2-di-thiophen-2-yl-acetoxy)-1-(pyrazin-2-ylcarbamoylmethyl)-1-azonia-bicyclo[2.2.2]octane chloride [Example 159B] by substituting hydroxy-di-thiophen-2-yl-acetic acid (R)-(1-aza-bicyclo[2.2.2]oct-3-yl) ester and Pyrazin-2-yl-amine with hydroxy-diphenyl-acetic acid (R)-(1-aza-bicyclo[2.2.2]oct-3-yl) ester and 4-Methyl-pyrimidin-2-ylamine.

Examples 198 to 201

These compounds, namely (R)-1-[(6-Ethyl-pyridin-2-ylcarbamoyl)methyl]-3-(2-hydroxy-2,2-diphenyl-acetoxy)-1-azonia-bicyclo[2.2.2]octane trifluoroacetate, (R)-3-(2-Hydroxy-2,2-diphenyl-acetoxy)-1-[(3-trifluoromethyl-pyridin-4-ylcarbamoyl)-methyl]-1-azonia-bicyclo [2.2.2]octane trifluoroacetate, R)-3-(2-Hydroxy-2,2-diphenyl-acetoxy)-1-[(3-hydroxy-pyridin-2-ylcarbamoyl)-methyl]-1-azonia-bicyclo[2.2.2]octane trifluoroacetate, and (R)-3-(2-Hydroxy-2,2-diphenyl-acetoxy)-1-(pyrimidin-2-ylcarbamoylmethyl)-1-azoniabicyclo[2.2.2]octane trifluoroacetate are all prepared analogously to (R)-1-[(2-bromo-phenyl-carbamoyl)-methyl]-3-(2-hydroxy-2,2-diphenyl-acetoxy)]-1-azonia-bicyclo[2.2.2]octane chloride [Example 184] by substituting 2-bromoaniline with the corresponding heterocyclic amines, however in these examples PS-triphenylphosphine is not used.

Examples 202 to 206

The title compounds, namely (R)-3-(2-Hydroxy-2,2-diphenyl-acetoxy)-1-[(4-methyl-oxazol-2-ylcarbamoyl)-methyl]-1-azonia-bicyclo[2.2.2]octane chloride, (R)-3-(2-Hydroxy-2,2-diphenyl-acetoxy)-1-(pyridin-4-ylcarbamoylmethyl)-1-azonia-bicyclo[2.2.2]octane chloride, (R)-3-(2-Hydroxy-2,2-diphenyl-acetoxy)-1-[(5-methyl-thiazol-2-ylcarbamoyl)-methyl]-1-azonia-bicyclo[2.2.2]octane chloride, (R)-3-(2-Hydroxy-2,2-diphenyl-acetoxy)-1-[(4-methyl-thiazol-2-ylcarbamoyl)-methyl]-1-azonia-bicyclo[2.2.2]octane chloride, and (R)-3-(2-Hydroxy-2,2-diphenyl-acetoxy)-1-(pyridin-3-ylcarbamoylmethyl)-1-azoniabicyclo[2.2.2] octane chloride, are all prepared analogously to (R)-3-(2-Hydroxy-2,2-di-thiophen-2-yl-acetoxy)-1-(pyrazin-2-ylcarbamoylm-ethyl)-1-azonia-bicyclo[2.2.2]octane chloride [Example 159B] by substituting hydroxy-di-thiophen-2-yl-acetic acid (R)-(1-aza-bicyclo[2.2.2]oct-3-yl) ester with hydroxyl-diphenyl-acetic acid(R)-(1-aza-bicyclo[2.2.2]oct-3-yl)ester and replacing Pyrazin-2-yl-amine with the corresponding heterocyclic amines.

Example 207

(R)-3-(2-Hydroxy-2,2-diphenyl-acetyl)-1-{2-[thiophene-2-carbonyl)-amino]-ethyl}-1-azonia-bicyclo[2.2.2]octane hexafluorophosphate To a stirred solution of 2-thiophenecarboxylic acid (15.4 mg, 0.12 mmol) and HATU (42 mg, 0.11 mmol) in DMF (0.6 ml) is added triethylamine (42 µl, 0.3 mmol). The reaction mixture is left to stand for 20 minutes after which rime, a solution comprising of (R)-1-(2-amino-ethyl)-3-(2-hydroxy-2,2-diphenyl-acetyl)-1-azonia-bicyclo[2.2.2]octane bromide [Example 49ii)] (45 mg, 0.1 mmol) in DMF (0.6 ml) is added. The reaction mixture is stirred ac room temperature overnight, The reaction mixture is passed through a 1 g Isolute SPE (Al-B) cartridge and the filtrate concentrated in vacuo. Purification by mass directed preparative HPLC eluting with water:acetonitrile:trifluoracetic acid yields the titled compound.

Examples 208 to 241

These compounds, namely (R)-3-(2-Hydroxy-2,2-diphenyl-acetoxy)-1-[2-[(3-methyl-thiophene-2-carbonyl)-amino]-ethyl]-1-azonia-bicyclo[2.2.2] octane hexafluoro phosphate, (R)-1-[2-[(3-Chloro-4-methyl-thiophene-2-carbonyl)-amino]-3-(2-hydroxy-2,2-diphenyl-acetoxy)-1-azonia-bicyclo[2.2.2]octane hexafluoro phosphate, (R)-1-[2-[(5-Chloro-3-methyl-benzo-[b]thiophene-2-carbonyl)-amino]-ethyl]-3-(2-hydroxy-2,2-diphenyl-acetoxy)-1-azonia-bicyclo-[2.2.2]octane hexafluorophosphate, (R)-3-(2-Hydroxy-2,2-diphenyl-acetoxy)-1-[2-[(2-hydroxy-6-methyl-pyridine-4-carbonyl)-amino]-ethyl]-1-azonia-bicyclo[2.2.2]octane hexafluoro-phosphate, (R)-3-(2-Hydroxy-2,2-diphenyl)-acetoxy)-1-[2-[(thieno[3,2-b]thiophene-2-carbonyl)-amino]-ethyl]-1-azonia-bicyclo [2.2.2] octane hexafluoro-phosphate, (R)-1-[2-[(6-Fluoro-4H-benzo[1,3]dioxine-8-carbonyl)-amino]-ethyl]-3-(2-hydroxy-2,2-diphenyl-acetoxy)-1-azonia-bicyclo[2.2.2] octane hexafluoro phosphate, (R)-1-(2-[(5-Bromo-thiophene-2-carbonyl)-amino]-ethyl]-3-(2-hydroxy-2,2-diphenyl-acetoxy)-1-azonia-bicyclo[2.2.2]octane hexafluorophosphate, (R)-3-(2-Hydroxy-2,2-diphenyl-acetoxy)-1-[2-(2-propoxy-benzoylamino)-ethyl]-1-azonia-bicyclo[2.2.2]octane hexafluorophosphate, (R)-1-[2-(5-Chloro-2-methoxy-benzoylamino)-ethyl]-3-(2-hydroxy-2,2-diphenyl-acetoxy)-1-azonia-bicyclo[2.2.2]octane hexafluorophosphate, (R)-3-(2-Hydroxy-2,2-diphenyl-acetoxy)-1-[2-[(pyridine-4-carbonyl)-amino]-ethyl]-1-azonia-bicyclo[2.2.2]octane hexafluorophosphate, (R)-1-[2-(2,6-Dimethoxy-benzoylamino)-ethyl]-3-(2-hydroxy-2,2-diphenyl-acetoxy)-1-azonia-bicyclo[2.2.2]octane hexafluorophosphate, (R)-1-(2-[(5-Bromo-pyridine-3-carbonyl)-amino]-ethyl]-3-(2-hydroxy-2,2-diphenyl-acetoxy)-1-azonia-bicyclo[2.2.2]octane hexafluorophosphate, (R)-1-[2-[(3,5-Dimethyl-isoxazole-4-carbonyl)-amino]-ethyl]-3-(2-hydroxy-2,2-diphenyl-acetoxy)-1-azonia-bicyclo[2.2.2] octane hexafluoro phosphate, (R)-1-[2-[(1-Hydroxy-cyclopropanecarbonyl)-amino]-ethyl]-3-(2-hydroxy-2,2-diphenyl-acetoxy)-1-azonia-bicyclo[2.2.2]-octane hexafluorophosphate, (R)-3-(2-Hydroxy-2,2-diphenyl-acetoxy)-1-[2-[(2-trifluoro-methyl-[1,8]naphthyridine-3-carbonyl)-amino]-ethyl]-1-azonia-bicyclo[2.2.2]octane hexafluorophosphate, (R)-3-(2-Hydroxy-2,2-diphenyl-acetoxy)-1-[2-[(6-methyl-pyridine-3-carbonyl)-amino]-ethyl]-1-azonia-bicyclo-[2.2.2]octane hexafluorophosphate, (R)-1-[2-(Cyclopropanecarbonyl-amino)-ethyl]-3-(2-hydroxy-2,2-diphenyl-acetoxy)-1-azonia-bicyclo-[2.2.2]octane hexafluorophosphate, (R)-1-[2-(4-Chloro-3-sulfamoyl-benzoylamino)-ethyl]-3-(2-hydroxy-2,2-diphenyl-acetoxy)-1-azonia-bicyclo[2.2.2]octane hexafluorophosphate, (R)-3-(2-Hydroxy-2,2-diphenyl-acetoxy)-1-[2-[(4,5,6,7-tetrahydro-benzo[c]thiophene-1-carbonyl)-amino]-ethyl]-1-azonia-bicyclo[2.2.2]-octane hexafluorophosphate, (R)-1-(2-[(2,7-Dimethyl-imidazo[1,2-a]pyridine-3-carbonyl)-amino]-ethyl]-3-(2-hydroxy-2,2-diphenyl-acetoxy)-1-azonia-bicyclo[2.2.2] octane hexa-fluorophosphate, (R)-1-[2-[(3-Chloro-4-methanesulfonyl-thiophene-2-carbonyl)-amino]-ethyl]-3-(2-hydroxy-2,2-diphenyl-acetoxy)-1-azonia-bicyclo-[2.2.2]octane hexafluorophosphate, (R)-1-[2-[(5-Chloro-thiophene-2-carbonyl)-amino]-ethyl]-3-(2-hydroxy-2,2-diphenyl-acetoxy)-1-azonia-bicyclo[2.2.2]octane hexafluorophosphate, (R)-1-[2-(3-Chloro-4-fluoro-benzoylamino)-ethyl]-3-(2-hydroxy-2,2-diphenyl-acetoxy)-1-azonia-bicyclo[2.2.2]octane hexafluorophosphate, (R)-3-(2-Hydroxy-2,2-diphenyl-acetoxy)-1-[2-[(3-methyl-benzo[b]thiophene-2-carbonyl)-amino]-ethyl]-1-azonia-bicyclo[2.2.2]octane hexa-fluorophosphate, (R)-3-(2-Hydroxy-2,2-diphenyl-acetoxy)-1-[2-[(3-methyl-5-trifluoromethyl-isoxazole-4-carbonyl)-amino]-ethyl]-1-azonia-bicyclo[2.2.2]octane hexafluorophosphate, (R)-3-(2-Hydroxy-2,2-diphenyl-acetoxy)-1-[2-(1-oxo-but-2-ynylamino)-ethyl]-1-azonia-bicyclo-[2.2.2]octane hexafluorophosphate, (R)-3-(2-Hydroxy-2,2-diphenyl-acetoxy)-1-(2-[(2-methoxy-pyridine-3-carbonyl)-amino]-ethyl)-1-azonia-bicyclo[2.2.2] octane hexafluoro-phosphate, (R)-1-[2-[(S-Dimethylsulfamoyl-2-methyl-furan-3-carbonyl)-amino]-ethyl]-3-(2-hydroxy-2,2-diphenyl-acetoxy)-1-azonia-bicyclo[2.2.2]octane hexafluorophosphate, (R)-3-(2-

Hydroxy-2,2-diphenyl-acetoxy)-1-[2-(3-phenyl-propynoylamino)-ethyl]-1-azonia-bicyclo-[2.2.2]octane hexafluorophosphate, (R)-1-[2-[(5-Chloro-4-methoxy-thiophene-3-carbonyl)-amino]-ethyl]-3-(2-hydroxy-2,2-diphenyl-acetoxy)-1-azonia-bicyclo[2.2.2]octane hexafluorophosphate, (R)-3-(2-Hydroxy-2,2-diphenyl-acetoxy)-1-[2-[((R)-tetrahydro-furan-2-carbonyl)-amino]-ethyl]-1-azonia-bicyclo [2.2.2]octane hexafluoro-phosphate, (R)-3-(2-Hydroxy-2,2-diphenyl-acetoxy)-1-[2-[(tetrahydro-pyran-4-carbonyl)-amino]-ethyl]-1-azonia-bicyclo[2.2.2]octane hexafluoro phosphate, (R)-3-(2-Hydroxy-2,2-diphenyl-acetoxy)-1-[2-[(3-methoxy-thiophene-2-carbonyl)-amino]-ethyl]-1-azonia-bicyclo-[2.2.2]octane hexafluoro-phosphate, and (R)-3-(2-Hydroxy-2,2-diphenyl-acetoxy)-1-[2-[(5-methoxy-thiophene-2-carbonyl)-amino]-ethyl]-1-azonia-bicyclo[2.2.2]octane hexafluoro-phosphate, are all prepared analogously to (R)-3-(2-Hydroxy-2,2-diphenyl-acetyl)-1-[2-[thiophene-2-carbonyl)-amino]-ethyl]-1-azonia-bicyclo[2.2.2]octane hexafluorophosphate [Ex. 207] by substituting 2-thiophenecarboxylic acid with the corresponding carboxylic acid.

Example 242

(R)-3-(2-Hydroxy-2,2-diphenyl-acetoxy)-1-(isoxazol-3ylcarbamoylmethyl)-1-azonia-bicyclo[2.2.2]octane bromide i) 2-Bromo-N-isoxazol-3-yl-acetamide:
To a stirred solution of bromoacetylbromide (5.36 ml, 61.6 mmol) in diethylether (100 ml) at −40° C. is added, dropwise over 20 minutes, a solution of 3-aminoisoxazol (5.0 ml, 67.0 mmol) and triethylamine (8.5 ml, 61.4 mmol) in diethylether (20 ml). Additional diethylether (50 ml) is added and stirring continued for 3 hours. The reaction mixture is filtered and the solution then washed with 1 M sodium carbonate solution, 1 M hydrochloric acid and brine. Concentration followed by purification by flash silica column chromatography (ethyl acetate/iso-hexane 4:7) gives the title compound as a white solid.

ii) (R)-3-(2-Hydroxy-2,2-diphenyl-acetoxy)-1-(isoxazol-3-ylcarbamoylmethyl)-1-azonia-bicyclo[2.2.2]octane bromide:
A solution of 2-Bromo-N-isoxazol-3-yl)-acetamide (0.82 g, 4.0 mmol) in chloroform/acetonitrile(1:1) is added to a solution of hydroxyl-diphenyl-acetic acid(R)-(1-aza-bicyclo-[2.2.2]oct-3-yl)ester (1.12 g, 3.32 mmol) in dry chloroform (10 ml) and the resulting mixture heated to 55° C. under an argon atmosphere for 4 hours. The mixture is then cooled to room temperature and concentrated. The residue is dissolved in acetonitrile and concentration followed by redissolution in hot acetone and cooling gives a jelly like precipitate which is filtered. Recrystallisation of the crude precipitate from acetonitrile containing a few drops of water followed by further crystallisation from acetonitrile gives the title compound as light brown crystals.

In an alternative method for preparing 2-Bromo-N-isoxazol-3-yl-acetamide, to a stirred solution of bromoacetylbromide (5.36 ml, 61.6 mmol) in diethylether (100 ml) at −40° C. is added, dropwise over 20 minutes, a solution of 3-aminoisoxazol (5.0 ml, 67.7 mmol) and triethylamine (8.5 ml, 61.4 mmol) in diethylether (20 ml). Additional diethylether (50 ml) is added and stirring continued for 3 hours. The reaction mixture is filtered and the solution then washed with 1 M sodium carbonate solution, 1 M hydrochloric acid and brine. Concentration followed by purification by flash silica column chromatography (ethyl acetate/iso-hexane 3:7) gives the title compound as a white solid.

Example 243

(R)-3-Hydroxy-2,2-di-thiophen-2-yl-acetoxy)-1-(isoxazol-3-ylcarbamoylmethyl)-1-azonia-bicyclo [2.2.2]octane bromide A solution of 2-Bromo-N-isoxazol-3-yl-acetamide [Example 242 i]] (0.70 g, 3.5 mmol) in chloroform (10 ml) is added to a solution of hydroxy-di-thiophen-2-yl-acetic acid (R)-(1-aza-bicyclo[2.2.2]oct-3-yl) ester (1.01 g, 2.9 mmol) acetonitrile (5 ml) and the resulting mixture heated to 55° C. under an argon atmosphere for 4 hours. The mixture is then cooled to room temperature and concentrated. The residue is triturated with ethylacetate and then purification by C-18 reverse phase column chromatography (eluent: water-acetonitrile) to give the title compound as a white foam.

Example 244

(R)-3-(2-Hydroxy-2,2-di-thiophen-2-yl-acetoxy)-1-(pyrimidin-4-ylcarbamoylmethyl)-1-azonia-bicyclo [2.2.2]octane bromide i) 2-Bromo-N-pyrimidin-4-yl-acetamide:
To a solution of 4-aminopyrimidine (7.0 g, 73.6 mmol) in chloroform (300 ml) under an argon atmosphere is added triethylamine (12.3 ml, 88.3 mmol) and the temperature of the resulting mixture reduced to −40° C. To this solution is added a solution of bromoacetylbromide (6.4 ml, 73.6 mmol) in chloroform (5 ml) dropwise and stirring continued for 1.5 hours. The reaction mixture is then quenched by addition to saturated aqueous sodium bicarbonate solution. The chloroform later is separated and washed with 0.5 M citric acid solution. Concentration followed by purification by flash silica column chromatography (gradient elution:ethyl acetate/hexane 1:4 to methanol/ethyl acetate 1:10) gives the title compound.

ii) (R)-3-(2-Hydroxy-2,2-di-thiophen-2-yl-acetoxy)-1-(pyrimidin-4-ylcarbamoylmethyl)-1-azonia-bicyclo[2.2.2]octane bromide:
A solution of 2-Bromo-N-pyrimidin-4-yl-acetamide (0.90 g, 4.17 mmol) and hydroxy-di-thiophen-2-yl-acetic acid (R)-(1-aza-bicyclo[2.2.2]oct-3-yl) ester (Example 70(ii)) (1.32 g, 3.79 mmol) in dry chloroform-acetonitrile (20 ml+4 ml) are heated at 50° C. for 3 hours. The mixture is then cooled to room temperature and concentrated. Purification by reverse phase C18 column chromatography (gradient elution 100% water to 100% acetonitrile) gives after concentration a light brown solid. The solid was triturated with hot acetonitrile then dissolved in hot acetonitrile containing a few drops of water. After standing at 5° C. for several hours crystals are formed which are filtered and dried to give the title compound.

Example 245

(R)-3-(2-Hydroxy-2,2-diphenyl-acetoxy)-1-(pyrazin-2-ylcarbamoylmethyl)-1-azonia bicyclo[2.2.2]octane A solution of 2-bromo-N-pyrazin-2-yl-acetamide (1.50 g, 6.94 mmol) and hydroxyl-diphenyl-acetic acid(R)-(1-aza-bicyclo[2.2.2]oct-3-yl)ester (2.13 g, 6.31 mmol) in dry chloroform (10 ml) are heated at 50° C. for 2 hours. The mixture is then cooled to room temperature filtered and concentrated.

The resulting foam is dissolved in acetonitrile and cooled to −20° C. an orange oil is formed from which the acetonitrile layer is decanted. The orange oil is dissolved in water and washed with chloroform before concentration. Redissolution in hot water followed by precipitation by cooling to room temperature gives the title product as a white solid.

Further especially preferred compounds of formula I include compounds of formula XIV where $R^1$, $R^2$, $R^3$, and $R^4$ are as shown in Table 3 below, the method of preparation being described hereinafter. All compounds are quaternary ammonium salts. The table also shows mass spectrometry data.

TABLE 3

| Ex. | $R^1$ and $R^3$ | $R^4$ | $R^2$ | M/s M+ |
|---|---|---|---|---|
| 246 | ![thiophene] | ![allyloxycarbonylmethyl] | OH | 448.3 |
| 247 | ![thiophene] | ![carboxymethyl] | OH | 408.3 |

Preparation of Specific Examples

Example 246

1-Allyloxycarbonylmethyl-3-(2-hydroxy-2,2-di-thiophen-2-yl-acetoxy)-1-azonia-bicyclo-[2.2.2]octane A solution of bromo-acetic acid allyl ester (0.8 g, 4.46 mmol) and hydroxy-di-thiophen-2-yl-acetic acid (R)-(1-azabicyclo[2.2.2]oct-3-yl) ester (Example 70(ii)) (1.3 g, 3.7 mmol) in dry chloroform are heated at 50° C. for 2 hours. The contents are then allowed to cool and then concentrated in vacuo. This residue is then taken up in 1% water in acetone at reflux and allowed to cool to room temp. After several hours a solid is formed which is filtered and dried to give the title compound as a brown solid.

Example 247

1-Carboxymethyl-3-(2-hydroxy-2,2-di-thiophen-2-yl-acetoxy)-1-azonia-bicyclo[2.2.2]octane To a stirred solution of 1-allyloxycarbonylmethyl-3-(2-hydroxy-2,2-di-thiophen-2-yl-acetoxy)-1-azonia-bicyclo [2.2.2]octane (Example 246) (0.79 g, 1.50 mmol) in dry chloroform, under argon, is added tetrakis-palladium triphenyl phosphine (0.02 g, 0.017 mmol). The mixture is stirred at room temp., under argon, for 20 minutes before morpholine (0.196 ml, 2.25 mmol) is added. Stirring is continued for a further 4 hrs at room temp. The mixture is concentrated in vacuo and purified by gradient C18 column chromatography to give a pale yellow solid. The solid is then redissolved in a small volume of acetonitrile containing a few drops of water. After several hours a solid is formed which is filtered and dried to give the title compound as a pale yellow solid.

The invention claimed is:
1. A compound of formula I

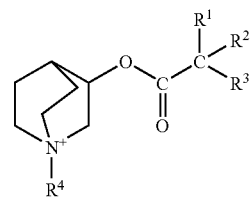

in salt or zwitterionic form wherein
$R^1$ and $R^3$ are each independently phenyl or a 5-membered heterocyclic group having at least one ring heteroatom selected from nitrogen, oxygen and sulphur;
$R^2$ is hydrogen, halo, hydroxy, $C_1$-$C_8$-alkoxy or $C_1$-$C_8$-alkyl optionally substituted by hydroxy;
$R^4$ is $C_1$-$C_8$-alkyl substituted by —$NR^5$—CO—$R^6$, —CO—$NR^9R^{10}$;
$R^5$ is hydrogen or $C_1$-$C_8$-alkyl;
$R^6$ is $C_1$-$C_8$-alkyl, $C_2$-$C_8$-alkenyl, $C_2$-$C_{10}$-alkynyl or $C_1$-$C_8$-alkoxy in each case optionally substituted by a 4- to 12-membered heterocyclic group having at least one ring heteroatom selected from nitrogen, oxygen and sulphur,
or $R^6$ is a 4- to 12-membered heterocyclic group having at least one ring heteroatom selected from nitrogen, oxygen and sulphur;
$R^9$ is hydrogen or $C_1$-$C_8$-alkyl;
$R^{10}$ is hydrogen, $C_1$-$C_8$-alkyl optionally substituted by cyano, amino, nitro, carboxy, $C_1$-$C_8$-alkoxy, or by a 4- to 12-membered heterocyclic group having at least one ring heteroatom selected from nitrogen, oxygen and sulphur,
or $R^{10}$ is a 4- to 12-membered heterocyclic group having at least one ring heteroatom selected from nitrogen, oxygen and sulphur.
2. A compound according to claim 1, wherein
$R^1$ and $R^3$ are each independently phenyl or a 5-membered heterocyclic group having at least one ring heteroatom selected from nitrogen, oxygen and sulphur;
$R^2$ is halo or hydroxy;
$R^4$ is $C_1$-$C_8$-alkyl substituted by —$NR^5$—CO—$R^6$, or —CO—$NR^9R^{10}$;
$R^5$ is hydrogen or $C_1$-$C_8$-alkyl;
$R^6$ is $C_1$-$C_8$-alkyl, $C_2$-$C_{10}$-alkynyl or $C_1$-$C_8$-alkoxy in each case optionally substituted by a 4- to 12-membered heterocyclic group having at least one ring heteroatom selected from nitrogen, oxygen and sulphur,
or $R^6$ is a 4- to 12-membered heterocyclic group having at least one ring heteroatom selected from nitrogen, oxygen and sulphur;
$R^9$ is hydrogen or $C_1$-$C_8$-alkyl;
$R^{10}$ is $C_1$-$C_8$-alkyl optionally substituted by cyano, $C_1$-$C_8$-alkoxy, or by a 4- to 12-membered heterocyclic group having at least one ring heteroatom selected from nitrogen, oxygen and sulphur,
or $R^{10}$ is a 4- to 12-membered heterocyclic group having at least one ring heteroatom selected from nitrogen, oxygen and sulphur.
3. A compound according to claim 1, wherein
$R^1$ and $R^3$ are each independently phenyl or a 5-membered heterocyclic group having at least one ring heteroatom selected from nitrogen, oxygen and sulphur;

R² is halo or hydroxy;
R⁴ is $C_1$-$C_8$-alkyl substituted by —NR⁵—CO—R⁶
   or —CO—NR⁹R¹⁰
R⁵ is hydrogen;
R⁶ is $C_1$-$C_8$-alkyl, or $C_1$-$C_8$-alkoxy in each case optionally substituted by a 5- to 12-membered heterocyclic group having at least one ring heteroatom selected from nitrogen, oxygen and sulphur, or R⁶ is a 5- to 12-membered heterocyclic group having at least one ring heteroatom selected from nitrogen, oxygen and sulphur;
R⁹ is hydrogen or $C_1$-$C_8$-alkyl;
R¹⁰ is $C_1$-$C_8$-alkyl optionally substituted by cyano, $C_1$-$C_8$-alkoxy, or a 5- to 12-membered heterocyclic group having at least one ring heteroatom selected from nitrogen, oxygen and sulphur,
or R¹⁰ is a 5- to 12-membered heterocyclic group having at least one ring heteroatom selected from nitrogen, oxygen and sulphur.

4. A compound according to claim 3, wherein
R¹ and R³ are each independently phenyl or a 5-membered heterocyclic group having at least one ring heteroatom selected from nitrogen, oxygen and sulphur;
R² is halo or hydroxy;
R⁴ is $C_1$-$C_8$-alkyl substituted by —NR⁵—CO—R⁶
   or —CO—NR⁹R¹⁰,
R⁵ is hydrogen;
R⁶ is $C_1$-$C_4$-alkyl or $C_1$-$C_4$-alkoxy in each case optionally substituted by a 5- to 12-membered heterocyclic group having at least one ring heteroatom selected from nitrogen, oxygen and sulphur,
or R⁶ is a 5- to 12-membered heterocyclic group having at least one ring heteroatom selected from nitrogen, oxygen and sulphur;
R⁹ is hydrogen or $C_1$-$C_4$-alkyl;
R¹⁰ is $C_1$-$C_4$-alkyl optionally substituted by cyano, $C_1$-$C_4$-alkoxy, or by a 5- to 12-membered heterocyclic group having at least one ring heteroatom selected from nitrogen, oxygen and sulphur,
or R¹⁰ is a 5- to 12-membered heterocyclic group having at least one ring heteroatom selected from nitrogen, oxygen and sulphur.

5. A compound according to formula XIV

XIV where R¹, R², R³, and R⁴ are as shown in the following table:

| R¹ and R³ | R⁴ | R² |
|---|---|---|
|  |  | OH |
|  |  | OH |
|  |  | OH |
|  |  | OH |
|  |  | OH |
|  |  | OH |
|  |  | OH |
|  |  | OH |
|  |  | OH |
|  |  | OH |

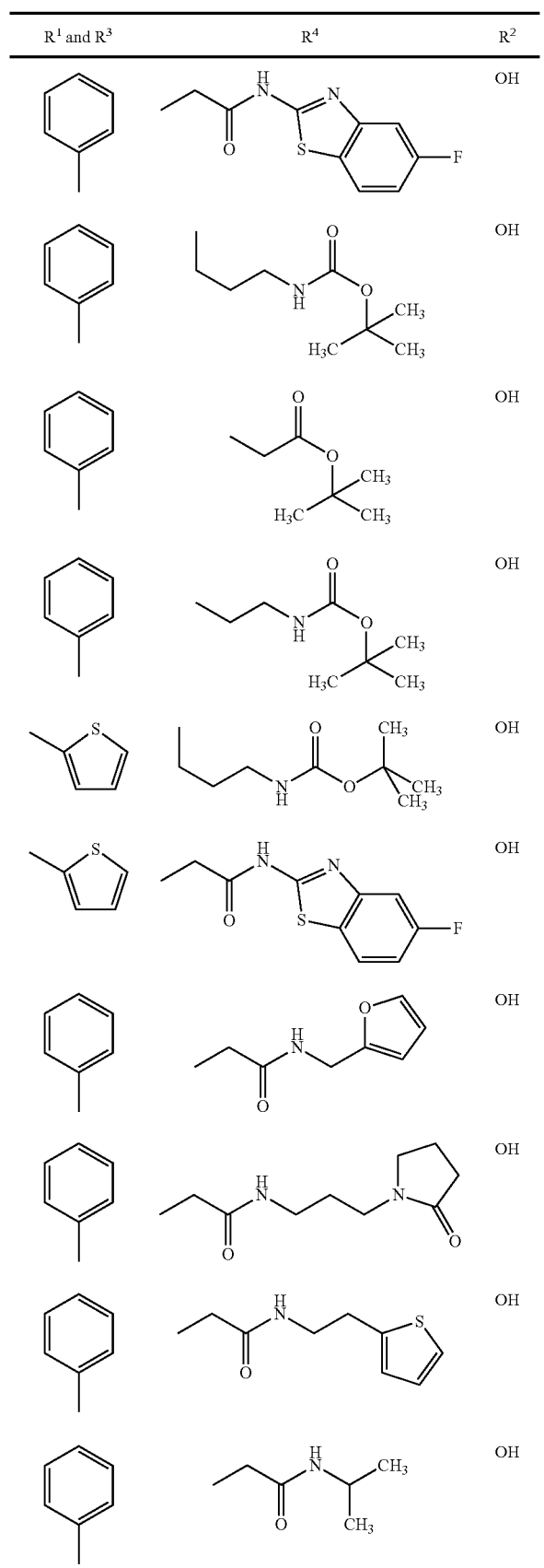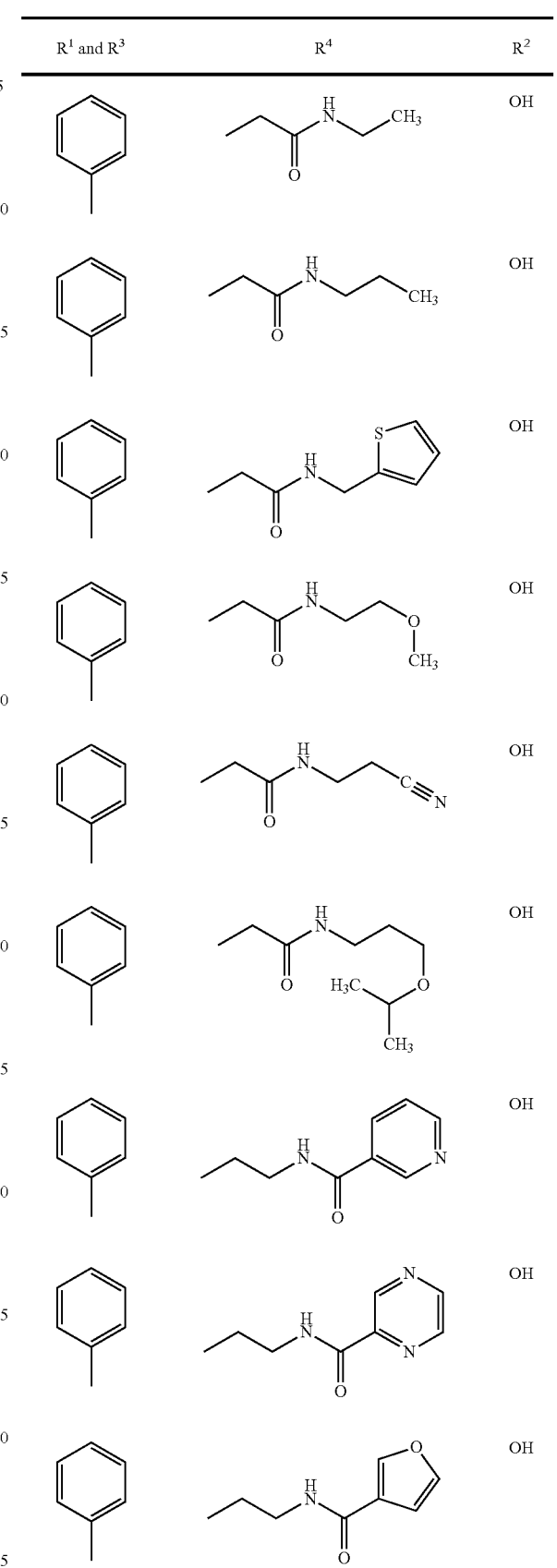

-continued
| $R^1$ and $R^3$ | $R^4$ | $R^2$ |
|---|---|---|
| 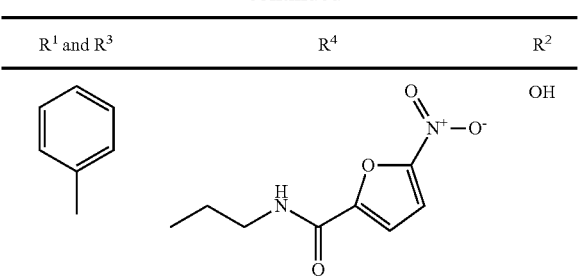 | | OH |
| 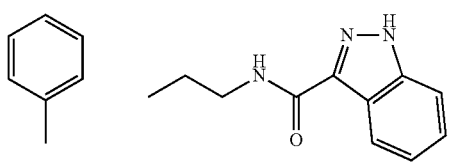 | | OH |
| 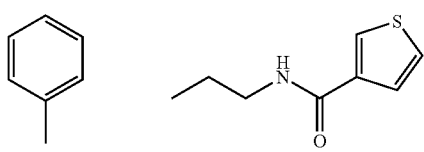 | | OH |
| 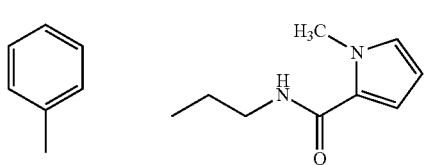 | | OH |
| 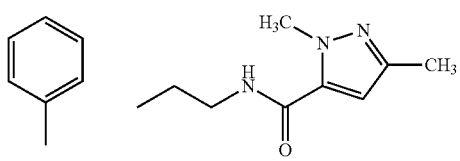 | | OH |
| 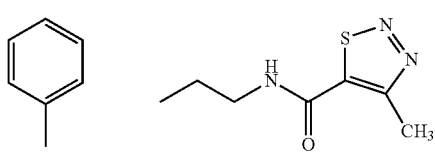 | | OH |
| 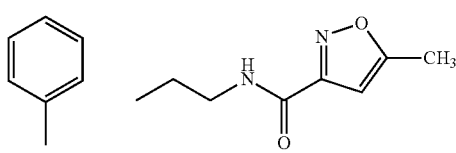 | | OH |
| 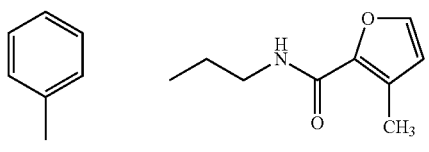 | | OH |
| 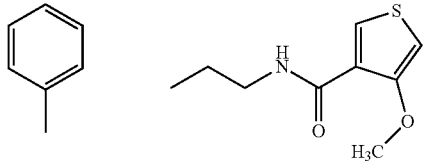 | | OH |
-continued
| $R^1$ and $R^3$ | $R^4$ | $R^2$ |
|---|---|---|
| 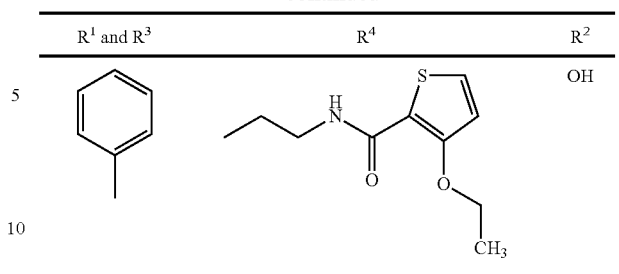 | | OH |
| 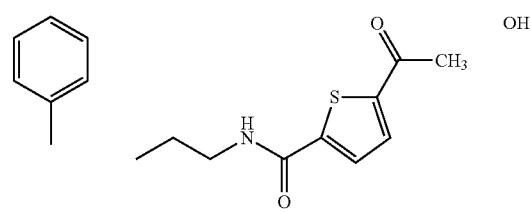 | | OH |
| 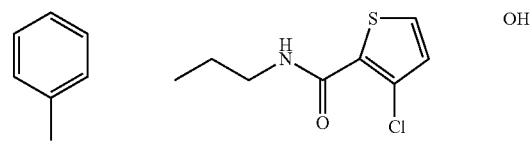 | | OH |
| 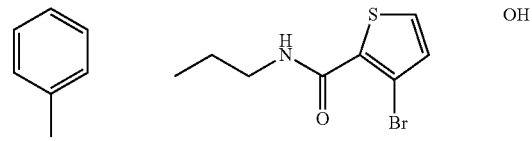 | | OH |
| 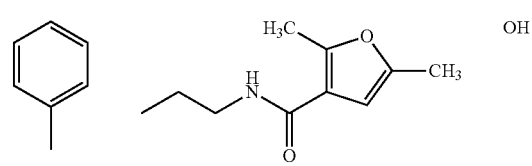 | | OH |
| 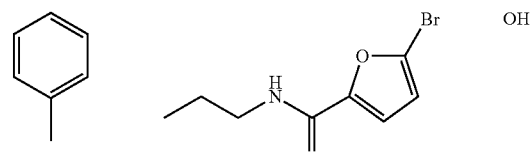 | | OH |
| 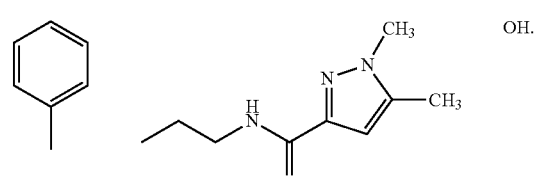 | | OH. |
6. A compound according to formula XIV
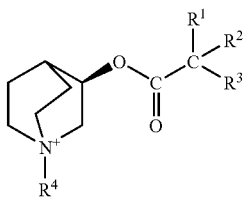
XIV

107
where R¹, R², R³, and R⁴ are as shown in the following table:
| R¹ and R³ | R⁴ | R² |
|---|---|---|
|  |  | OH |
|  |  | OH |
|  |  | OH |
|  |  | OH |
|  |  | OH |
|  |  | OH |
|  |  | OH |
|  |  | OH |
|  |  | OH |
108
-continued
| R¹ and R³ | R⁴ | R² |
|---|---|---|
|  |  | OH |
|  |  | OH |
|  |  | OH |
|  |  | OH |
|  |  | OH |
|  |  | OH |
|  |  | OH |
|  |  | OH |
|  | 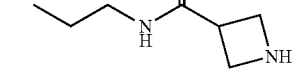 | OH |
|  |  | OH |

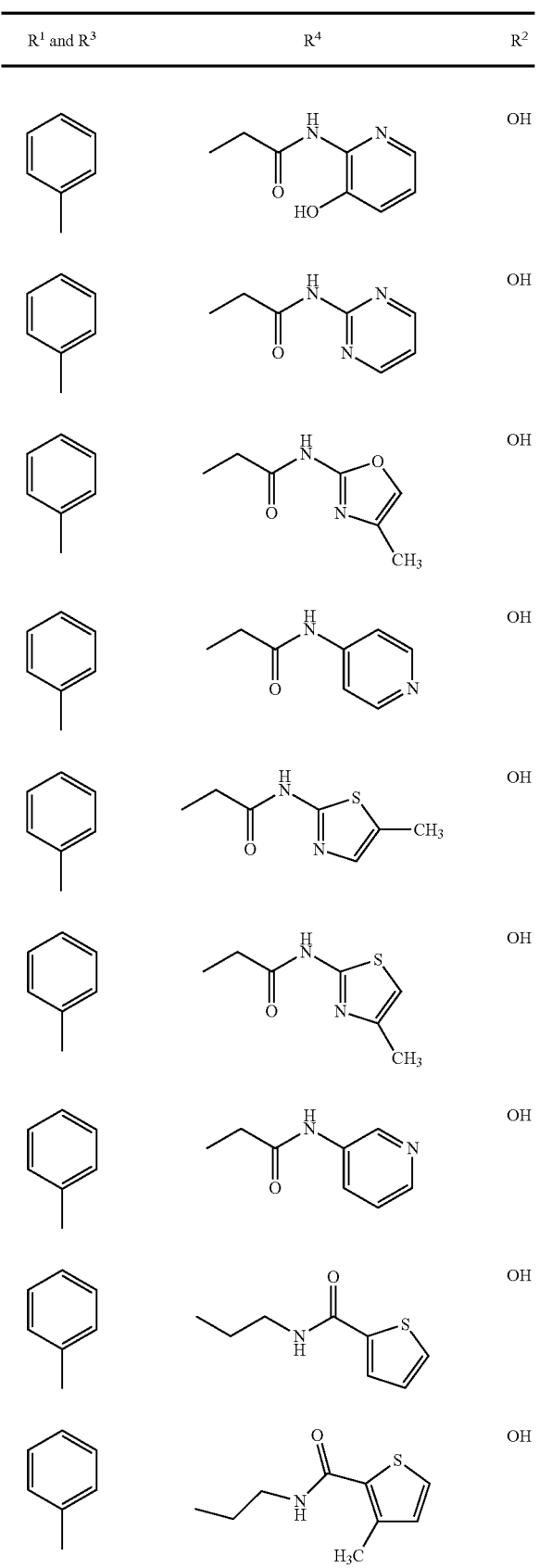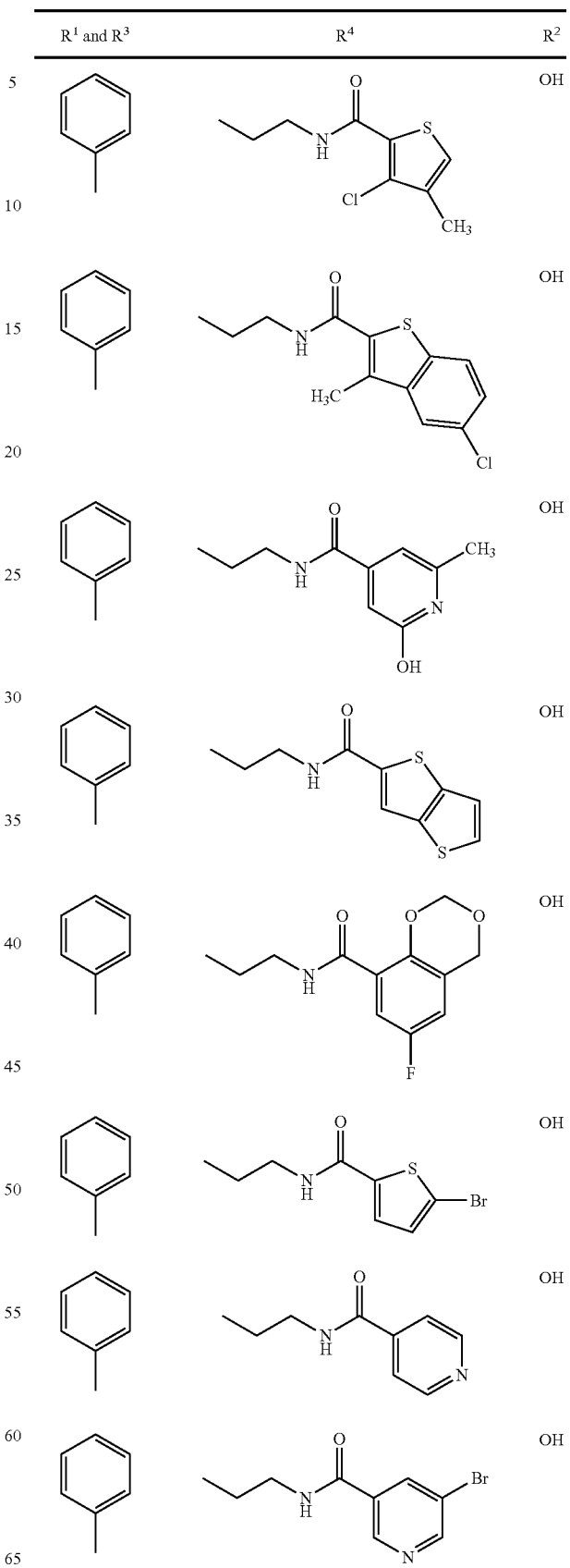

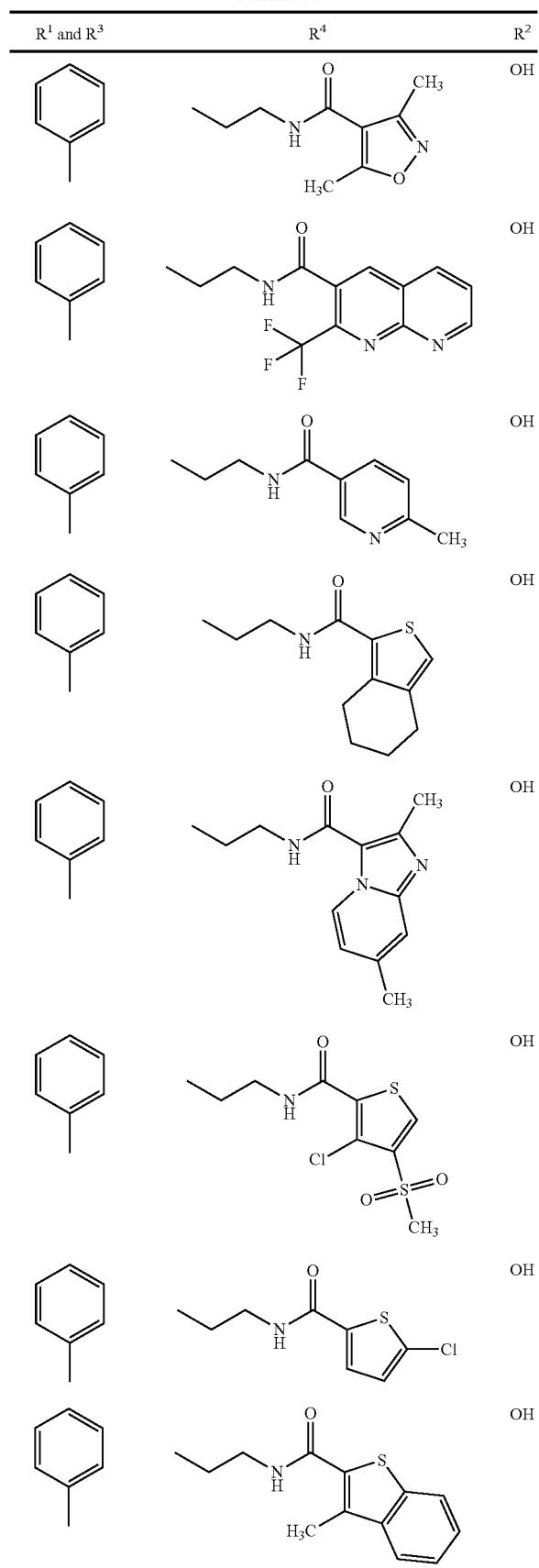
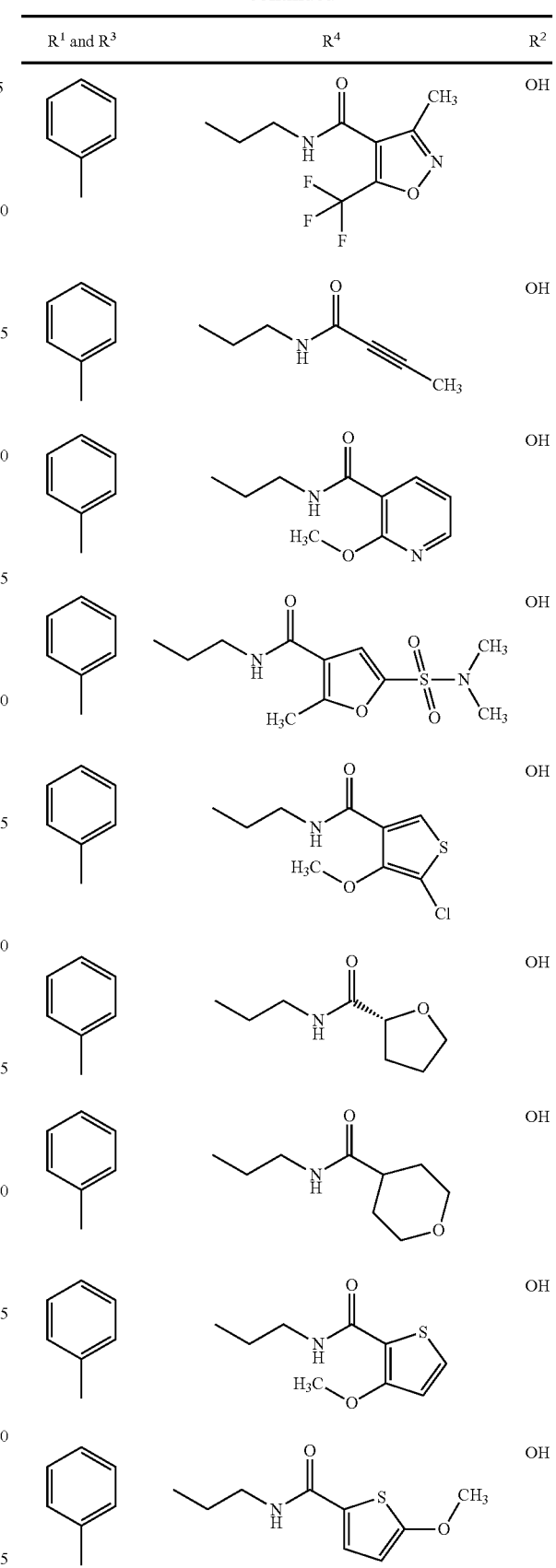

| $R^1$ and $R^3$ | $R^4$ | $R^2$ |
|---|---|---|
| [phenyl-methyl] | [propanoyl-N-isoxazol-3-yl] | OH |
| [methylthiophene] | [propanoyl-N-isoxazol-3-yl] | OH |
| [methylthiophene] | [propanoyl-N-pyrimidin-4-yl] | OH |
| [phenyl-methyl] | [propanoyl-N-pyrimidin-2-yl] | OH. |

7. A compound according to claim 1 in combination with another drug substance which is an anti-inflammatory, a bronchodilator, an antihistamine, a decongestant or an anti-tussive drug substance.

8. A process for the preparation of a compound of formula I as claimed in claim 1 which comprises (i) (A) reacting a compound of formula II

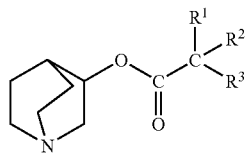

II or a protected form thereof where $R^1$, $R^2$ and $R^3$ are as defined in claim 1, with a compound of formula III $$R^4 - X$$

III where $R^4$ is as defined in claim 1 and X is chloro, bromo or iodo;

(B) for the preparation of compounds of formula I where $R^4$ is $C_1$-$C_8$-alkyl substituted by —$NR^5$—CO—$R^6$ where $R^5$ and $R^6$ are as defined in claim 1, reacting a compound of formula IV

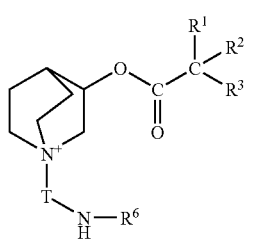

IV or a protected form thereof where $R^1$, $R^2$, $R^3$ and $R^5$ are as defined in claim 1, optionally in the presence of a cou pling agent, and T denotes $C_1$-$C_8$-alkylene, with a compound of formula V

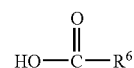

V where $R^6$ is as defined in claim 1 or an amide-forming derivative thereof such as an acid halide; or (C) for the preparation of compounds of formula I where $R^4$ is $C_1$-$C_8$-alkyl substituted by —CO—$NR^9R^{10}$ where $R^9$ and $R^{10}$ are as defined in claim 1, reacting a compound of formula VIII

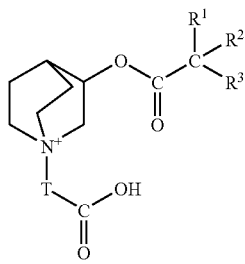

VIII or a protected form thereof where $R^1$, $R^2$, and $R^3$ are as defined in claim 1 and T denotes $C_1$-$C_8$-alkylene, optionally in the presence of a coupling agent, or an amide-forming derivative thereof such as an acid halide, with a compound of formula IX

IX where $R^9$ and $R^{10}$ are as defined in claim 1; and (ii) recovering the product in salt or zwitterionic form.

9. A pharmaceutical composition comprising as active ingredient a compound according to claim 1, optionally together with a pharmaceutically acceptable diluent or carrier.

10. A method of treating chronic obstructive pulmonary disease in a subject in need of such treatment, which comprises administering to said subject an effective amount of a compound of formula I as defined in claim 1 in free form or in the form of a pharmaceutically acceptable salt.

11. A compound according to claim 1 that is (R)-3-(2-hydroxy-2,2-diphenyl-acetoxy)-1-(isoxazol-3-ylcarbamoyl-methyl)-1-azonia-bicyclo[2.2.2]octane bromide.

12. A composition comprising a compound according to claim 11 in combination with a beta-2 adrenoceptor agonist and/or a corticosteroid.

13. The composition of claim 12 wherein the beta-2 adrenoceptor agonist is a compound of formula

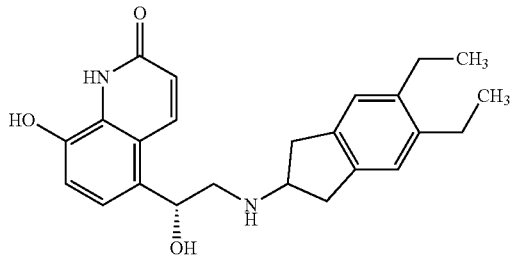

or a pharmaceutically acceptable salt thereof.

14. The composition of claim 13 wherein the corticosteroid is selected from budesonide, beclamethasone, fluticasone, ciclesonide and mometasone.

15. The composition of claim 14 wherein the corticosteroid is selected from budesonide, beclamethasone, fluticasone, ciclesonide and mometasone.

16. A method of treating chronic obstructive pulmonary disease in a subject in need of such treatment, which comprises administering to said subject an effective amount of a compound of formula I as defined in claim 11, in free form or in the form of a pharmaceutically acceptable salt.

* * * * *